United States Patent
Lee et al.

(10) Patent No.: US 12,421,205 B2
(45) Date of Patent: Sep. 23, 2025

(54) GLP-1 RECEPTOR AGONIST

(71) Applicant: HYUNDAI PHARM CO., LTD., Cheonan-si (KR)

(72) Inventors: Han Kyu Lee, Suwon-si (KR); Jeong-Un Hwang, Suwon-si (KR); Kyu-Hwan Lee, Yongin-si (KR); Hyung-Ho Choi, Suwon-si (KR); Jung-In Jang, Suwon-si (KR); Hyuck-Joo Lee, Suwon-si (KR); Seung-Tae Kang, Suwon-si (KR); Hyun-Ho Yoon, Suwon-si (KR); Neul Ha, Suwon-si (KR); Hyun-Hwa La, Suwon-si (KR); Jin Woong Kim, Suwon-si (KR); Dae Hoon Kim, Seoul (KR); Myoung Ki Baek, Seoul (KR)

(73) Assignee: Hyundai Pharm Co., Ltd., Cheonan-si (KR)

( * ) Notice: Subject to any disclaimer, the term of this patent is extended or adjusted under 35 U.S.C. 154(b) by 735 days.

(21) Appl. No.: 17/780,486

(22) PCT Filed: Dec. 1, 2020

(86) PCT No.: PCT/KR2020/017405
§ 371 (c)(1),
(2) Date: May 26, 2022

(87) PCT Pub. No.: WO2021/112538
PCT Pub. Date: Jun. 10, 2021

(65) Prior Publication Data
US 2023/0051318 A1    Feb. 16, 2023

(30) Foreign Application Priority Data
Dec. 2, 2019  (KR) .................. 10-2019-0158410

(51) Int. Cl.
*C07D 401/10* (2006.01)
*C07D 235/12* (2006.01)
*C07D 401/14* (2006.01)
*C07D 405/06* (2006.01)
*C07D 405/14* (2006.01)
*C07D 409/14* (2006.01)
*C07D 413/06* (2006.01)
*C07D 413/14* (2006.01)

(52) U.S. Cl.
CPC ......... *C07D 401/10* (2013.01); *C07D 235/12* (2013.01); *C07D 401/14* (2013.01); *C07D 405/06* (2013.01); *C07D 405/14* (2013.01); *C07D 409/14* (2013.01); *C07D 413/06* (2013.01); *C07D 413/14* (2013.01)

(58) Field of Classification Search
CPC .................................................. C07D 401/10
See application file for complete search history.

(56) References Cited

U.S. PATENT DOCUMENTS

| | | | |
|---|---|---|---|
| 10,208,019 B2 * | 2/2019 | Aspnes | A61P 17/06 |
| 11,702,404 B2 * | 7/2023 | Ammann | C07D 409/14 |
| | | | 514/210.02 |
| 2013/0018039 A1 | 1/2013 | Bodmer et al. | |
| 2019/0276440 A1 | 9/2019 | Zhao et al. | |
| 2020/0407347 A1 | 12/2020 | Coates et al. | |
| 2021/0171499 A1 | 6/2021 | Ammann et al. | |

FOREIGN PATENT DOCUMENTS

| | | |
|---|---|---|
| CN | 115279750 A | 11/2022 |
| CN | 115697999 A | 2/2023 |
| EP | 4119555 A1 | 1/2023 |
| JP | 2012-167027 A | 9/2012 |
| WO | 02/46168 A1 | 6/2002 |
| WO | 2008/012623 A1 | 1/2008 |
| WO | 2008/122510 A1 | 10/2008 |
| WO | 2015/091531 A1 | 6/2015 |
| WO | 2018/109607 A1 | 6/2018 |
| WO | 2020/207474 A1 | 10/2020 |
| WO | WO 2021160127 A1 | 8/2021 |
| WO | WO 2022078352 A1 | 4/2022 |

OTHER PUBLICATIONS

Office Action, with English translation, dated May 17, 2024, for Chinese Patent Application No. 202080084248.4. (12 pages).
Office Action, issued Oct. 12, 2023, for Chinese Patent Application No. 2020800842484, 21.
Extended European Search Report, dated Oct. 7, 2022, for European Application No. 20895723.3-1110, 6 pages.
International Search Report and Written Opinion, mailed Mar. 16, 2021, for International Patent Application No. PCT/KR2020/017405. (6 pages).

* cited by examiner

*Primary Examiner* — Golam M Shameem
(74) *Attorney, Agent, or Firm* — Seed IP Law Group LLP

(57) ABSTRACT

The present invention relates to a compound represented by Formula 1 wherein A, B, L, X, and $R_1$ to $R_6$ are as described herein, or a pharmaceutically acceptable salt thereof, which serves as a GLP-1 receptor agonist and may be useful in the prevention or treatment of a disease associated with GLP-1 activity.

15 Claims, No Drawings

GLP-1 RECEPTOR AGONIST

TECHNICAL FIELD

The present invention relates to a GLP-1 receptor agonist having a novel structure.

BACKGROUND ART

Diabetes is a metabolic disease which is caused by deficiency of insulin secretion or insulin action, and can be mainly classified into type 1 and type 2 depending on its mechanism. Type 1 diabetes is caused by deficiency of insulin secretion resulting from autoimmune destruction of pancreatic beta cells. Type 2 diabetes, also referred to as insulin-independent diabetes, is mainly caused because the amount of insulin produced according to an increase in blood sugar is not sufficient for cells to absorb glucose and reduce blood sugar levels. Treatment of Type 1 diabetes requires insulin therapy which involves injecting insulin externally, and for type 2 diabetes, a therapeutic agent is administrated alone or in combination, or insulin therapy is used, depending on the disease progression.

Currently known oral diabetes medicines include insulin secretagogues, biguanides, alpha-glucosidase inhibitors, thiazolidinedione, sodium-glucose cotransporter 2 (SGLT-2) selective inhibitors, and the like. Insulin secretagogues are, for example, sulfonylurea (e.g., glipizide, glimepyride, glyburide), meglitinide (e.g., nateglinide, repaglinide) and dipeptidyl peptidase IV (DPP-IV) inhibitors (eg, sitagliptin, vildagliptin, alogliptin, dutogliptin, linagliptin, saxagliptin), and the like. Biguanides are believed to act primarily to reduce the production of glucose in the liver, and the examples thereof include metformin, and the like. Alpha-glucosidase inhibitors reduce the absorption of glucose in the intestine, and the examples thereof include acarbose, and the like. Thiazolidinediones act on a specific receptor (peroxisome proliferatoractivated receptor-gamma) in liver, muscle, and adipose tissue, and the examples thereof include pioglitazone, rosiglitazone, and the like. SGLT-2 inhibitors inhibit glucose reuptake in the kidney, thereby lowering blood glucose levels, and the examples thereof include dapagliflozin, empagliflozin, canagliflozin, ertugliflozin, and the like.

However, besides the positive aspects of maintaining continued normal blood sugar levels, oral diabetes medicines currently used in clinical practice cause various side effects such as hypoglycemia, diarrhea, weight gain, cardiovascular problems, liver toxicity when taken for a long time, or many of them have a limited effect. In addition, insulin administration, which is the last treatment method, is also inconvenient because of having to be subcutaneously injected two or three times a day, and is likely to cause hypoglycemia which is the most serious side effect.

To overcome such problems, glucagon-like peptide-1 (GLP-1) receptor agonists have recently emerged as a next generation diabetes medicine.

GLP-1, a long incretin hormone having 30 amino acids, is secreted by intestinal L-cells in response to ingestion of food. In a healthy individual, GLP-1 plays a significant role in controlling postprandial blood glucose by promoting glucose-dependent insulin secretion in the pancreas. GLP-1 also inhibits glucagon secretion, causing a decrease in hepatic glucose production. In addition, GLP-1 delays gastric emptying, slows small intestine motility, and thus delays food absorption.

GLP-1 receptor agonists, such as GLP-1 and analogs or derivatives thereof, exhibit good potential in clinical trials for the treatment of type 2 diabetes, and induces a number of biological effects such as stimulation of insulin secretion, inhibition of glucagon secretion, inhibition of gastric fasting, inhibition of gastric motility or intestinal motility, and induction of weight loss ((i) Cardiovascular Diabetology 2014, 13:142; (ii) Front. Neurosci) 9:92; (iii) Peptides 100 (2018) 190-201; (iv) World J Hepatol) 2018 Nov. 27; 10(11): 790-794). Further, even when taken for a long time, GLP-1 receptor agonists provide pancreatic protection, have no risk of hypoglycemia, and maintain adequate blood sugar levels for a long time. GLP-1 receptor agonists known to date include liraglutide, albiglutide, exenatide, lixisenatide, dulaglutide, semaglutide, and the like.

Accordingly, the present inventors completed the present invention by intensively investigating a GLP-1 receptor agonist having a novel structure to find that the compounds described herein have an excellent effect as a GLP-1 receptor agonist.

DISCLOSURE OF INVENTION

Technical Problem

The present invention is to provide a GLP-1 receptor agonist having a novel structure.

Solution to Problem

To solve the above problems, the present invention provides a compound represented by the following Formula 1, or a pharmaceutically acceptable salt thereof:

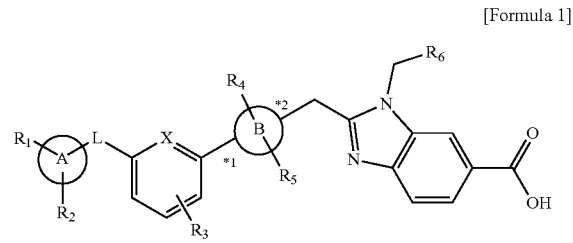

[Formula 1]

wherein,

A is $C_{6-10}$ aryl; $C_{3-7}$ cycloalkyl; 5- or 6-membered heteroaryl containing one heteroatom selected from N, O, and S; 5- or 6-membered heterocycloalkyl containing one heteroatom selected from N, O, and S; or 9- or 10-membered fused heteroaryl containing at least one heteroatom selected from N, O, and S, B is any one of the following (1) to (5),

(1)

(2)

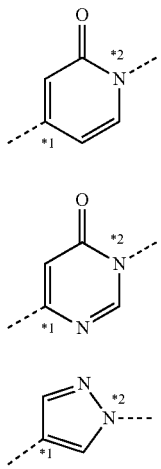

L is —(CH$_2$)$_n$-O—, —O—(CH$_2$)$_n$—, —(CH$_2$)$_n$—NH—, —NH—(CH$_2$)$_n$—, —(CH$_2$)$_n$—N(C$_{1-5}$ alkyl)-, —N(C$_{1-5}$ alkyl)-(CH$_2$)$_n$—, —CONH—, or —NHCO—, where n is 1 or 2, X is CH or N, R$_1$ and R$_2$ are each independently selected from the group consisting of hydrogen, C$_{1-5}$ alkyl, C$_{1-5}$ alkoxy, C$_{1-5}$ haloalkyl, halogen, cyano, and nitro, R$_3$ is hydrogen or halogen, R$_4$ and R$_5$ are each independently selected from the group consisting of hydrogen, C$_{1-5}$ alkyl, C$_{1-5}$ alkoxy, C$_{1-5}$ haloalkyl, halogen, cyano, and nitro, R$_6$ is —(CH$_2$)$_m$—O—(C$_{1-5}$ alkyl) (where m is 1 or 2); C$_{1-5}$ haloalkyl; 5- or 6-membered heteroaryl containing one or two heteroatoms selected from N, O, and S, which is unsubstituted or substituted with C$_{1-5}$ alkyl; or 4- or 5-membered heterocycloalkyl containing one heteroatom selected from N, O, and S, which is unsubstituted or substituted with C$_{1-5}$ alkyl.

In Formula 1, symbols "*1" and "*2" indicated in B mean respective bonding positions. That is, in Formula 1, it means that each compound has the following structure according to (1) to (5) of B.

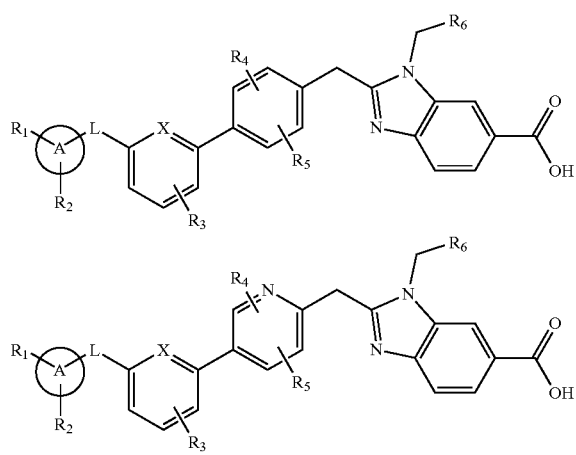

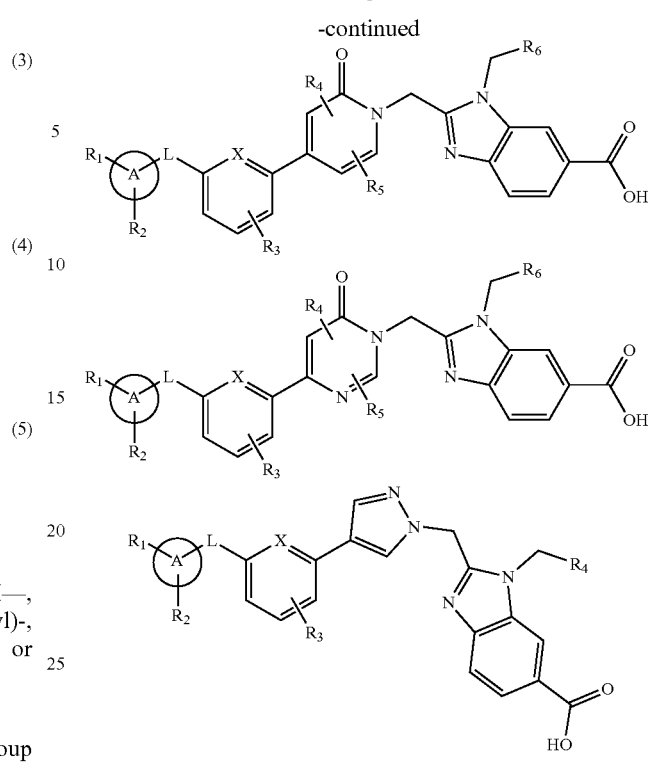

Preferably, A is phenyl; C$_{3-7}$ cycloalkyl; 5- or 6-membered heteroaryl containing one heteroatom selected from N, O, and S; or a 9- or 10-membered benzo-fused ring fused with 5- or 6-membered heteroaryl containing one or two heteroatoms selected from N, O, and S. More preferably, A is phenyl, pyrrolyl, pyridinyl, benzothiazolyl, benzoxazolyl, benzimidazolyl, cyclopropyl, or cyclobutyl. More preferably, A is phenyl, pyridinyl, benzothiazolyl, or cyclopropyl.

Preferably, L is —(CH$_2$)$_n$—O— or —O—(CH$_2$)$_n$— (n is 1 or 2), and more preferably, L is —CH$_2$O— or —OCH$_2$—.

Preferably, R$_1$ is hydrogen, C$_{1-5}$ alkyl, C$_{1-5}$ alkoxy, C$_{1-5}$ haloalkyl, halogen, cyano, or nitro, and R$_2$ is hydrogen or halogen.

More preferably, R$_1$ is hydrogen, methyl, methoxy, trifluoromethyl, fluoro, chloro, bromo, cyano, or nitro, and more preferably, R$_2$ is hydrogen, fluoro, chloro, or bromo.

Preferably, R$_3$ is hydrogen, fluoro, chloro, or bromo.

Preferably, R$_4$ is hydrogen, C$_{1-5}$ alkyl, C$_{1-5}$ alkoxy, halogen, or nitro, and R$_5$ is hydrogen or halogen.

More preferably, R$_4$ is hydrogen, methyl, methoxy, fluoro, chloro, bromo, or nitro, and more preferably, R$_5$ is hydrogen, fluoro, chloro, or bromo.

Preferably, R$_6$ is —(CH$_2$)$_m$—O—(C$_{1-5}$ alkyl) (m is 1); C$_{1-5}$ haloalkyl; heteroaryl selected from thiophenyl, furanyl, pyrrolyl, imidazolyl, pyrazolyl, oxazolyl, isoxazolyl, thiazolyl, isothiazolyl, pyridinyl, pyrimidinyl, and pyrazinyl, wherein the heteroaryl is unsubstituted or substituted with C$_{1-5}$ alkyl; or heterocycloalkyl selected from oxetanyl, azetidinyl, tetrahydrofuranyl, and pyrrolidinyl.

More preferably, R$_6$ is —CH$_2$—O—CH$_3$; —CH$_2$F; furanyl; imidazolyl unsubstituted or substituted with methyl or ethyl; oxazolyl; pyridinyl; thiophenyl; oxetanyl; or tetrahydrofuranyl.

Preferably, Formula 1 is represented by the following Formula 1-1:

[Formula 1-1]

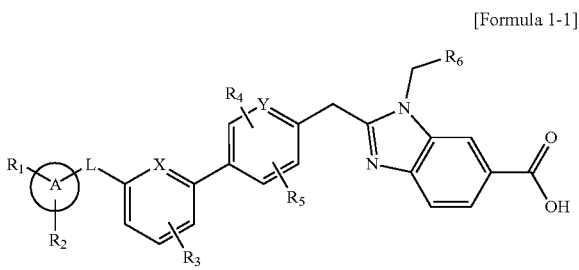

wherein
Y is CH or N,
A, L, X, and $R_1$ to $R_6$ are as defined above.
Preferably, Formula 1 is represented by the following Formula 1-2:

[Formula 1-2]

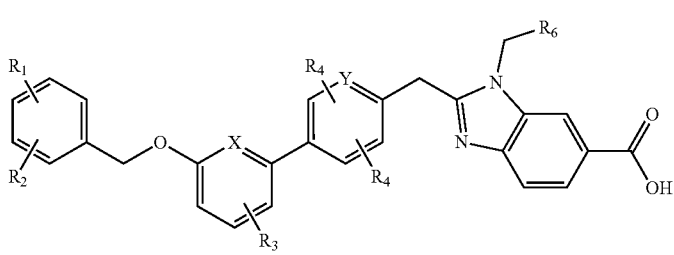

wherein
Y is CH or N,
X and $R_1$ to $R_6$ are as defined above.
Preferably, Formula 1 is represented by the following Formula 1-3:

[Formula 1-3]

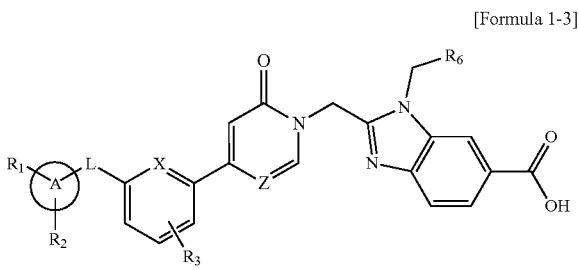

wherein
Z is CH or N,
A, L, X and $R_1$, $R_2$, $R_3$ and $R_6$ are as defined above.
Preferably, Formula 1 is represented by the following Formula 1-4:

[Formula 1-4]

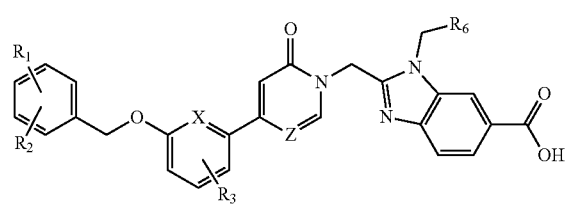

wherein
Z is CH or N,
X and $R_1$, $R_2$, $R_3$ and $R_6$ are as defined above.

Representative examples of the compounds represented by Formula 1 are as follows:
1) 2-(4-(6-(4-chloro-2-fluorobenzyloxy)pyridin-2-yl)benzyl)-1-(pyridin-3-ylmethyl)-1H-benzo[d]imidazole-6-carboxylic acid,
2) 2-(4-(6-(4-chloro-2-fluorobenzyloxy)pyridin-2-yl)benzyl)-1-(2-methoxyethyl)-1H-benzo[d]imidazole-6-carboxylic acid,
3) 2-(4-(6-(4-chloro-2-fluorobenzyloxy)pyridin-2-yl)-2-fluorobenzyl)-1-(2-methoxyethyl)-1H-benzo[d]imidazole-6-carboxylic acid,
4) 2-(4-(6-(4-chloro-2-fluorobenzyloxy)pyridin-2-yl)-3-methylbenzyl)-1-(2-methoxyethyl)-1H-benzo[d]imidazole-6-carboxylic acid,
5) 2-(4-(6-(4-chloro-2-fluorobenzyloxy)pyridin-2-yl)-2-nitrobenzyl)-1-(2-methoxyethyl)-1H-benzo[d]imidazole-6-carboxylic acid,
6) 2-(4-(6-(4-chloro-2-fluorobenzyloxy)pyridin-2-yl)-3-fluorobenzyl)-1-(2-methoxyethyl)-1H-benzo[d]imidazole-6-carboxylic acid,
7) 2-(4-(6-(((4-chloro-2-fluorophenoxy)methyl)pyridin-2-yl)-2-nitrobenzyl)-1-(2-methoxy ethyl)-1H-benzo[d]imidazole-6-carboxylic acid,
8) 2-((3'-(4-cyano-2-fluorobenzyloxy)biphenyl-4-yl)methyl)-1-((tetrahydrofuran-2-yl)methyl)-1H-benzo[d]imidazole-6-carboxylic acid,
9) 2-((3'-(4-cyano-2-fluorobenzyloxy)-2-fluorobiphenyl-4-yl)methyl)-1-((tetrahydrofuran-2-yl)methyl)-1H-benzo[d]imidazole-6-carboxylic acid,
10) 2-(4-(6-(4-chloro-2-fluorobenzyloxy)pyridin-2-yl)benzyl)-1-((tetrahydrofuran-2-yl)methyl)-1H-benzo[d]imidazole-6-carboxylic acid,
11) 2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid,
12) 2-(4-(6-(4-chloro-2-fluorobenzyloxy)pyridin-2-yl)benzyl)-1-(furan-2-ylmethyl)-1H-benzo[d]imidazole-6-carboxylic acid, 13) 2-(4-(6-(4-chloro-2-fluorobenzyloxy)pyridin-2-yl)-2-fluorobenzyl)-1-(furan-2-ylmethyl)-1H-benzo[d]imidazole-6-carboxylic acid,
14) 2-((3'-(4-cyano-2-fluorobenzyloxy)-3-fluorobiphenyl-4-yl)methyl)-1-((tetrahydrofuran-2-yl)methyl)-1H-benzo[d]imidazole-6-carboxylic acid,
15) 2-(4-(6-(4-cyano-2-fluorobenzyloxy)pyridin-2-yl)-2-fluorobenzyl)-1-((tetrahydrofuran-2-yl)methyl)-1H-benzo[d]imidazole-6-carboxylic acid,
16) 2-((3'-(4-chloro-2-fluorobenzyloxy)-3-fluorobiphenyl-4-yl)methyl)-1-((tetrahydrofuran-2-yl)methyl)-1H-benzo[d]imidazole-6-carboxylic acid,
17) 2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid,
18) 2-(4-(6-(4-cyano-2-fluorobenzyloxy)pyridin-2-yl)benzyl)-1-(furan-2-ylmethyl)-1H-benzo[d]imidazole-6-carboxylic acid,
19) 2-(4-(6-(4-cyano-2-fluorobenzyloxy)pyridin-2-yl)-2-fluorobenzyl)-1-(furan-2-ylmethyl)-1H-benzo[d]imidazole-6-carboxylic acid,
20) 2-(4-(6-(4-cyano-2-fluorobenzyloxy)pyridin-2-yl)benzyl)-1-(2-methoxyethyl)-1H-benzo[d]imidazole-6-carboxylic acid,
21) 2-((3'-(4-cyano-2-fluorobenzyloxy)biphenyl-4-yl)methyl)-1-(2-methoxyethyl)-1H-benzo[d]imidazole-6-carboxylic acid,
22) 2-((3'-(4-chloro-2-fluorobenzyloxy)biphenyl-4-yl)methyl)-1-(2-methoxyethyl)-1H-benzo[d]imidazole-6-carboxylic acid,
23) 1-(furan-2-ylmethyl)-2-((5-(3-(3-methoxybenzyloxy)phenyl)pyridin-2-yl)methyl)-1H-benzo[d]imidazole-6-carboxylic acid,
24) 2-((3'-(4-chloro-2-fluorobenzyloxy)biphenyl-4-yl)methyl)-1-((tetrahydrofuran-2-yl)methyl)-1H-benzo[d]imidazole-6-carboxylic acid,
25) 2-(4-(6-(4-cyano-2-fluorobenzyloxy)pyridin-2-yl)-2-fluorobenzyl)-1-(2-methoxyethyl)-1H-benzo[d]imidazole-6-carboxylic acid,
26) 2-((3'-(4-cyano-2-fluorobenzyloxy)-3-fluorobiphenyl-4-yl)methyl)-1-(2-methoxyethyl)-1H-benzo[d]imidazole-6-carboxylic acid,
27) 2-((3'-(4-cyano-2-fluorobenzyloxy)biphenyl-4-yl)methyl)-1-(furan-2-ylmethyl)-1H-benzo[d]imidazole-6-carboxylic acid,
28) 2-((3'-(4-cyano-2-fluorobenzyloxy)-3-fluorobiphenyl-4-yl)methyl)-1-(furan-2-ylmethyl)-1H-benzo[d]imidazole-6-carboxylic acid,
29) 2-((3'-(4-cyano-2-fluorobenzyloxy)-2-methylbiphenyl-4-yl)methyl)-1-(furan-2-ylmethyl)-1H-benzo[d]imidazole-6-carboxylic acid,
30) 2-(4-(6-(4-cyano-2-fluorobenzyloxy)pyridin-2-yl)-3-methylbenzyl)-1-(furan-2-ylmethyl)-1H-benzo[d]imidazole-6-carboxylic acid,
31) 2-(4-(6-((4-chloro-2-fluorophenoxy)methyl)pyridin-2-yl)-2-fluorobenzyl)-1-(2-methoxyethyl)-1H-benzo[d]imidazole-6-carboxylic acid,
32) 2-((3'-(4-chloro-2-fluorobenzyloxy)-3-fluorobiphenyl-4-yl)methyl)-1-(oxazol-5-ylmethyl)-1H-benzo[d]imidazole-6-carboxylic acid,
33) 2-((3'-(4-chloro-2-fluorobenzyloxy)-2-fluorobiphenyl-4-yl)methyl)-1-(oxazol-5-ylmethyl)-1H-benzo[d]imidazole-6-carboxylic acid,
34) 2-(4-(6-(4-chloro-2-fluorobenzyloxy)pyridin-2-yl)-2-fluorobenzyl)-1-(oxazol-5-ylmethyl)-1H-benzo[d]imidazole-6-carboxylic acid,
35) 2-(4-(6-(4-chloro-2-fluorobenzyloxy)pyridin-2-yl)-3-fluorobenzyl)-1-(oxazol-5-ylmethyl)-1H-benzo[d]imidazole-6-carboxylic acid,
36) 2-((3'-(4-chloro-2-fluorobenzyloxy)-3-fluorobiphenyl-4-yl)methyl)-1-(2-methoxyethyl)-1H-benzo[d]imidazole-6-carboxylic acid,
37) 2-(4-(6-(4-chloro-2-fluorobenzyloxy)pyridin-2-yl)-2,6-difluorobenzyl)-1-(2-methoxyethyl)-1H-benzo[d]imidazole-6-carboxylic acid,
38) 2-(4-(6-(4-cyano-2-fluorobenzyloxy)pyridin-2-yl)-3-fluorobenzyl)-1-(2-methoxyethyl)-1H-benzo[d]imidazole-6-carboxylic acid,
39) 2-((3'-(4-chloro-2-fluorobenzyloxy)-2-fluorobiphenyl-4-yl)methyl)-1-(2-methoxyethyl)-1H-benzo[d]imidazole-6-carboxylic acid,
40) 2-((3'-(4-cyano-2-fluorobenzyloxy)-2-fluorobiphenyl-4-yl)methyl)-1-(2-methoxyethyl)-1H-benzo[d]imidazole-6-carboxylic acid,
41) (R)-2-((3'-(4-chloro-2-fluorobenzyloxy)-3-fluorobiphenyl-4-yl)methyl)-1-((tetrahydrofuran-2-yl)methyl)-1H-benzo[d]imidazole-6-carboxylic acid,
42) (R)-2-((3'-(4-chloro-2-fluorobenzyloxy)-2-fluorobiphenyl-4-yl)methyl)-1-((tetrahydrofuran-2-yl)methyl)-1H-benzo[d]imidazole-6-carboxylic acid,
43) 2-(4-(6-(4-chloro-2-fluorobenzyloxy)pyridin-2-yl)-2-fluorobenzyl)-1-(2-fluoroethyl)-1H-benzo[d]imidazole-6-carboxylic acid,
44) 2-(4-(6-(4-cyano-2-fluorobenzyloxy)pyridin-2-yl)-2-fluorobenzyl)-1-(2-fluoroethyl)-1H-benzo[d]imidazole-6-carboxylic acid,
45) (R)-2-(4-(6-((4-chloro-2-fluorophenoxy)methyl)pyridin-2-yl)-2-fluorobenzyl)-1-((tetrahydrofuran-2-yl)methyl)-1H-benzo[d]imidazole-6-carboxylic acid, 46) (R)-2-((3'-(4-cyano-2-fluorobenzyloxy)-3-fluorobiphenyl-4-yl)methyl)-1-((tetrahydrofuran-2-yl)methyl)-1H-benzo[d]imidazole-6-carboxylic acid, 47) (R)-2-((3'-(4-cyano-2-fluorobenzyloxy)-2-fluorobiphenyl-4-yl)methyl)-1-((tetrahydrofuran-2-yl)methyl)-1H-benzo[d]imidazole-6-carboxylic acid, 48) 2-((3'-(4-chloro-2-fluorobenzyloxy)-3,5-difluorobiphenyl-4-yl)methyl)-1-(2-methoxyethyl)-1H-benzo[d]imidazole-6-carboxylic acid, 49) 2-(4-(6-(4-chloro-2-fluorobenzyloxy)pyridin-2-yl)-2-fluorobenzyl)-1-(thiophen-2-ylmethyl)-1H-benzo[d]imidazole-6-carboxylic acid, 50) 2-(4-(6-(4-chloro-2-fluorobenzyloxy)pyridin-2-yl)-3-fluorobenzyl)-1-(thiophen-2-ylmethyl)-1H-benzo[d]imidazole-6-carboxylic acid, 51) (R)-2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid, 52) (R)-2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid, 53) 2-(4-(6-(4-chloro-2-fluorobenzyloxy)pyridin-2-yl)-2-methylbenzyl)-1-(2-methoxyethyl)-1H-benzo[d]imidazole-6-carboxylic acid, 54) 2-(4-(6-(4-cyano-2-fluorobenzyloxy)pyridin-2-yl)-2-methylbenzyl)-1-(2-methoxyethyl)-1H-benzo[d]imidazole-6-carboxylic acid, 55) 2-(4-(6-(4-chloro-2-fluorobenzyloxy)pyridin-2-yl)-3-fluorobenzyl)-1-(2-fluoroethyl)-1H-benzo[d]imidazole-6-carboxylic acid, 56) 2-((3'-(4-chloro-2-fluorobenzyloxy)-3-fluorobiphenyl-4-yl)methyl)-1-(2-fluoroethyl)-1H-benzo[d]imidazole-6-carboxylic acid, 57) 2-((3'-(4-cyano-2-fluorobenzyloxy)-3-fluorobiphenyl-4-yl)methyl)-1-(2-fluoroethyl)-1H-benzo[d]imidazole-6-carboxylic acid, 58) 2-(4-(6-(4-cyano-2-fluorobenzyloxy)pyridin-2-yl)-3-fluorobenzyl)-1-(2-fluoroethyl)-1H-benzo[d]imidazole-6-carboxylic acid, 59) (S)-2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid, 60) (S)-2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid, 61) 2-(4-(6-(4-chloro-2-fluorobenzyloxy)pyridin-2-yl)-2,3-difluorobenzyl)-1-((tetrahydrofuran-2-yl)methyl)-1H-benzo[d]imidazole-6-carboxylic acid, 62) 2-(4-(6-(4-cyano-2-fluorobenzyloxy)pyridin-2-yl)-2,3-difluorobenzyl)-1-((tetrahydrofuran-2-yl)methyl)-1H-benzo[d]imidazole-6-carboxylic acid, 63) 2-(4-(6-(4-chloro-2-fluorobenzyloxy)pyridin-2-yl)-2-methoxybenzyl)-1-((tetrahydrofuran-2-yl)methyl)-1H-benzo[d]imidazole-6-carboxylic acid, 64) 2-(4-(6-(4-cyano-2-fluorobenzyloxy)pyridin-2-yl)-2-methoxybenzyl)-1-((tetrahydrofuran-2-yl)methyl)-1H-benzo[d]imidazole-6-carboxylic acid, 65) 2-(4-(6-(4-chloro-2-fluorobenzyloxy)pyridin-2-yl)-2,6-difluorobenzyl)-1-((tetrahydrofuran-2-yl)methyl)-1H-benzo[d]imidazole-6-carboxylic acid, 66) (S)-2-(4-(6-(4-cyano-2-fluorobenzyloxy)pyridin-2-yl)-2-fluorobenzyl)-1-((tetrahydrofuran-2-yl)methyl)-1H-benzo[d]imidazole-6-carboxylic acid, 67) (S)-2-(4-(6-(4-cyano-2-fluorobenzyloxy)pyridin-2-yl)-3-fluorobenzyl)-1-((tetrahydrofuran-2-yl)methyl)-1H-benzo[d]imidazole-6-carboxylic acid, 68) 2-(4-(6-(4-cyano-2-fluorobenzyloxy)pyridin-2-yl)-2-methylbenzyl)-1-((tetrahydrofuran-2-yl)methyl)-1H-benzo[d]imidazole-6-carboxylic acid, 69) 2-(4-(6-(4-chloro-2-fluorobenzyloxy)pyridin-2-yl)-2-methylbenzyl)-1-((tetrahydrofuran-2-yl)methyl)-1H-benzo[d]imidazole-6-carboxylic acid, 70) 2-(4-(6-(4-chloro-2-fluorobenzyloxy)pyridin-2-yl)-2,5-difluorobenzyl)-1-((tetrahydrofuran-2-yl)methyl)-1H-benzo[d]imidazole-6-carboxylic acid, 71) 2-(4-(6-(4-cyano-2-fluorobenzyloxy)pyridin-2-yl)-2,5-difluorobenzyl)-1-((tetrahydrofuran-2-yl)methyl)-1H-benzo[d]imidazole-6-carboxylic acid, 72) 2-(4-(6-(4-chloro-2-fluorobenzyloxy)pyridin-2-yl)-2-fluorobenzyl)-1-((1-ethyl-1H-imidazol-5-yl)methyl)-1H-benzo[d]imidazole-6-carboxylic acid, 73) (S)-2-(4-(6-(4-cyano-2-fluorobenzyloxy)pyridin-2-yl)-2-fluorobenzyl)-1-(oxetan-2-ylmethyl)-1H-benzo[d]imidazole-6-carboxylic acid, 74) (S)-2-(4-(6-(4-cyano-2-fluorobenzyloxy)pyridin-2-yl)-3-fluorobenzyl)-1-(oxetan-2-ylmethyl)-1H-benzo[d]imidazole-6-carboxylic acid, 75) 2-(4-(6-(4-chlorobenzyloxy)pyridin-2-yl)-2-fluorobenzyl)-1-((tetrahydrofuran-2-yl)methyl)-1H-benzo[d]imidazole-6-carboxylic acid, 76) 2-(2-fluoro-4-(6-(4-methylbenzyloxy)pyridin-2-yl)benzyl)-1-((tetrahydrofuran-2-yl)methyl)-1H-benzo[d]imidazole-6-carboxylic acid, 77) 2-(2-fluoro-4-(6-(4-(trifluoromethyl)benzyloxy)pyridin-2-yl)benzyl)-1-((tetrahydrofuran-2-yl)methyl)-1H-benzo[d]imidazole-6-carboxylic acid, 78) (S)-2-(4-(6-(4-chloro-2-fluorobenzyloxy)pyridin-2-yl)-2-fluorobenzyl)-1-(oxetan-2-ylmethyl)-1H-benzo[d]imidazole-6-carboxylic acid, 79) (S)-2-(4-(6-(4-chloro-2-fluorobenzyloxy)pyridin-2-yl)-3-fluorobenzyl)-1-(oxetan-2-ylmethyl)-1H-benzo[d]imidazole-6-carboxylic acid, 80) 2-(2-fluoro-4-(6-(3-methylbenzyloxy)pyridin-2-yl)benzyl)-1-((tetrahydrofuran-2-yl)methyl)-1H-benzo[d]imidazole-6-carboxylic acid, 81) 2-(2-fluoro-4-(6-(3-methoxybenzyloxy)pyridin-2-yl)benzyl)-1-((tetrahydrofuran-2-yl)methyl)-1H-benzo[d]imidazole-6-carboxylic acid, 82) (S)-2-(4-(6-(4-chloro-2-fluorobenzyloxy)pyridin-2-yl)-2,3-difluorobenzyl)-1-(oxetan-2-ylmethyl)-1H-benzo[d]imidazole-6-carboxylic acid, 83) 2-(4-(6-(benzyloxy)pyridin-2-yl)-2-fluorobenzyl)-1-((tetrahydrofuran-2-yl)methyl)-1H-benzo[d]imidazole-6-carboxylic acid, 84) (S)-2-(4-(6-(4-chloro-2-fluorobenzyloxy)pyridin-2-yl)-2,6-difluorobenzyl)-1-(oxetan-2-ylmethyl)-1H-benzo[d]imidazole-6-carboxylic acid, 85) 2-(4-(6-(3,4-difluorobenzyloxy)pyridin-2-yl)-2-fluorobenzyl)-1-((tetrahydrofuran-2-yl)methyl)-1H-benzo[d]imidazole-6-carboxylic acid, 86) (S)-2-(4-(6-(4-chloro-2-fluorobenzyloxy)pyridin-2-yl)-2,5-difluorobenzyl)-1-(oxetan-2-ylmethyl)-1H-benzo[d]imidazole-6-carboxylic acid, 87) 2-(4-(6-(4-cyanobenzyloxy)pyridin-2-yl)-2-fluorobenzyl)-1-((tetrahydrofuran-2-yl)methyl)-1H-benzo[d]imidazole-6-carboxylic acid, 88) 2-(2-fluoro-4-(6-(4-nitrobenzyloxy)pyridin-2-yl)benzyl)-1-((tetrahydrofuran-2-yl)methyl)-1H-benzo[d]imidazole-6-carboxylic acid, 89) 2-(4-(6-(4-bromo-2-fluorobenzyloxy)pyridin-2-yl)-2-fluorobenzyl)-1-((tetrahydrofuran-2-yl)methyl)-1H-benzo[d]imidazole-6-carboxylic acid, 90) 2-(3-fluoro-4-(6-(3-methylbenzyloxy)pyridin-2-yl)benzyl)-1-((tetrahydrofuran-2-yl)methyl)-1H-benzo[d]imidazole-6-carboxylic acid, 91) 2-(4-(6-(4-chloro-2-fluorobenzyloxy)-5-fluoropyridin-2-yl)-2-fluorobenzyl)-1-((tetrahydrofuran-2-yl)methyl)-1H-benzo[d]imidazole-6-carboxylic acid, 92) 2-((3'-(4-chloro-2-fluorobenzyloxy)-2,4'-difluorobiphenyl-4-yl)methyl)-1-((tetrahydrofuran-2-yl)methyl)-1H-benzo[d]imidazole-6-carboxylic acid, 93) 2-((3'-(4-cyano-2-fluorobenzyloxy)-2,4'-difluorobiphenyl-4-yl)methyl)-1-((tetrahydrofuran-2-yl)methyl)-1H-benzo[d]imidazole-6-carboxylic acid, 94) 2-(4-(6-(4-chlorobenzyloxy)pyridin-2-yl)-3-fluorobenzyl)-1-((tetrahydrofuran-2-yl)methyl)-1H-benzo[d]imidazole-6-carboxylic acid, 95) 2-((3'-(4-chloro-2-fluorobenzyloxy)-3,4'-difluorobiphenyl-4-yl)methyl)-1-((tetrahydrofuran-2-yl)methyl)-1H-benzo[d]imidazole-6-carboxylic acid, 96) 2-((3'-(4-cyano-2-fluorobenzyloxy)-3,4'-difluorobiphenyl-4-yl)methyl)-1-((tetrahydrofuran-2-yl)methyl)-1H-benzo[d]imidazole-6-carboxylic acid, 97) 2-(3-fluoro-4-(6-(4-(trifluoromethyl)benzyloxy)pyridin-2-yl)benzyl)-1-((tetrahydrofuran-2-yl)methyl)-1H-benzo[d]imidazole-6-carboxylic acid, 98) 2-(4-(6-(3,4-difluorobenzyloxy)pyridin-2-yl)-3-fluorobenzyl)-1-((tetrahydrofuran-2-yl)methyl)-1H-benzo[d]imidazole-6-carboxylic acid, 99) 2-(4-(6-(4-chloro-3-fluorobenzyloxy)pyridin-2-yl)-3-fluorobenzyl)-1-((tetrahydrofuran-2-yl)methyl)-1H-benzo[d]imidazole-6-carboxylic acid, 100) 2-(4-(6-(3-chloro-5-fluorobenzyloxy)pyridin-2-yl)-3-fluorobenzyl)-1-((tetrahydrofuran-2-yl)methyl)-1H-benzo[d]imidazole-6-carboxylic acid, 101) 2-(4-(6-(2-chloro-6-fluorobenzyloxy)pyridin-2-yl)-3-fluorobenzyl)-1-((tetrahydrofuran-2-yl)methyl)-1H-benzo[d]imidazole-6-carboxylic acid, 102) 2-((5-(3-(4-chloro-2-fluorobenzyloxy)-4-fluorophenyl)pyridin-2-yl)methyl)-1-((tetrahydrofuran-2-yl)methyl)-1H-benzo[d]imidazole-6-carboxylic acid, 103) (S)-2-(4-(6-(4-cyano-2-fluorobenzyloxy)pyridin-2-yl)-2,6-difluorobenzyl)-1-(oxetan-2-ylmethyl)-1H-benzo[d]imidazole-6-carboxylic acid, 104) 2-((4-(3-(4-cyano-2-fluorobenzyloxy)phenyl)-2-oxopyridin-1(2H)-yl)methyl)-1-(2-methoxyethyl)-1H-benzo[d]imidazole-6-carboxylic acid, 105) 2-((4-(6-(4-chloro-2-fluorobenzyloxy)pyridin-2-yl)-2-oxopyridin-1(2H)-yl)methyl)-1-((tetrahydrofuran-2-yl)methyl)-1H-benzo[d]imidazole-6-carboxylic acid, 106) 2-((4-(3-(4-chloro-2-fluorobenzyloxy)phenyl)-2-oxopyridin-1(2H)-yl)methyl)-1-((tetrahydrofuran-2-yl)methyl)-1H-benzo[d]imidazole-6-carboxylic acid, 107) 2-((4-(3-(4-cyano-2-fluorobenzyloxy)phenyl)-2-oxopyridin-1(2H)-yl)methyl)-1-((tetrahydrofuran-2-yl)methyl)-1H-benzo[d]imidazole-6-carboxylic acid, 108) (S)-2-((4-(6-(4-chloro-2-fluorobenzyloxy)pyridin-2-yl)-2-oxopyridin-1(2H)-yl)methyl)-1-((tetrahydrofuran-2-yl)methyl)-1H-benzo[d]imidazole-6-carboxylic acid, 109) (S)-2-((4-(6-(4-cyano-2-fluorobenzyloxy)pyridin-2-yl)-2-oxopyridin-1(2H)-yl)methyl)-1-((tetrahydrofuran-2-yl)methyl)-1H-benzo[d]imidazole-6-carboxylic acid, 110) (S)-2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid, 111) (S)-2-((4-(6-(4-cyano-2-fluorobenzyloxy)pyridin-2-yl)-2-oxopyridin-1(2H)-yl)methyl)-1-(oxetan-2-ylmethyl)-1H-benzo[d]imidazole-6-carboxylic acid, 112) 2-((4-(6-(4-chloro-2-fluorobenzyloxy)pyridin-2-yl)-6-oxopyrimidin-1(6H)-yl)methyl)-1-((tetrahydrofuran-2-yl)methyl)-1H-benzo[d]imidazole-6-carboxylic acid, 113) (S)-2-(4-(6-((4-cyano-2-fluorobenzyl)oxy)pyridin-2-yl)-2,3-difluorobenzyl)-1-(oxetan-2-ylmethyl)-1H-benzo[d]imidazole-6-carboxylic acid, 114) 2-(4-(6-((4-cyano-2-fluorobenzyl)oxy)pyridin-2-yl)-3-fluorobenzyl)-1-(oxetan-2-ylmethyl)-1H-benzo[d]imidazole-6-carboxylic acid, 115) (S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid, 116) (S)-2-(4-(6-((4-chloro-2-fluorobenzyl)oxy)pyridin-2-yl)-2,5-difluorobenzyl)-1-((tetrahydrofuran-2-yl)methyl)-1H-benzo[d]imidazole-6-carboxylic acid, 117) (S)-2-(4-(6-((4-chloro-2-fluorobenzyl)oxy)-5-fluoropyridin-2-yl)-3-fluorobenzyl)-1-(oxetan-2-ylmethyl)-1H-benzo[d]imidazole-6-carboxylic acid, 118) (S)-2-(4-(6-((4-cyanobenzyl)oxy)pyridin-2-yl)-3-fluorobenzyl)-1-(oxetan-2-ylmethyl)-1H-benzo[d]imidazole-6-carboxylic acid, 119) (S)-2-(4-(6-((2,4-difluorobenzyl)oxy)pyridin-2-yl)-3-fluorobenzyl)-1-(oxetan-2-ylmethyl)-1H-benzo[d]imidazole-6-carboxylic acid, 120) (S)-2-(4-(6-((4-cyano-2-fluorobenzyl)oxy)pyridin-2-yl)-2,5-difluorobenzyl)-1-((tetrahydrofuran-2-yl)methyl)-1H-benzo[d]imidazole-6-carboxylic acid, 121) (S)-2-(3-fluoro-4-(6-((4-(trifluoromethyl)benzyl)oxy)pyridin-2-yl)benzyl)-1-(oxetan-2-ylmethyl)-1H-benzo[d]imidazole-6-carboxylic acid, 122) (S)-2-(3-fluoro-4-(6-((4-methoxybenzyl)oxy)pyridin-2-yl)benzyl)-1-(oxetan-2-ylmethyl)-1H-benzo[d]imidazole-6-carboxylic acid, 123) (S)-2-(4-(6-((4-chlorobenzyl)oxy)pyridin-2-yl)-3-fluorobenzyl)-1-(oxetan-2-ylmethyl)-1H-benzo[d]imidazole-6-carboxylic acid, 124) (S)-2-(3-fluoro-4-(6-((4-nitrobenzyl)oxy)pyridin-2-yl)benzyl)-1-(oxetan-2-ylmethyl)-1H-benzo[d]imidazole-6-carboxylic acid, 125) (S)-2-(4-(6-((3,4-difluorobenzyl)oxy)pyridin-2-yl)-3-fluorobenzyl)-1-(oxetan-2-ylmethyl)-1H-benzo[d]imidazole-6-carboxylic acid, 126) (S)-2-(4-(6-((2-chloro-6-fluorobenzyl)oxy)pyridin-2-yl)-3-fluorobenzyl)-1-(oxetan-2-ylmethyl)-1H-benzo[d]imidazole-6-carboxylic acid, 127) 2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid, 128) (S)-2-(3-fluoro-4-(6-(pyridin-4-ylmethoxy)pyridin-2-yl)benzyl)-1-(oxetan-2-ylmethyl)-1H-benzo[d]imidazole-6-carboxylic acid, 129) (S)-2-(3-fluoro-4-(6-(pyridin-3-ylmethoxy)pyridin-2-yl)benzyl)-1-(oxetan-2-ylmethyl)-1H-benzo[d]imidazole-6-carboxylic acid, 130) 2-(4-(6-((4-cyano-2-fluorobenzyl)oxy)pyridin-2-yl)-3-fluorobenzyl)-1-((tetrahydrofuran-2-yl)methyl)-1H-benzo[d]imidazole-6-carboxylic acid, 131) (S)-2-((4-(6-((4-chloro-2-fluorobenzyl)oxy)pyridin-2-yl)-1H-pyrazol-1-yl)methyl)-1-(oxetan-2-ylmethyl)-1H-benzo[d]imidazole-6-carboxylic acid, 132) (S)-2-(4-(6-(benzo[d]thiazol-2-ylmethoxy)pyridin-2-yl)-3-fluorobenzyl)-1-(oxetan-2-ylmethyl)-1H-benzo[d]imidazole-6-carboxylic acid, 133) (S)-2-(4-(6-((4-cyano-2-fluorobenzyl)oxy)pyridin-2-yl)-2-methylbenzyl)-1-(oxetan-2-ylmethyl)-1H-benzo[d]imidazole-6-carboxylic acid, 134) (S)-2-(4-(6-((4-chloro-2-fluorobenzyl)oxy)pyridin-2-yl)-2-methylbenzyl)-1-(oxetan-2-ylmethyl)-1H-benzo[d]imidazole-6-carboxylic acid, and 135) (S)-2-(4-(6-(cyclopropylmethoxy)pyridin-2-yl)-3-fluorobenzyl)-1-(oxetan-2-ylmethyl)-1H-benzo[d]imidazole-6-carboxylic acid.

As used herein, "$C_{1-5}$ alkyl" means a linear or branched, saturated hydrocarbon group having 1 to 5 carbon atoms. For example, a $C_{1-5}$ alkyl group includes, but is not limited to, methyl, ethyl, propyl, butyl, pentyl, 1-methylethyl, 1-methylpropyl, 2-methylpropyl, 1,1-dimethylethyl, 1-methylbutyl, and 1,1-dimethylpropyl.

The term "$C_{1-5}$ alkoxy" is an OR group, wherein R is a $C_{1-5}$ alkyl group as defined above. Examples of an alkoxy group having 1 to 5 carbon atoms include, although not limited to, methoxy, ethoxy, propoxy, butoxy, 1-methylethoxy, 1,1-dimethylethoxy, 1-methylpropoxy, 2-methylpropoxy, or cyclopropylmethoxy.

The term "$C_{1-5}$ haloalkyl" is a $C_{1-5}$ alkyl group as defined above in which one or more hydrogen atoms are replaced by one or more halo atoms. Examples thereof include, although not limited to, a difluoromethyl or trifluoromethyl group.

As used herein, "halo" is fluoro, chloro, or bromo.

The term "$C_{3-7}$ cycloalkyl" means a saturated hydrocarbon ring system having 3 to 7 ring carbon atoms. Examples thereof include, although not limited to, cyclopropyl, cyclobutyl, cyclopentyl, cyclohexyl or cycloheptyl.

The term "aryl" refers to a $C_{6-10}$ aromatic group which may be substituted or unsubstituted, preferably a $C_6$ aryl group (i.e., phenyl).

The term "heteroaryl" refers to an aromatic ring system containing one or more heteroatoms selected from N, O, and S, and preferably refers to a 5- or 6-membered monocyclic aromatic ring system. Examples of the 5- or 6-membered heteroaryl include, but are not limited to, pyrrolyl, thiophenyl, furanyl, pyrazolyl, thiazolyl, isothiazolyl, oxazolyl, imidazolyl, isoxazolyl, triazolyl, thiadiazolyl, tetrazolyl, oxadiazolyl, pyridinyl, pyrazinyl, pyridazinyl, pyrimidinyl, triazinyl, and the like.

The term "fused heteroaryl" refers to a ring system in which the heteroaryl group is linked with another aryl, heteroaryl, or heterocycloalkyl group in a fused way, and is preferably a 9- or 10-membered benzo-fused heteroaryl group. Examples of the fused heteroaryl include, but are not limited to, benzofuranyl, isobenzofuranyl, benzothiophenyl, indolyl, isoindolyl, indazolyl, benzimidazolyl, benzoxazolyl, benzisoxazolyl, benzthiazolyl, benzthiadiazolyl, benzoxadiazolyl, benztriazolyl, quinolinyl, isoquinolinyl, quinazolinyl, and the like.

The term "heterocycloalkyl" refers to a saturated or partially unsaturated ring system containing one or more heteroatoms selected from N, O, and S, and is preferably 4-, 5- or 6-membered heterocycloalkyl. Examples of the heterocycloalkyl include, but are not limited to, oxiranyl, aziridinyl, azetidinyl, oxetanyl, tetrahydrofuranyl, tetrahydrothiophenyl, pyrrolidinyl, 3-pyrrolinyl, 2-pyrrolinyl, 2H-pyrrolyl, 1H-pyrrolyl, imidazolidinyl, 2-imidazolinyl, pyrazolidinyl, 2-pyrazolinyl, oxazolidinyl, isoxazolidinyl, isothiazolidinyl, thiazolidinyl, oxadiazolidinyl, thiadiazolidinyl, tetrahydropyranyl, 2H-pyranyl, 4H-pyranyl, piperidinyl, morpholinyl, thianyl, 2H-thiopyranyl, 4H-thiopyranyl, dithianyl, thiomorpholinyl, piperazinyl, trithianyl, dioxolanyl, oxathiolanyl, 1,4-dioxanyl, oxazinyl, thiazinyl, and the like.

Further, a compound of the present invention may exist in the form of a salt, particularly a pharmaceutically acceptable salt. Preferably, the pharmaceutically acceptable salt is a metal salt, more preferably a salt of sodium, potassium, cesium, lithium, magnesium, or calcium. The metal salt may be prepared using an inorganic base or an organic base. For example, the compound represented by Formula 1 is dissolved in a water-miscible organic solvent, such as acetone, methanol, ethanol, or acetonitrile, thereafter an organic base or an inorganic base is added thereto, and then precipitated crystals are prepared through filtration, and dried, thereby obtaining a pharmaceutically acceptable salt. Alternatively, the pharmaceutically acceptable salt may be prepared by vacuuming the solvent from a reaction mixture with a base added thereinto, followed by drying the residue, or by adding another organic solvent and filtering the precipitated salt. In addition, the corresponding salt is obtained by reacting an alkali metal or alkaline earth metal salt with a suitable silver salt (e.g., silver nitrate).

Further, the salt may be prepared using various organic bases as well as metal salts, and typically, tris salts may be prepared using tris(hydroxymethyl)aminomethane. In addition, a pharmaceutically acceptable salt may be prepared using a basic amino acid. As the amino acid salt, it is pharmaceutically suitable to prepare a natural amino acid salt such as arginine, histamine, and lysine.

Meanwhile, a pharmaceutically unacceptable salt or solvate of the compound represented by Formula 1 may be used as an intermediate in the preparation of the compound represented by Formula 1, or a pharmaceutically acceptable salt or solvate thereof.

The compound represented by Formula 1 of the present invention includes not only a pharmaceutically acceptable salt thereof, but also all possible solvates and hydrates that may be prepared therefrom, and includes all possible stereoisomers as well. Solvates, hydrates, and stereoisomers of the compound represented by Formula 1 may be prepared and used from the compound represented by Formula 1 using conventional methods.

In addition, the compound represented by Formula 1 according to the present invention may be prepared in a crystalline or amorphous form. The compound represented by Formula 1 may be optionally hydrated or solvated when prepared in a crystalline form. The present invention may include stoichiometric hydrates of the compounds represented by Formula 1 as well as compounds containing various amounts of water. Solvates of the compound represented by Formula 1 according to the present invention include both stoichiometric solvates and non-stoichiometric solvates.

In addition, as an embodiment, the compound represented by Formula 1 may be prepared using a preparation method as shown in Reaction Scheme 1 below.

[Reaction Scheme 1]

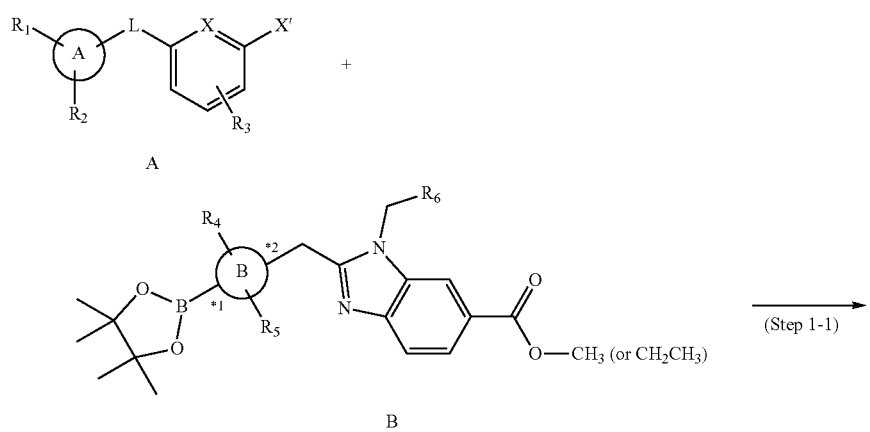

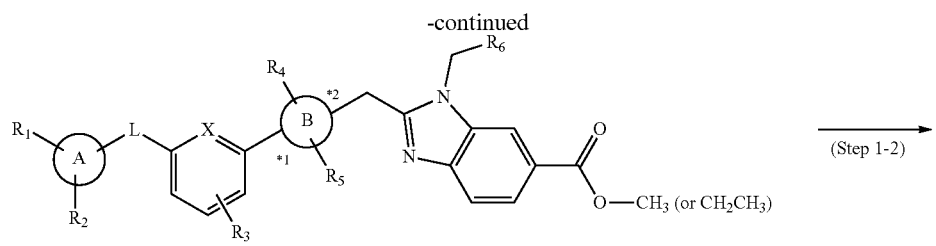

C

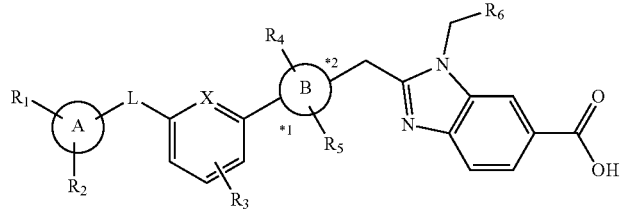

1

In Reaction Scheme 1, the definitions other than X' are as defined above, and X' is halogen, preferably chloro or bromo.

Step 1-1 is a Suzuki coupling reaction, in which a compound represented by Formula C is prepared by reacting a compound represented by Formula A with a compound represented by Formula B. It is preferable to carry out the reaction in the presence of a palladium catalyst and a base, and a reactor for the Suzuki coupling reaction may be modified in accordance with the common knowledge in the art.

Step 1-2 is a hydrolysis reaction, in which a methyl ester group (or ethyl ester group) is converted into a carboxyl group. It is preferable to carry out the reaction in the presence of a base, and the reaction conditions for the hydrolysis reaction can be applied in accordance with the common knowledge in the art.

The preparation method of Reaction Scheme 1 may be more specified in Examples to be described later.

In addition, as an embodiment, a compound represented by Formula 1 may be prepared using a preparation method shown in Reaction Scheme 2 below.

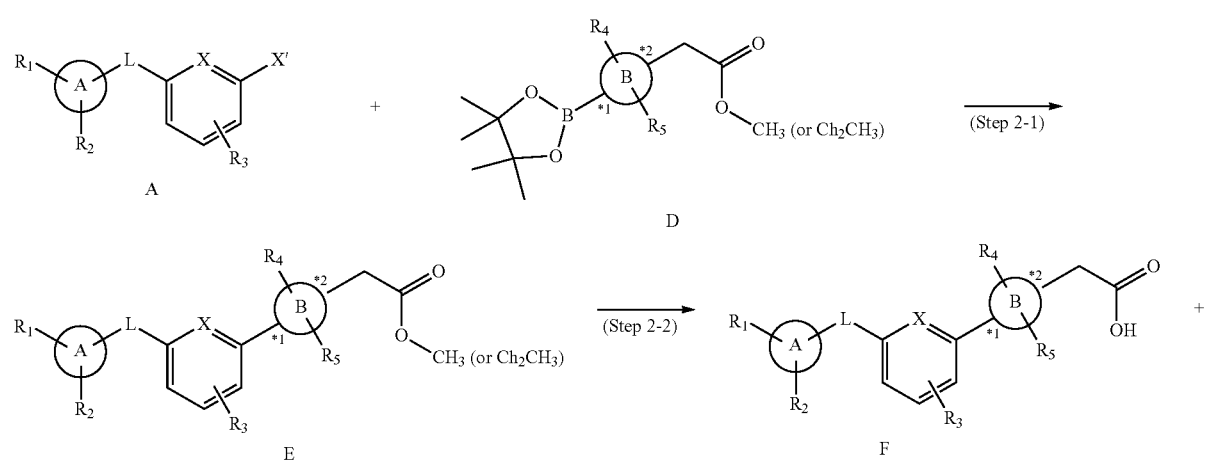

-continued

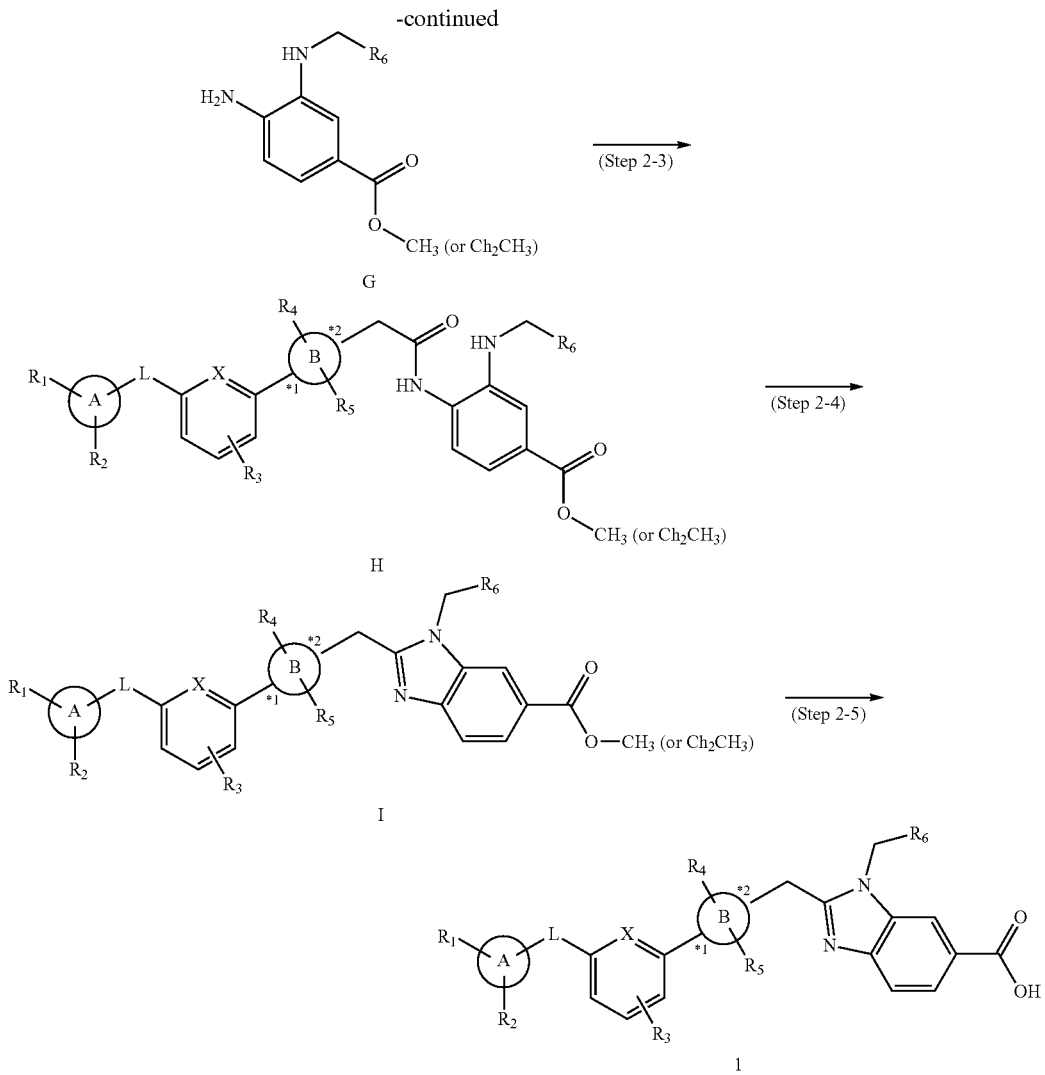

In Reaction Scheme 2, the definitions other than X' are as defined above, and X' is halogen, preferably chloro or bromo.

Step 2-1 is a Suzuki coupling reaction, in which a compound represented by Formula E is prepared by reacting a compound represented by Formula A with a compound represented by Formula D. It is preferable to carry out the reaction in the presence of a palladium catalyst and a base, and a reactor for the Suzuki coupling reaction may be modified in accordance with the common knowledge in the art.

Step 2-2 is a hydrolysis reaction, in which a methyl ester group (or ethyl ester group) is converted into a carboxyl group. The reaction is preferably carried out in the presence of a base, and the reaction conditions for the hydrolysis reaction can be applied in accordance with the common knowledge in the art.

Step 2-3 is an amidation reaction, in which a compound represented by Formula H is prepared by reacting a compound represented by Formula F with a compound represented by Formula D. The reaction conditions for the amidation reaction can be applied in accordance with the common knowledge in the art.

Step 2-4 is a cyclization reaction, in which a compound represented by Formula H is reacted under acidic conditions to form a benzoimidazole ring. The reaction conditions for the cyclization reaction can be applied in accordance with the common knowledge in the art.

Step 2-5 is a hydrolysis reaction, in which a methyl ester group (or ethyl ester group) is converted into a carboxyl group. It is preferable to carry out the reaction in the presence of a base, and the reaction conditions for the hydrolysis reaction can be applied in accordance with the common knowledge in the art.

The preparation method of Reaction Scheme 2 may be more specified in Examples to be described later.

In addition, the present invention provides a pharmaceutical composition for preventing or treating a disease associated with GLP-1 activity, which contains, as an active ingredient, a compound represented by Formula 1, or a pharmaceutically acceptable salt, hydrate, solvate or isomer thereof.

That is, the compound represented by Formula 1, or a pharmaceutically acceptable salt, hydrate, solvate, or isomer thereof, which is a GLP-1 receptor agonist, induces effects such as stimulation of insulin secretion, inhibition of glucagon secretion, inhibition of gastric fasting, inhibition of gastric motility or intestinal motility, and induction of weight loss, and may thus be usefully used for preventing or treating a disease associated with GLP-1 activity.

Examples of the disease associated with GLP-1 activity include diabetes, hyperglycemia, insulin resistance, impaired glucose tolerance, diabetic neuropathy, diabetic nephropathy, obesity, glucose metabolism disorder, hyperlipidemia, dyslipidemia, cardiovascular disease, arteriosclerosis, non-alcoholic fatty liver disease, or non-alcoholic steatohepatitis.

As used herein, the term "prevention" means any action that inhibits or delays the development, spread, and recurrence of the disease by administration of the pharmaceutical composition of the present invention, and as used herein, the term "treatment" means any action that alleviates or advantageously alters the symptoms of the disease by administration of the pharmaceutical composition of the present invention.

The pharmaceutical composition of the present invention may be formulated in oral or parenteral dosage form according to the standard pharmaceutical practice. These formulations may contain additives such as a pharmaceutically acceptable carrier, an adjuvant, or a diluent, in addition to the active ingredient.

The carrier suitably includes, although not limited to, for example, physiological saline, polyethylene glycol, ethanol, vegetable oil and isopropylmyristate and the like, and the diluent suitably includes, although not limited to, lactose, dextrose, sucrose, mannitol, sorbitol, cellulose and/or glycine, etc. In addition, the compounds of the present invention can be dissolved in oil, propylene glycol, or other solvents commonly used in the preparation of injectable solutions. Further, the compounds of the present invention may be formulated as ointments or creams for topical effects.

The pharmaceutical dosage form of the compounds according to the present invention may be used in the form of a pharmaceutically acceptable salt or solvate thereof, and may also be used alone or in combination with other pharmaceutically active compounds, as well as in a suitable set.

The compounds of the present invention may be dissolved, suspended or emulsified in a general saline, a water-soluble solvent such as 5% dextrose, or a non-water-soluble solvent such as synthetic fatty acid glyceride, higher fatty acid ester or propylene glycol to be formulated as an injection. The formulation of the present invention may include conventional additives such as solubilizers, isotonic agents, suspending agents, emulsifiers, stabilizers, and preservatives.

The preferred dosage of the compound according to the present invention varies depending on the condition and weight of the patient, the extent of the disease, the form of the therapeutic agent, the route and duration of administration, but may be appropriately selected by those skilled in the art. However, for a desirable effect, the compound of the present invention may be administered at 0.0001 to 100 mg/kg (body weight), preferably 0.001 to 100 mg/kg (body weight) per day. The compound may be administered once a day or in divided doses via an oral or parenteral route. Depending on administration methods, the composition may contain 0.001 to 99 wt. %, preferably 0.01 to 60 wt. % of the compound of the present invention.

The pharmaceutical composition of the present invention may be administered to mammals including rats, mice, livestock, and humans by various routes. All administration methods can be envisaged, and the composition may be administered, for example, by oral, rectal or intravenous, intramuscular, subcutaneous, intrauterine dural or intracerebroventricular injection.

Advantageous Effects of Invention

A compound according to the present invention, or a pharmaceutically acceptable salt thereof, may be usefully used as a GLP-1 receptor agonist for preventing or treating a disease associated with GLP-1 activity.

MODE FOR THE INVENTION

Hereinafter, the following examples are presented in order to demonstrate the present invention in detail. However, the following examples are provided only to illustrate the present invention, and the scope of the present invention is not limited by the following examples.

Example 7: Preparation of 2-(4-(6-((4-chloro-2-fluorophenoxy)methyl)pyridin-2-yl)-2-nitrobenzyl)-1-(2-methoxyethyl)-1H-benzo[d]imidazole-6-carboxylic acid Step 1) Preparation of 2-chloro-6-((4-chloro-2-fluorophenoxy)methyl)pyridine

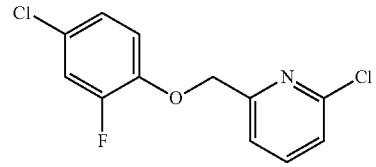 [SMILES: Fc1cc(Cl)ccc1OCc1cccc(Cl)n1]

To a 250 mL 2-neck flask, 4-chloro-2-fluorophenol (5.7 g, 26.00 mmol) and dimethylformamide (60 mL) were added, stirred for 5 minutes to dissolve, and then (6-chloropyridin-2-yl)methyl methanesulfonate (3.47 g, 23.60 mmol) and cesium carbonate (15.42 g, 47.30 mmol) were added, followed by stirring for 2 hours at room temperature. After completion of the reaction, distilled water (100 mL) was added to the flask containing the resultant mixture to form a solid compound. The resultant was filtered under reduced pressure and dried, thereby obtaining a target compound (6.27 g, 23.00 mmol, yield: 97.3%).

$^1$H NMR (400 MHz, CDCl$_3$) δ 7.72-7.68 (t, 1H), 7.50-7.48 (d, 1H), 7.29-7.27 (d, 1H), 7.15-7.12 (dd, 1H), 7.05-7.01 (dt, 1H), 6.92-6.88 (t, 1H), 5.20 (s, 2H)

Step 2) Preparation of methyl 2-(4-(6-((4-chloro-2-fluorophenoxy)methyl)pyridin-2-yl)-2-nitrobenzyl)-1-(2-methoxyethyl-1H-benzo[d]imidazole-6-carboxylate

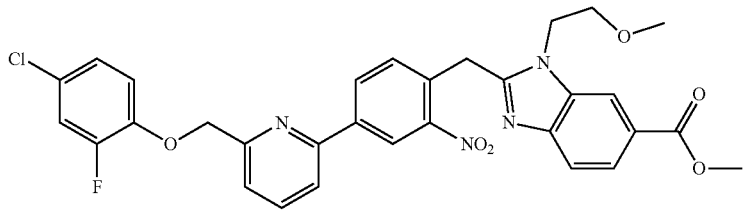 [SMILES: COCCn1c(Cc2ccc(-c3cccc(COc4ccc(Cl)cc4F)n3)cc2[N+](=O)[O-])nc2ccc(C(=O)OC)cc21]

To a 250 mL 3-neck flask, 2-chloro-6-((4-chloro-2-fluorophenoxy)methyl)pyridine (3.53 g, 13.00 mmol) prepared in step 1 and tetrahydrofuran:ethanol:distilled water (4:2:1 (volume ratio); 20 mL, 10 mL, 5 mL; total 35 mL) were added and stirred for 5 minutes to dissolve. Then, methyl 1-(2-methoxyethyl)-2-(2-nitro-4-(4,4,5,5-tetramethyl-1,3,2-dioxaborolan-2-yl)-1H-benzo[d]imidazole-6-carboxylate (5.69 g, 11.82 mmol), tripotassium phosphate (7.52 g, 35.4 mmol), and Pd(dppf)Cl$_2$·CH$_2$Cl$_2$ (0.96 g, 1.18 mmol) were added, slowly heated up to 80° C., and stirred for 2 hours using a reflux cooler. After completion of the reaction, the resultant mixture was cooled to room temperature for 30 minutes. Then, the reaction mixture was concentrated under reduced pressure, and extracted with ethyl acetate (40 mL) and distilled water (20 mL) to separate an organic layer. After separation, the organic layer was dried over anhydrous magnesium sulfate and concentrated under reduced pressure to remove the solvent. Thereafter, separation was performed using column chromatography under the condition of ethyl acetate:n-hexane (1:5 (volume ratio)). The resulting compound was concentrated under reduced pressure, thereby obtaining a target compound (0.158 g, 0.26 mmol, yield: 22.09%).

$^1$H NMR (400 MHz, CDCl$_3$) δ 8.87 (s, 1H), 8.44-8.39 (dd, 2H), 8.10 (s, 1H), 7.95-7.94 (d, 1H), 7.92-7.87 (t, 1H), 7.78-7.68 (d, 1H), 7.59-7.57 (d, 1H), 7.16-7.00 (t, 2H), 6.78 (s, 1H), 5.34 (s, 2H), 4.99 (s, 1H), 4.86-4.82 (m, 1H), 4.66-4.62 (d, 1H), 3.95-3.88 (d, 5H), 3.43 (s, 3H), 3.25 (s, 3H)

Step 3) Preparation of 2-(4-(6-((4-chloro-2-fluorophenoxy)methyl)pyridin-2-yl)-2-nitrobenzyl)-1-(2-meth oxyethyl)-1H-benzo[d]imidazole-6-carboxylic acid

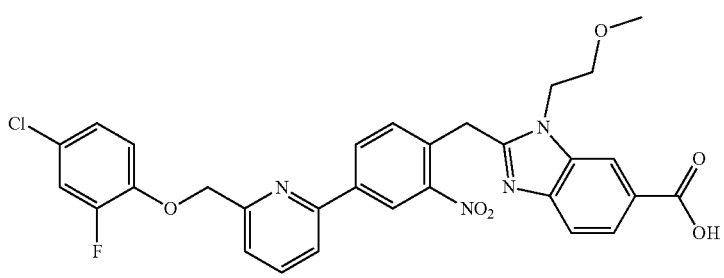 [SMILES: COCCn1c(Cc2ccc(-c3cccc(COc4ccc(Cl)cc4F)n3)cc2[N+](=O)[O-])nc2ccc(C(=O)O)cc21]

To a 100 mL 1-neck flask, methyl 2-(4-(6-((4-chloro-2-fluorophenoxy)methyl)pyridin-2-yl)-2-nitrobenzyl)-1-(2-methoxy ethyl-1H-benzo[d]imidazole-6-carboxylate (3.4 g, 5.61 mmol) prepared in step 2 and tetrahydrofuran:methanol:distilled water (4:2:1 (volume ratio)); 20 mL, 10 mL, 5 mL; total 35 mL) were added, stirred for 10 minutes to dissolve. Then, 2 N potassium hydroxide aqueous solution (20 mL) was added, followed by stirring for 4 hours at room temperature. After completion of the reaction, the mixed solution was concentrated under reduced pressure) 2 N hydrochloric acid aqueous solution (10 mL) was added and neutralized to a pH of 7-8 to produce a solid compound. The resultant was filtered under reduced pressure and dried, thereby obtaining a target compound (2.7 g, 4.56 mmol, yield: 81.3%).

$^1$H NMR (400 MHz, DMSO) δ 8.91-8.90 (d, 1H), 8.69-8.65 (m, 1H), 8.40 (s, 1H), 8.25-8.23 (d, 1H), 8.12-8.10 (t, 1H), 8.03-7.98 (d, 1H), 7.96-7.88 (d, 1H), 7.77-7.71 (t, 1H), 7.65-7.63 (d, 1H), 7.51-7.48 (dd, 1H), 7.40-7.34 (t, 1H), 7.25-7.22 (m, 1H), 5.44-5.38 (d, 2H), 3.87-3.84 (t, 2H), 3.44-3.31 (s, 2H), 3.25 (s, 3H)

Example 60: Preparation of (S)-2-(4-(6-((4-chloro-2-fluorobenzyl)oxy)pyridin-2-yl)-3-fluorobenzyl)-1-((tetrahydrofuran-2-yl)methyl)-1H-benzo[d]imidazole-6-carboxylic acid Step 1) Preparation of 2-bromo-6-((4-chloro-2-fluorobenzyl)oxy)pyridine

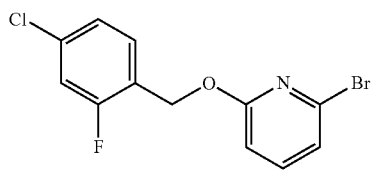 [SMILES: Fc1cc(Cl)ccc1COc1cccc(Br)n1]

To a 250 mL flask, 6-bromopyridin-2-ol (5 g, 28.73 mmol) was added and dissolved by adding dimethylformamide (25 mL). Cesium carbonate (18.40 g, 56.46 mmol) was added and then 1-(bromomethyl)-4-chloro-2-fluorobenzene (7.70 g, 34.48 mmol) was added, followed by stirring for 2 hours at room temperature. When the reaction was completed, distilled water (100 mL) was added and stirred for 30 minutes, and then the resulting solid was filtered, thereby obtaining a target compound (8.6 g, yield: 94%).

$^1$H NMR (400 MHz, CDCl$_3$) δ 8.13-8.09 (m, 1H), 7.97-7.94 (m, 2H), 4.01 (s, 3H)

Step 2) Preparation of methyl 2-(4-(6-((4-chloro-2-fluorobenzyl)oxy)pyridin-2-yl)-3-fluorophenyl)acetate

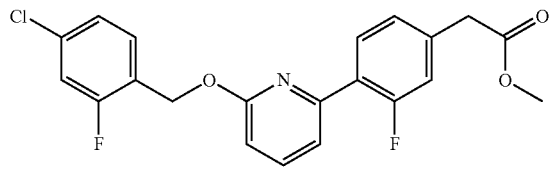 [SMILES: COC(=O)Cc1ccc(-c2cccc(OCc3ccc(Cl)cc3F)n2)c(F)c1]

To a 250 mL flask, 2-bromo-6-((4-chloro-2-fluorobenzyl)oxy)pyridine (5 g, 15.80 mmol) prepared in step 1, methyl 2-(3-fluoro-4-(4,4,5,5-tetramethyl-1,3,2-dioxaborolan-2-yl)phenyl)acetate (5.58 g, 18.95 mmol), Pd(dppf)Cl$_2$·CH$_2$Cl$_2$ (645 mg, 0.79 mmol), and tripotassium phosphate (6.70 g, 31.6 mmol) were added in order, dissolved in methanol (35 mL), tetrahydrofuran (25 mL), and distilled water (15 mL), and stirred for 2 hours using a reflux cooler. When the reaction was completed, the reaction product was concentrated under reduced pressure, and then distilled water (30 mL) was added, followed by extraction with ethyl acetate (50 mL). The extracted organic layer was dried over anhydrous magnesium sulfate and filtered under reduced pressure. The filtered solution was concentrated under reduced pressure, and then separated by a column, thereby obtaining a target compound (4.7 g, yield: 73%).

$^1$H NMR (400 MHz, CDCl$_3$) δ 8.03-7.97 (t, 1H), 7.67-7.62 (t, 1H), 7.48-7.44 (m, 2H), 7.18-7.09 (m, 4H), 6.77-6.75 (d, 1H), 5.50 (s, 2H), 4.21-4.15 (m, 2H), 3.65 (s, 2H), 1.34-1.24 (m, 3H)

Step 3) Preparation of methyl 2-(4-(6-((4-chloro-2-fluorobenzyl)oxy)pyridin-2-yl)-3-fluorophenyl)acetic acid

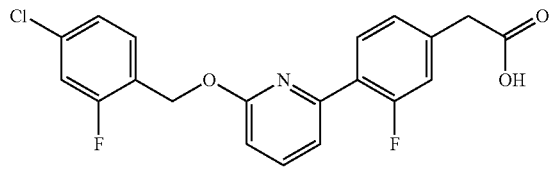 [SMILES: O=C(O)Cc1ccc(-c2cccc(OCc3ccc(Cl)cc3F)n2)c(F)c1]

In a 100 mL flask, methyl 2-(4-(6-((4-chloro-2-fluorobenzyl)oxy)pyridin-2-yl)-3-fluorophenyl)acetate (3 g, 7.43 mmol) prepared in step 2 was dissolved in methanol (15 mL) and distilled water (15 mL), and then 2 N potassium hydroxide aqueous solution (3 mL) was added, followed by stirring for 8 hours at room temperature. When the reaction was completed, the reaction product was concentrated under reduced pressure, and then 1 N hydrochloric acid aqueous solution (8 mL) was added, followed by extraction with distilled water (20 mL) and ethyl acetate (30 mL). The extracted organic layer was dried over anhydrous magnesium sulfate and filtered under reduced pressure. The filtered solution was concentrated under reduced pressure, and the resulting solid was filtered with n-hexane solution, thereby obtaining a target compound (2.78 g, yield: 96%).

$^1$H NMR (400 MHz, CDCl$_3$) δ 8.00 (t, 1H), 7.66 (t, 1H), 7.48-7.44 (m, 2H), 7.19 (d, 1H), 7.14-7.10 (m, 3H), 6.75 (d, 1H), 5.49 (s, 2H), 3.71 (s, 2H)

Step 4) Preparation of (S)-methyl 4-(2-(2-(6-((4-chloro-2-fluorobenzyl)oxy)pyridin-2-yl)-3-fluorophenyl)acetamido)-3-(((tetrahydrofuran-2-yl)methyl)amino)benzoate

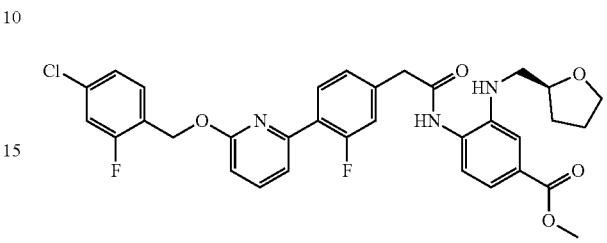

To a 100 mL flask, (S)-methyl-4-amino-3-(((tetrahydrofuran-2-yl)methyl)amino)benzoate (3 g, 11.99 mmol), methyl 2-(4-(6-((4-chloro-2-fluorobenzyl)oxy)pyridin-2-yl)-3-fluorophenyl)acetic acid (5.61 g, 14.38 mmol) prepared in step 3, 1-(3-dimethylaminopropyl)-3-ethylcarbodiimide hydrochloride (4.60 g, 23.98 mmol), and dimethylaminopyridine (2.94 g, 23.98 mmol) were added in order, and then dissolved in dichloromethane (30 mL), followed by stirring at room temperature for 5 hours. When the reaction was completed, 1 N hydrochloric acid aqueous solution (10 mL) was added, followed by extraction with distilled water (20 mL) and dichloromethane (30 mL). The extracted organic layer was dried over anhydrous magnesium sulfate and filtered under reduced pressure. The filtered solution was concentrated under reduced pressure, ethyl acetate (10 mL) was added and then n-hexane (30 mL) was added, followed by stirring for 30 minutes. The resulting solid was filtered with n-hexane solution, thereby obtaining a target compound (4.13 g, yield: 55%).

$^1$H NMR (400 MHz, CDCl$_3$) δ 8.12-8.08 (t, 1H), 7.80-7.78 (d, 1H), 7.69-7.67 (m, 2H), 7.65-7.44 (m, 4H), 7.28-7.26 (d, 1H), 7.18-7.13 (m, 3H), 6.79-6.77 (d, 1H), 5.49 (s, 2H), 3.99-3.97 (m, 1H), 3.87 (s, 3H), 3.84-3.82 (m, 3H), 3.80-3.78 (m, 1H), 3.08-2.97 (m, 2H), 1.86-1.54 (m, 4H)

Step 5) Preparation of (S)-methyl 2-(4-(6-((4-chloro-2-fluorobenzyl)oxy)pyridin-2-yl)-3-fluorobenzyl)-1-((tetrahydrofuran-2-yl)methyl)-1H-benzo[d]imidazole-6-carboxylate

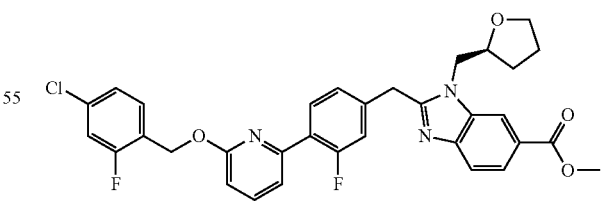

To a 100 mL flask, (S)-methyl 4-(2-(2-(6-((4-chloro-2-fluorobenzyl)oxy)pyridin-2-yl)-3-fluorophenyl)acetamido)-3-(((tetrahydrofuran-2-yl)methyl)amino)benzoate (3 g, 4.82 mmol) prepared in step 4 was added and then acetic anhydride (30 mL) was added, followed by stirring for 2 hours using a reflux cooler. When the reaction was completed, the reaction product was extracted with distilled water (50 mL)

and ethyl acetate (30 mL). The extracted organic layer was washed twice with saturated sodium hydrogen carbonate aqueous solution (50 mL), and the organic layer was separated. The separated organic layer was dried over anhydrous magnesium sulfate and then filtered under reduced pressure. The filtered solution was concentrated under reduced pressure, ethyl acetate (10 mL) was added, and then n-hexane (30 mL) was added, followed by stirring for 30 minutes. The resulting solid was filtered with n-hexane solution, thereby obtaining a target compound (2.71 g, yield: 92%).

$^1$H NMR (400 MHz, CDCl$_3$) δ 8.10 (s, 1H), 8.05-7.95 (m, 2H), 7.75 (d, 1H), 7.65 (t, 1H), 7.45 (m, 2H), 7.20-7.05 (m, 4H), 6.75 (d, 1H), 5.49 (s, 2H), 4.50 (q, 2H), 4.30-4.10 (m, 3H), 3.85 (m, 1H), 3.75 (m) 1H), 2.05 (m, 1H), 1.95 (m, 2H), 1.55 (m, 1H)

Step 6) Preparation of (S)-2-(4-(6-((4-chloro-2-fluorobenzyl)oxy)pyridin-2-yl)-3-fluorobenzyl)-1-((tetrahydrofuran-2-yl)methyl)-1H-benzo[d]imidazole-6-carboxylic acid

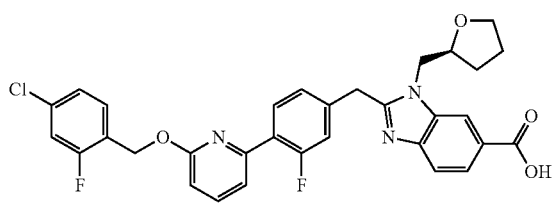 [SMILES: O=C(O)c1ccc2nc(Cc3ccc(-c4cccc(OCc5ccc(Cl)cc5F)n4)c(F)c3)n(C[C@@H]3CCCO3)c2c1]

In a 100 mL flask, (S)-methyl 2-(4-(6-((4-chloro-2-fluorobenzyl)oxy)pyridin-2-yl)-3-fluorobenzyl)-1-((tetrahydrofuran-2-yl)methyl)-1H-benzo[d]imidazole-6-carboxylate (1 g, 1.65 mmol) prepared in step 5 was dissolved in methanol (5 mL) and distilled water (5 mL), and then 2 N potassium hydroxide aqueous solution as prepared (1 mL) was added, followed by stirring at room temperature for 8 hours. When the reaction was completed, the reaction product was concentrated under reduced pressure, and then 1 N hydrochloric acid aqueous solution (3 mL) was added, followed by extraction with distilled water (10 mL) and ethyl acetate (15 mL). The extracted organic layer was dried over anhydrous magnesium sulfate and filtered under reduced pressure. The filtered solution was concentrated under reduced pressure, and the resulting solid was filtered with n-hexane solution, thereby obtaining a target compound (742 mg, yield: 76%).

$^1$H NMR (400 MHz, DMSO) δ 8.21 (s, 1H), 7.98-7.93 (t, 1H), 7.85-7.79 (m, 2H), 7.64-7.57 (m, 2H), 7.50-7.43 (m, 2H), 7.33-7.29 (m, 3H), 6.90-6.88 (d, 1H), 5.47 (s, 2H), 4.53-4.45 (m, 3H), 4.36-4.30 (m, 1H), 4.11-4.09 (m, 1H), 3.78-3.75 (q, 1H), 3.61-3.33 (q, 1H), 2.04-2.00 (m, 1H), 1.91-1.81 (m, 2H), 1.78-1.63 (m, 1H)

Example 110: Preparation of (S)-2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid Step 1) Preparation of 2-bromo-6-((4-chloro-2-fluorobenzyl)oxy)pyridine

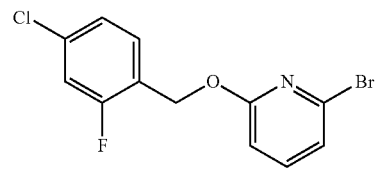 [SMILES: Fc1cc(Cl)ccc1COc1cccc(Br)n1]

To a 250 mL flask, 6-bromopyridin-2-ol (5 g, 28.73 mmol) was added and dissolved by adding dimethylformamide (25 mL). Cesium carbonate (18.40 g, 56.46 mmol) was added and then 1-(bromomethyl)-4-chloro-2-fluorobenzene (7.70 g, 34.48 mmol) was added, followed by stirring for 2 hours at room temperature. When the reaction was completed, distilled water (100 mL) was added and stirred for 30 minutes. Then, the resulting solid was filtered, thereby obtaining a target compound (8.6 g, yield: 94%).

$^1$H NMR (400 MHz, CDCl$_3$) δ 8.13-8.09 (m, 1H), 7.97-7.94 (m, 2H), 4.01 (s, 3H)

Step 2) Preparation of 6-((4-chloro-2-fluorobenzyl)oxy)-2'-((4-methoxybenzyl)oxy)-2,4'-bipyridine

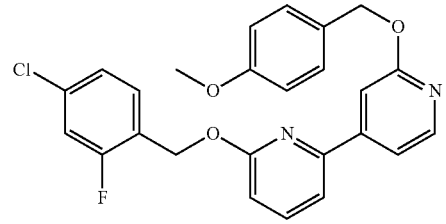 [SMILES: COc1ccc(COc2cc(-c3cccc(OCc4ccc(Cl)cc4F)n3)ccn2)cc1]

In a 100 mL flask, 2-bromo-6-((4-chloro-2-fluorobenzyl)oxy)pyridine (780 mg, 2.5 mmol) previously prepared in step 1 and 2-((4-methoxybenzyl)oxy)-4-(4,4,5,5-tetramethyl-1,3,2-dioxaborolan-2-yl)pyridine (870 mg, 2.55 mmol) were dissolved in tetrahydrofuran:distilled water: methanol (4:2:1 (volume ratio); 20 mL, 10 mL, 5 mL; total 35 mL). Calcium phosphate (1.08 g, 5 mmol) and tetrakis (triphenylphosphine)palladium(0) (90 mg, 0.12 mmol) were added to the reaction mixture. The final mixture was stirred at 68° C. for 4 hours. After completion of the reaction, ethyl acetate and distilled water were added, and then the organic layer was extracted. The organic layer was dried over anhydrous magnesium sulfate, filtered, and distilled under reduced pressure. The resulting product was purified by column chromatography (ethyl acetate:methylene chloride: n-hexane=1:1:8 (volume ratio)) and solidified with ethyl acetate and n-hexane, thereby obtaining a target compound (890 mg, yield: 80%).

$^1$H NMR (400 MHz, CDCl$_3$) δ 8.28 (d, 1H), 7.70-7.65 (t, 1H), 7.49-7.40 (m, 6H), 7.15-7.11 (m, 2H), 6.94-6.91 (d, 2H), 6.83-7.81 (d, 1H), 5.51 (s, 2H), 5.36 (s, 2H), 3.81 (s, 3H)

Step 3) Preparation of 6-((4-chloro-2-fluorobenzyl)oxy)-[2,4'-bipyridin]-2'(1'H)-one hydrochloride

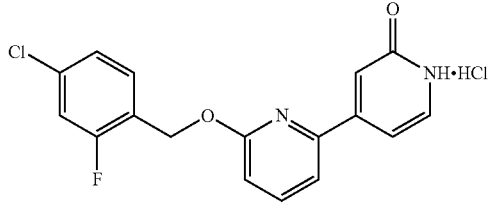

In a 100 mL flask, 6-((4-chloro-2-fluorobenzyl)oxy)-2'-((4-methoxybenzyl)oxy)-2,4'-bipyridine (890 mg, 2 mmol) previously prepared in step 2 was dissolved in methylene chloride (8 mL)) 2 mL of 4N hydrochloric acid aqueous solution (1,4-dioxane solvent) was added at room temperature, and then stirred for 5 hours. After completion of the reaction, ethyl acetate (20 mL) was added and filtered, thereby obtaining a target compound (620 mg, yield: 86%) in a solid form.

$^1$H NMR (400 MHz, DMSO) δ 7.91-7.87 (t, 1H), 7.70-7.62 (m, 2H), 7.55-7.52 (m, 2H), 8.37-7.35 (d, 1H), 7.09 (s, 1H), 7.01-6.99 (d, 1H), 6.92-6.91 (d, 1H), 5.53 (s, 2H)

Step 4) Preparation of (S)-methyl 2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylate

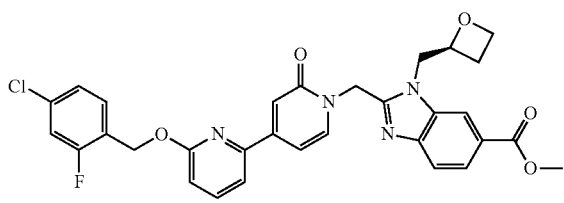 [SMILES: COC(=O)c1ccc2nc(Cn3ccc(-c4cccc(OCc5ccc(Cl)cc5F)n4)cc3=O)n(C[C@@H]3CCO3)c2c1]

6-((4-chloro-2-fluorobenzyl)oxy)-[2,4'-bipyridin]-2'(1'H)-one hydrochloride (620 mg, 1.74 mmol) previously prepared in step 3 was transferred to a 100 mL flask and dissolved in dimethylformamide (17 mL). At room temperature, triethylamine (0.24 mL, 1.74 mmol) was added, and (S)-methyl 2-(chloromethyl)-1-((tetrahydrofuran-2-yl)methyl)-1H-benzo[d]imidazole-6-carboxylate (511 mg, 1.74 mmol) and cesium carbonate (849 mg, 2.60 mmol) were added in order. The final mixture was stirred at 60° C. for 2.5 hours. After completion of the reaction, ethyl acetate and distilled water were added, and the organic layer was extracted. The organic layer was washed twice with distilled water, dried over anhydrous magnesium sulfate, filtered, and then distilled under reduced pressure. The concentrated compound was purified by column chromatography (methylene chloride:ethyl acetate=1:1 (volume ratio)) and was then solidified, thereby obtaining a target compound (700 mg, yield: 70%).

$^1$H NMR (400 MHz, CDCl$_3$) δ 8.14 (s, 1H), 7.99-7.97 (d, 1H), 7.84-7.82 (d, 1H), 7.76-7.65 (m, 2H), 7.44-7.11 (m, 4H), 6.91-6.68 (m, 3H), 5.71-5.68 (d, 1H), 5.51-5.41 (m, 4H), 5.38-5.32 (m, 1H), 5.00-4.96 (m, 1H), 4.72-4.48 (m, 3H), 3.94 (s, 3H), 2.88-2.85 (m, 1H), 2.50-2.47 (m, 1H)

Step 5) Preparation of (S)-2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid

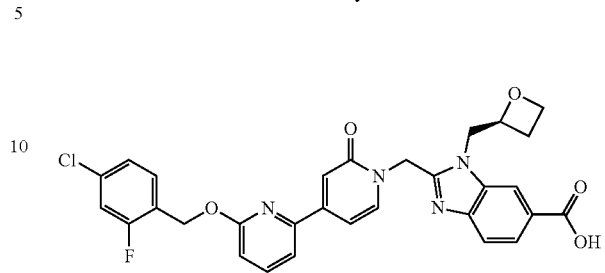

(S)-methyl 2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylate (700 mg, 1.21 mmol) previously prepared in step 4 was transferred to a 100 mL flask and dissolved in tetrahydrofuran:distilled water:methanol (2:1:2 (volume ratio); 10 mL, 5 mL, 10 mL; total 25 mL). Lithium hydroxide (152 mg, 3.62 mmol) was added at room temperature, and then stirred at room temperature for 12 hours. After completion of the reaction, the reaction product was neutralized to a pH of 6-7 with 1 N hydrochloric acid aqueous solution and extracted with ethyl acetate. The organic layer was dried over anhydrous magnesium sulfate, followed by filtration, and distilled under reduced pressure. The solvent was removed, and then the residue was solidified with ethyl acetate, thereby obtaining a target compound (480 mg, yield: 70%).

$^1$H NMR (400 MHz, DMSO) δ 8.29 (s, 1H), 7.99-7.97 (d, 1H), 7.88 (t, 1H), 7.81-7.79 (d, 1H), 7.71-7.69 (d, 1H), 7.63-7.59 (m, 2H), 7.51-7.48 (dd, 1H), 7.34-7.31 (m, 1H), 7.11 (m, 1H), 7.01-6.98 (m, 2H), 5.61-5.43 (m, 4H), 5.10-5.07 (m, 1H), 4.89-4.83 (m, 1H), 4.75-4.71 (m, 1H), 4.52-4.47 (m, 1H), 4.39-4.33 (m, 1H), 2.77-2.68 (m, 1H), 2.43-2.37 (m, 1H)

Example 131: Preparation of (S)-2-((4-(6-((4-chloro-2-fluorobenzyl)oxy)pyridin-2-yl)-1H-pyrazol-1-yl)methyl)-1-(oxetan-2-ylmethyl)-1H-benzo[d]imidazole-6-carboxylic acid

Step 1) Preparation of 2-((4-chloro-2-fluorobenzyl)oxy)-6-(1H-pyrazol-4-yl)pyridine

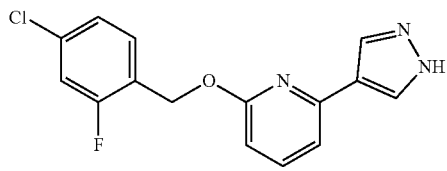 [SMILES: Fc1cc(Cl)ccc1COc1cccc(-c2cn[nH]c2)n1]

To a 250 mL 3-neck flask, 2-bromo-6-((4-chloro-2-fluorophenoxy)methyl)pyridine (2.0 g, 6.31 mmol) and tetrahydrofuran:ethanol:distilled water (4:2:1 (Volume ratio); 20 mL, 10 mL, 5 mL; total 35 mL) were added and stirred for 5 minutes to dissolve. Then, 4-(4,4,5,5-tetramethyl-1,3,2-dioxaborolan-2-yl)-1H-pyrazole (1.34 g, 6.94 mmol), tripotassium phosphate (3.34 g, 15.77 mmol) and Pd(dppf)Cl$_2$—CH$_2$Cl$_2$ (515 mg, 0.631 mmol) were added, slowly heated up to 80° C., followed by stirring for 8 hours using a reflux cooler. After completion of the reaction, the reaction product was cooled to room temperature for 30 minutes. Thereafter, the reaction mixture was concentrated under reduced pressure, and extracted with ethyl acetate (30 mL) and distilled water (60 mL), followed by separation of the organic layer. The organic layer was dried over anhydrous magnesium sulfate, concentrated under reduced pressure to remove the solvent, and separation by column chromatography was conducted under the conditions of ethyl acetate:n-hexane=4:1 (volume ratio). The resulting compound was concentrated under reduced pressure, thereby obtaining a target compound (750 mg, 2.46 mmol, yield: 38%).

$^1$H NMR (400 MHz, CDCl$_3$) δ 8.07 (s, 2H), 7.62-7.57 (t, 1H), 7.49-7.45 (t, 1H), 7.14-7.09 (m, 3H), 6.64-6.62 (d, 1H), 5.48 (s, 2H)

Step 2) Preparation of (S)-methyl 2-((4-(6-((4-chloro-2-fluorobenzyl)oxy)pyridin-2-yl)-1H-pyrazol-1-yl)methyl)-1-(oxetan-2-ylmethyl)-1H-benzo[d]imidazole-6-carboxylate

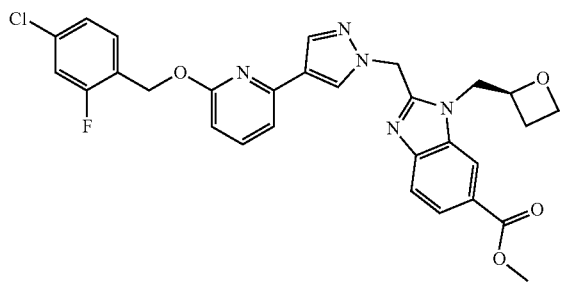 [SMILES: COC(=O)c1ccc2nc(Cn3cc(-c4cccc(OCc5ccc(Cl)cc5F)n4)cn3)n(C[C@@H]3CCO3)c2c1]

To a 100 mL flask, 2-((4-chloro-2-fluorophenoxy)oxy)-6-(1H-pyrazol-4-yl)pyridine (750 mg, 2.46 mmol) previously prepared in step 1 and acetonitrile (10 mL) were added and stirred for 10 minutes to dissolve) (S)-Methyl 2-(fluoromethyl)-1-(oxetan-2-ylmethyl)-1H-benzo[d]imidazole-6-carboxylate (800 mg, 2.71 mmol) and calcium carbonate (1.01 g, 7.38 mmol) were added, slowly heated up to 80° C., and then stirred for 3 hours using a reflux cooler. After completion of the reaction, the reaction product was cooled to room temperature for 30 minutes. Then, the reaction mixture was concentrated under reduced pressure, and extracted with ethyl acetate (30 mL) and distilled water (60 mL), followed by separation of the organic layer. The organic layer was dried over anhydrous magnesium sulfate, concentrated under reduced pressure to remove the solvent, and then separation by column chromatography was conducted under the conditions of ethyl acetate:n-hexane=2:1 (volume ratio). The resulting compound was concentrated under reduced pressure, thereby obtaining a target compound (350 mg, 0.622 mmol, yield: 25%).

$^1$H NMR (400 MHz, CDCl$_3$) δ 8.13 (s, 1H), 8.08 (s, 1H), 8.01-7.98 (d, 1H), 7.96 (s, 1H), 7.81-7.79 (d, 1H), 7.54-7.50 (t, 1H), 7.44-7.40 (t, 1H), 7.09-7.01 (m, 3H), 6.60-6.58 (d, 1H), 5.88-5.77 (q, 2H), 5.42 (s, 2H), 5.14-5.07 (m, 1H), 4.74-4.61 (m, 2H), 4.57-4.50 (d, 1H), 4.47-4.39 (m, 1H), 3.93 (s, 3H), 2.78-2.69 (m, 1H), 2.42-2.35 (m, 1H)

Step 3) Preparation of (S)-2-((4-(6-((4-chloro-2-fluorobenzyl)oxy)pyridin-2-yl)-1H-pyrazol-1-yl)methyl)-1-(oxetan-2-ylmethyl)-1H-benzo[d]imidazole-6-carboxylic acid

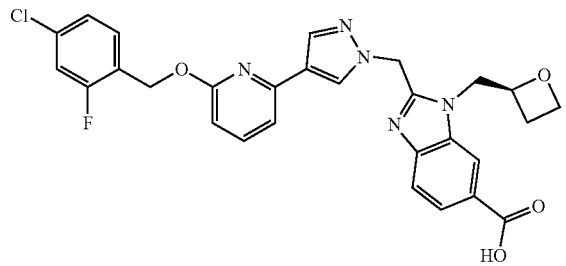 [SMILES: O=C(O)c1ccc2nc(Cn3cc(-c4cccc(OCc5ccc(Cl)cc5F)n4)cn3)n(C[C@@H]3CCO3)c2c1]

To a 100 mL flask, (S)-methyl 2-((4-(6-((4-chloro-2-fluorophenoxy)oxy)pyridin-2-yl)-1H-pyrazole-1-yl)methyl)-1-(oxetan-2-ylmethyl)-1H-benzo[d]imidazole-6-carboxylate (350 mg, 0.622 mmol) previously prepared in step 2 and tetrahydrofuran:methanol:distilled water (4:2:1 (volume ratio); 4 mL, 2 mL, 1 mL; total 7 mL) were added, stirred for 10 minutes to dissolve. Then, 2 N potassium hydroxide aqueous solution (5 mL) was added, followed by stirring at room temperature for 4 hours. After completion of the reaction, the mixed solution was concentrated under reduced pressure) 2 N hydrochloric acid aqueous solution (4 mL) was added to neutralize the concentrate to a pH of 7-8 and produce a solid compound. The resulting compound was filtered under reduced pressure and dried, thereby obtaining a target compound (250 mg, 0.456 mmol, yield: 73.35%).

$^1$H NMR (400 MHz, DMSO) δ 8.46 (s, 1H), 8.31 (s, 1H), 8.07 (s, 1H), 7.84-7.82 (d, 1H), 7.72-7.59 (m, 3H), 7.45-7.42 (dd, 1H), 7.31-7.27 (m, 2H), 6.68-6.65 (d, 1H), 5.91-5.79 (q, 2H), 5.45 (s, 2H), 4.94-4.92 (m, 1H), 4.85-4.79 (m, 1H), 4.70-4.66 (m, 1H), 4.51-4.47 (m, 1H), 4.39-4.34 (m, 1H), 2.71-2.62 (m, 1H), 2.38-2.35 (m, 1H)

The following Examples 1-6, 8-59, and 61-103 were prepared in the same manner as in Example 60, except that suitable starting materials were used according to the structure of the compound to be prepared.

Example 1: Preparation of 2-(4-(6-(4-chloro-2-fluorobenzyloxy)pyridin-2-yl)benzyl)-1-(pyridin-3-ylmethyl)-1H-benzo[d]imidazole-6-carboxylic acid

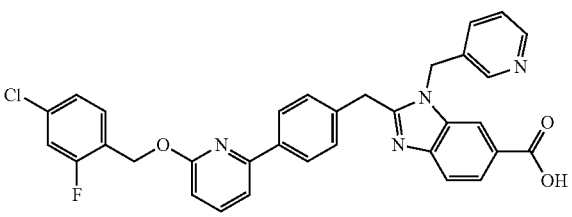 [SMILES: O=C(O)c1ccc2nc(Cc3ccc(-c4cccc(OCc5ccc(Cl)cc5F)n4)cc3)n(Cc3cccnc3)c2c1]

$^1$H NMR (400 MHz, MeOD) δ 8.75 (s, 2H), 8.45 (s, 1H), 8.33-8.32 (d, 1H), 8.20 (d, 1H), 7.99-7.95 (m, 3H), 7.85-7.76 (m, 2H), 7.57-7.53 (t, 1H), 7.47-7.43 (m, 3H), 7.27-7.22 (m, 2H), 6.85-6.83 (d, 1H), 6.17 (s, 2H), 5.53 (s, 2H), 4.83 (s, 2H),

Example 2: Preparation of 2-(4-(6-(4-chloro-2-fluorobenzyloxy)pyridin-2-yl)benzyl)-1-(2-methoxyethyl)-1H-benzo[d]imidazole-6-carboxylic acid

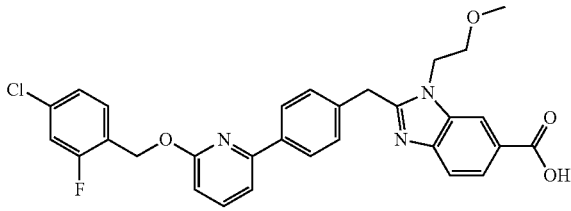 [SMILES: COCCn1c(Cc2ccc(-c3cccc(OCc4ccc(Cl)cc4F)n3)cc2)nc2ccc(C(=O)O)cc21]

¹H NMR (400 MHz, DMSO) δ 8.15 (s, 1H), 8.04-8.02 (d, 2H), 7.81-7.77 (m, 2H), 7.64-7.55 (m, 3H), 7.49-7.29 (m, 4H), 6.83-6.81 (d, 1H), 5.50 (s, 2H), 4.49-4.46 (t, 2H), 4.41 (s, 2H), 3.56-3.54 (m, 2H), 3.15 (s, 3H)

Example 3: Preparation of 2-(4-(6-(4-chloro-2-fluorobenzyloxy)pyridin-2-yl)-2-fluorobenzyl)-1-(2-methoxyethyl)-1H-benzo[d]imidazole-6-carboxylic acid

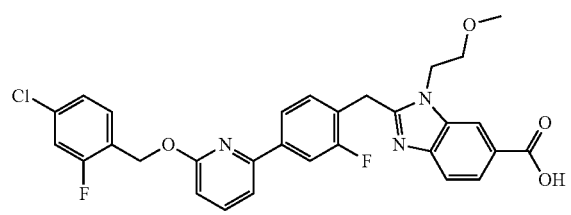 [SMILES: COCCn1c(Cc2ccc(-c3cccc(OCc4ccc(Cl)cc4F)n3)cc2F)nc2ccc(C(=O)O)cc21]

¹H NMR (400 MHz, CDCl₃) δ 8.15 (s, 1H), 8.03-8.02 (d, 1H), 7.82-7.69 (m, 4H), 7.34-7.30 (m, 3H), 7.14-7.11 (d, 2H), 6.76-6.74 (d, 1H), 5.50 (s, 2H), 4.48 (s, 2H), 4.37-4.35 (t, 2H), 3.65-3.62 (t, 2H), 3.25 (s, 3H)

Example 4: Preparation of 2-(4-(6-(4-chloro-2-fluorobenzyloxy)pyridin-2-yl)-3-methylbenzyl)-1-(2-methoxyethyl)-1H-benzo[d]imidazole-6-carboxylic acid

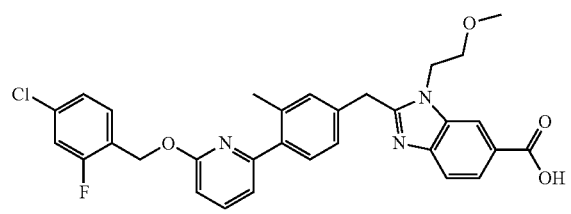 [SMILES: COCCn1c(Cc2ccc(-c3cccc(OCc4ccc(Cl)cc4F)n3)c(C)c2)nc2ccc(C(=O)O)cc21]

¹H NMR (400 MHz, DMSO) δ 12.75 (s, 1H), 8.16 (s, 1H), 7.83-7.78 (m, 2H), 7.64-7.62 (d, 1H), 7.57-7.55 (t, 1H), 7.53-7.49 (d, 1H), 7.47-7.46 (d, 1H), 7.38-7.36 (d, 1H), 7.32-7.13 (m, 3H), 6.87-6.85 (d, 1H), 5.39 (s, 2H), 4.51-4.48 (t, 2H), 4.36 (s, 2H), 3.58-3.56 (t, 2H), 3.33 (s, 3H), 3.18 (s, 3H)

Example 5: Preparation of 2-(4-(6-(4-chloro-2-fluorobenzyloxy)pyridin-2-yl)-2-nitrobenzyl)-1-(2-methoxyethyl)-1H-benzo[d]imidazole-6-carboxylic acid

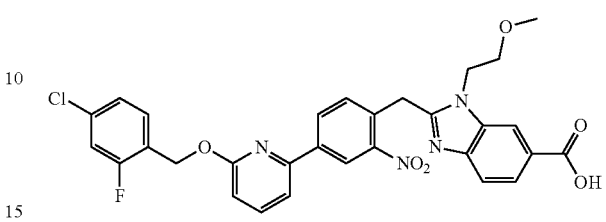

¹H NMR (400 MHz, DMSO) δ 8.85 (s, 1H), 8.65 (d, 1H), 8.40 (s, 1H), 7.97-7.88 (m, 4H), 7.76-7.73 (d, 1H), 7.69-7.65 (t, 1H), 7.50-7.49 (d, 1H), 7.35-7.33 (d, 1H), 7.04-7.02 (d, 1H), 5.58 (s, 2H), 4.99-4.98 (t, 2H), 3.87-3.84 (t, 2H), 3.25 (s, 3H)

Example 6: Preparation of 2-(4-(6-(4-chloro-2-fluorobenzyloxy)pyridin-2-yl)-3-fluorobenzyl)-1-(2-methoxyethyl)-1H-benzo[d]imidazole-6-carboxylic acid

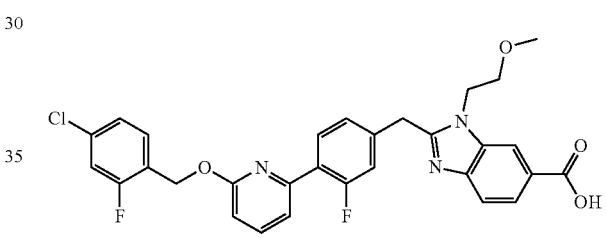

¹H NMR (400 MHz, DMSO) δ 8.29 (s, 1H), 7.93 (t, 1H), 7.83-7.80 (m, 2H), 7.64-7.62 (m, 2H), 7.57-7.43 (m, 2H), 7.33-7.28 (m, 3H), 6.90-6.88 (d, 1H), 5.47 (s, 2H), 4.54-4.52 (t, 2H), 4.38 (s, 2H), 3.61-3.59 (t, 2H), 3.18 (s, 3H)

Example 8: Preparation of 2-((3'-(4-cyano-2-fluorobenzyloxy)biphenyl-4-yl)methyl)-1-((tetrahydrofuran-2-yl)methyl)-1H-benzo[d]imidazole-6-carboxylic acid

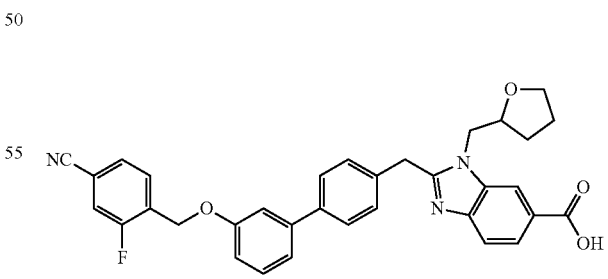

¹H NMR (400 MHz, CDCl₃) δ 8.16 (s, 1H), 8.07-8.04 (d, 1H), 7.85-7.83 (m, 3H), 7.63-7.58 (m, 1H), 7.56-7.50 (m, 3H), 7.40-7.31 (m, 4H), 7.19-7.14 (m, 2H), 6.94-6.90 (m, 1H), 5.21 (s, 2H), 4.60-4.46 (q, 2H), 4.26-4.14 (m, 3H), 3.89-3.84 (q, 1H), 3.76-3.70 (q, 1H), 2.12-1.90 (m, 1H), 1.88-1.86 (m, 2H), 1.57-1.52 (m, 1H)

Example 9: Preparation of 2-((3'-(4-cyano-2-fluorobenzyloxy)-2-fluorobiphenyl-4-yl)methyl)-1-((tetrahydrofuran-2-yl)methyl)-1H-benzo[d]imidazole-6-carboxylic acid

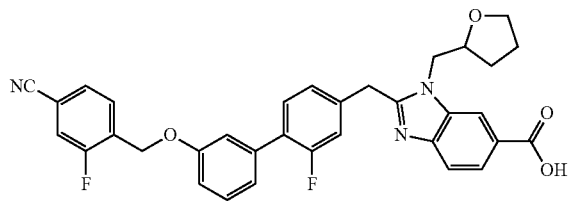 [SMILES: N#Cc1ccc(COc2cccc(-c3ccc(Cc4nc5ccc(C(=O)O)cc5n4CC4CCCO4)cc3F)c2)c(F)c1]

$^1$H NMR (400 MHz, CDCl$_3$) δ 8.16 (s, 1H), 8.07-8.05 (d, 1H), 7.84-7.82 (d, 1H), 7.62-7.56 (m, 1H), 7.50-7.48 (d, 1H), 7.39-7.32 (m, 3H), 7.15-7.12 (m, 4H), 6.99-6.94 (m, 1H), 5.20 (s, 2H), 4.58-4.45 (q, 2H), 4.43-4.12 (m, 3H), 3.92-3.84 (q, 1H), 3.77-3.72 (q, 1H), 2.17-2.03 (m, 1H), 1.92-1.84 (m, 2H), 1.60-1.55 (m, 1H)

Example 10: Preparation of 2-(4-(6-(4-chloro-2-fluorobenzyloxy)pyridin-2-yl)benzyl)-1-((tetrahydrofuran-2-yl)methyl)-1H-benzo[d]imidazole-6-carboxylic acid

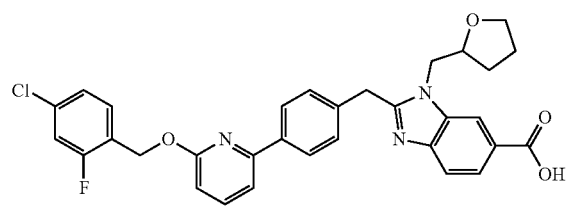 [SMILES: O=C(O)c1ccc2nc(Cc3ccc(-c4cccc(OCc5ccc(Cl)cc5F)n4)cc3)n(CC3CCCO3)c2c1]

$^1$H NMR (400 MHz, DMSO) δ 8.19 (s, 1H), 8.04-8.02 (d, 2H), 7.82-7.84 (t, 2H), 7.63-7.56 (m, 3H), 7.51-7.50 (dd, 1H), 7.48-7.41 (d, 2H), 7.31-7.30 (dd, 1H), 6.84-6.82 (d, 1H), 5.50 (s, 2H), 4.49-4.42 (m, 3H), 4.31-4.25 (q, 1H), 4.09-4.02 (m, 1H), 3.80-3.75 (q, 1H), 3.63-3.57 (q, 1H), 2.09-1.98 (m, 1H), 1.86-1.76 (m, 2H), 1.62-1.59 (m, 1H)

Example 11: Preparation of 2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid

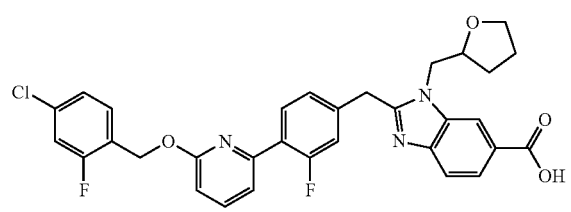 [SMILES: O=C(O)c1ccc2nc(Cc3ccc(-c4cccc(OCc5ccc(Cl)cc5F)n4)c(F)c3)n(CC3CCCO3)c2c1]

$^1$H NMR (400 MHz, DMSO) δ 8.20 (s, 1H), 7.97-7.93 (t, 1H), 7.85-7.78 (m, 2H), 7.64-7.58 (m, 2H), 7.50-7.43 (m, 2H), 7.32-7.29 (t, 3H), 6.90-6.88 (d, 1H), 5.47 (s, 2H), 4.53-4.49 (m, 3H), 4.36-4.30 (m, 1H), 4.12-4.06 (q, 1H), 3.80-3.74 (q, 1H), 3.63-3.5 (q, 1H), 2.09-2.01 (m, 1H), 1.87-1.76 (m, 2H), 1.65-1.60 (m, 1H)

Example 12: Preparation of 2-(4-(6-(4-chloro-2-fluorobenzyloxy)pyridin-2-yl)benzyl)-1-(furan-2-ylmethyl)-1H-benzo[d]imidazole-6-carboxylic acid

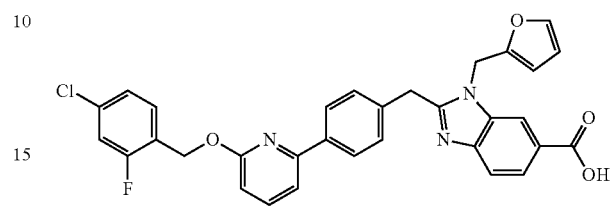

$^1$H NMR (400 MHz, DMSO) δ 8.25 (s, 1H), 8.05-8.02 (d, 2H), 7.82-7.80 (m, 2H), 7.65-7.56 (m, 4H), 7.49-7.48 (d, 1H), 7.44-7.42 (d, 1H), 7.33-7.31 (m, 2H), 6.84-6.82 (d, 1H), 6.45-6.44 (d, 1H), 6.37 (d, 1H), 5.58 (s, 2H), 5.50 (s, 2H), 4.47 (s, 2H)

Example 13: Preparation of 2-(4-(6-(4-chloro-2-fluorobenzyloxy)pyridin-2-yl)-2-fluorobenzyl)-1-(furan-2-ylmethyl)-1H-benzo[d]imidazole-6-carboxylic acid

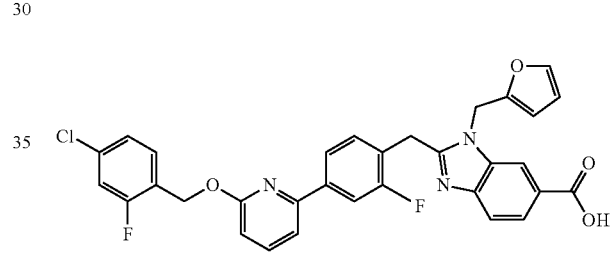

$^1$H NMR (400 MHz, DMSO) δ 8.29 (s, 1H), 7.84-7.78 (m, 4H), 7.66-7.60 (m, 4H), 7.51 (d, 1H), 7.49-7.48 (t, 1H), 7.44-7.40 (d, 1H), 6.89-6.87 (d, 1H), 6.53-6.52 (d, 1H), 6.42-6.41 (d, 1H), 5.69 (s, 2H), 5.52 (s, 2H), 4.50 (s, 2H)

Example 14: Preparation of 2-((3'-(4-cyano-2-fluorobenzyloxy)-3-fluorobiphenyl-4-yl)methyl)-1-((tetrahydrofuran-2-yl)methyl)-1H-benzo[d]imidazole-6-carboxylic acid

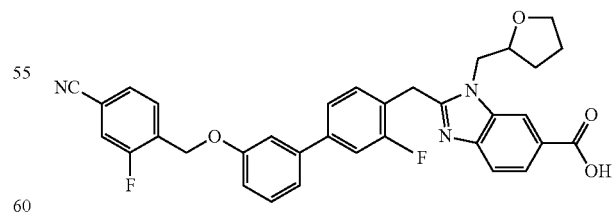

$^1$H NMR (400 MHz, MeOD) δ 8.28 (s, 1H), 7.98-7.96 (dd, 1H), 7.81-7.78 (t, 1H), 7.66-7.62 (m, 3H), 7.48-7.40 (m, 3H), 7.38-7.28 (m, 3H), 7.06-7.04 (d, 1H), 7.35 (s, 2H), 5.3 (s, 2H), 4.54-4.48 (m, 3H), 4.36-4.20 (m, 2H), 3.93-3.88 (m, 1H), 3.76-3.71 (m, 1H), 2.17-2.11 (m, 1H), 2.00-1.89 (m, 2H), 1.74-1.69 (m, 1H)

Example 15: Preparation of 2-(4-(6-(4-cyano-2-fluorobenzyloxy)pyridin-2-yl)-2-fluorobenzyl)-1-((tetrahydrofuran-2-yl)methyl)-1H-benzo[d]imidazole-6-carboxylic acid

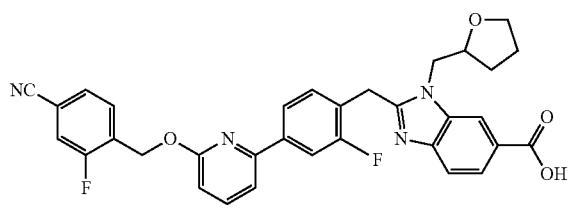 [SMILES: N#Cc1ccc(COc2cccc(-c3ccc(Cc4nc5ccc(C(=O)O)cc5n4CC4CCCO4)c(F)c3)n2)c(F)c1]

$^1$H NMR (400 MHz, MeOD) δ 8.23 (s, 1H), 7.98-7.96 (dd, 1H), 7.81-7.61 (m, 6H), 7.55-7.43 (m, 2H), 7.30-7.28 (t, 1H), 6.85-6.82 (d, 1H), 5.65 (s, 1H), 4.57-4.52 (d, 1H), 4.46-4.41 (d, 2H), 4.30-4.17 (m, 2H), 3.95-3.89 (m, 2H), 3.75-3.70 (q, 1H), 2.17-2.09 (m, 1H), 1.95-1.88 (m, 2H), 1.71-1.68 (m, 1H)

Example 16: Preparation of 2-((3'-(4-chloro-2-fluorobenzyloxy)-3-fluorobiphenyl-4-yl)methyl)-1-((tetrahydrofuran-2-yl)methyl)-1H-benzo[d]imidazole-6-carboxylic acid

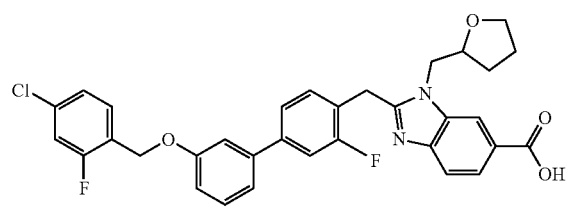

$^1$H NMR (400 MHz, CDCl$_3$) δ 8.19 (s, 1H), 8.06-8.04 (d, 1H), 7.84-7.82 (d, 1H), 7.47-7.43 (t, 1H), 7.37-7.26 (m, 4H), 7.17-7.11 (m, 4H), 6.95-6.93 (d, 1H), 5.11 (s, 2H), 4.53-4.33 (q, 2H), 4.33-4.29 (m, 1H), 4.27-4.16 (m, 2H), 3.94-3.85 (q, 1H), 3.76-3.70 (q, 1H), 2.12-2.03 (m, 1H), 1.92-1.85 (m, 2H), 1.65-1.60 (m, 1H)

Example 17: Preparation of 2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid

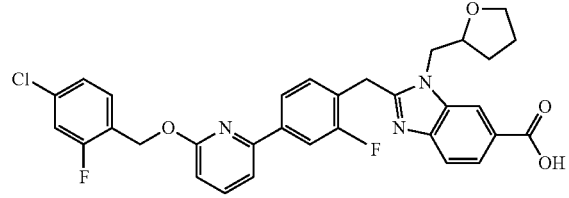 [SMILES: O=C(O)c1ccc2nc(Cc3ccc(-c4cccc(OCc5ccc(Cl)cc5F)n4)cc3F)n(CC3CCCO3)c2c1]

$^1$H NMR (400 MHz, DMSO) δ 8.21 (s, 1H), 7.93-7.77 (m, 4H), 7.66-7.56 (m, 3H), 7.51-7.39 (m, 2H), 7.33-7.31 (d, 1H), 6.89-6.87 (d, 1H), 5.52 (s, 2H), 4.55-4.33 (m, 4H), 4.18-4.14 (d, 1H), 3.82-3.76 (q, 1H), 3.66-3.60 (q, 1H), 2.11-2.03 (m, 1H), 1.88-1.77 (m, 2H), 1.66-1.61 (m, 1H)

Example 18: Preparation of 2-(4-(6-(4-cyano-2-fluorobenzyloxy)pyridin-2-yl)benzyl)-1-(furan-2-ylmethyl)-1H-benzo[d]imidazole-6-carboxylic acid

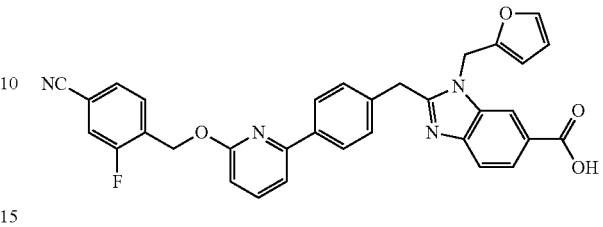

$^1$H NMR (400 MHz, DMSO) δ 8.27 (s, 1H), 7.84-7.59 (m, 10H), 7.43-7.41 (d, 2H), 6.88 (d, 1H), 6.45 (d, 1H), 6.38 (d, 1H), 5.62-5.60 (d, 4H), 4.48 (s, 2H)

Example 19: Preparation of 2-(4-(6-(4-cyano-2-fluorobenzyloxy)pyridin-2-yl)-2-fluorobenzyl)-1-(furan-2-ylmethyl)-1H-benzo[d]imidazole-6-carboxylic acid

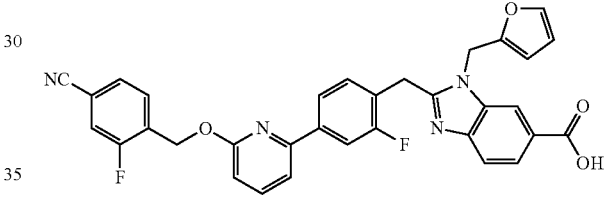

$^1$H NMR (400 MHz, DMSO) δ 8.29 (s, 1H), 7.84-7.58 (m, 10), 7.43-7.41 (t, 1H), 6.94-6.90 (d, 1H), 6.53 (s, 1H), 6.41 (s, 1H), 5.69 (s, 2H), 5.58 (s, 2H), 4.49 (s, 2H)

Example 20: Preparation of 2-(4-(6-(4-cyano-2-fluorobenzyloxy)pyridin-2-yl)benzyl)-1-(2-methoxyethyl)-1H-benzo[d]imidazole-6-carboxylic acid

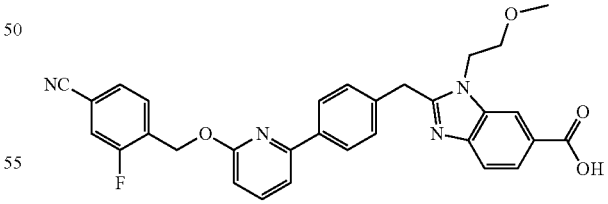

$^1$H NMR (400 MHz, MeOD) δ 8.24 (s, 1H), 8.00-7.97 (d, 3H), 7.75-7.49 (m, 6H), 7.37-7.35 (d, 2H), 6.83-6.81 (d, 1H), 5.63 (s, 2H), 4.49 (s, 2H), 4.44 (t, 2H), 3.59 (t, 2H), 3.23 (s, 3H)

Example 21: Preparation of 2-((3'-(4-cyano-2-fluorobenzyloxy)biphenyl-4-yl)methyl)-1-(2-methoxyethyl)-1H-benzo[d]imidazole-6-carboxylic acid

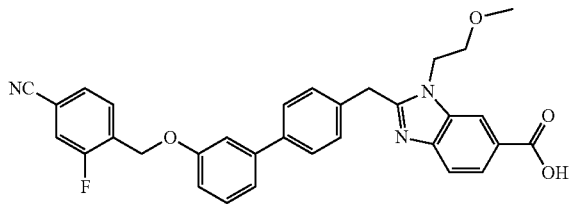 [SMILES: COCCn1c(Cc2ccc(-c3cccc(OCc4ccc(C#N)cc4F)c3)cc2)nc2ccc(C(=O)O)cc21]

¹H NMR (400 MHz, MeOD) δ 8.24 (s, 1H), 8.00 (d, 1H), 7.78-7.59 (m, 6H), 7.39-7.3 (m, 3H), 7.25-7.22 (m, 2H), 7.02-6.99 (d, 1H), 5.29 (s, 2H), 4.48 (s, 2H), 4.45-4.43 (t, 2H), 3.61-3.58 (t, 2H), 3.24 (s, 3H)

Example 22: Preparation of 2-((3'-(4-chloro-2-fluorobenzyloxy)biphenyl-4-yl)methyl)-1-(2-methoxyethyl)-1H-benzo[d]imidazole-6-carboxylic acid

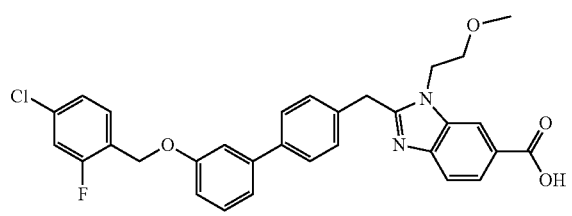 [SMILES: COCCn1c(Cc2ccc(-c3cccc(OCc4ccc(Cl)cc4F)c3)cc2)nc2ccc(C(=O)O)cc21]

¹H NMR (400 MHz, DMSO) δ 12.76 (s, 1H), 8.16 (s, 1H), 7.81-7.79 (d, 1H), 7.63 (s, 4H), 7.52-7.24 (m, 7H), 7.02-7.00 (d, 1H), 5.21 (s, 2H), 4.49 (s, 2H), 4.39 (s, 2H), 3.56 (s, 2H), 3.16 (s, 3H)

Example 23: Preparation of 1-(furan-2-ylmethyl)-2-((5-(3-(3-methoxybenzyloxy)phenyl)pyridin-2-yl)methyl)-1H-benzo[d]imidazole-6-carboxylic acid

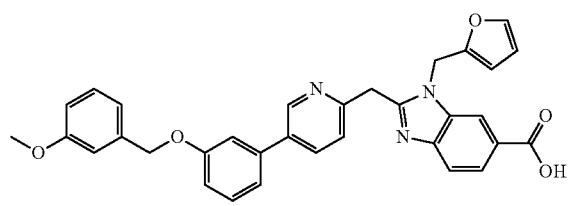 [SMILES: COc1cccc(COc2cccc(-c3ccc(Cc4nc5ccc(C(=O)O)cc5n4Cc4ccco4)nc3)c2)c1]

¹H NMR (400 MHz, CDCl₃) δ 8.74 (d, 1H), 8.18 (s, 1H), 8.03-8.01 (d, 1H), 7.81-7.78 (m, 2H), 7.42-7.35 (m, 2H), 7.30-7.28 (m, 2H), 7.14-7.12 (d, 2H), 7.02-7.00 (m, 3H), 6.88-6.85 (dd, 1H), 6.25-6.21 (m, 2H), 5.51 (s, 2H), 5.09 (s, 2H), 4.70 (s, 2H), 3.81 (s, 3H)

Example 24: Preparation of 2-((3'-(4-chloro-2-fluorobenzyloxy)biphenyl-4-yl)methyl)-1-((tetrahydrofuran-2-yl)methyl)-1H-benzo[d]imidazole-6-carboxylic acid

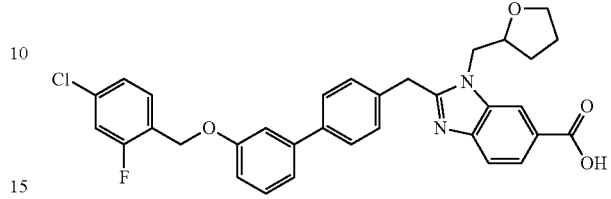

¹H NMR (400 MHz, CDCl₃) δ 8.17 (s, 1H), 8.08-8.05 (d, 1H), 7.86-7.84 (d, 1H), 7.52-7.44 (m, 3H), 7.35-7.31 (t, 3H), 7.17-7.10 (m, 4H), 6.93-6.91 (d, 1H), 5.12 (s, 2H), 4.61-4.47 (m, 2H), 4.22-4.09 (m, 3H), 3.89-3.70 (m, 2H), 2.04-1.99 (m, 1H), 1.89-1.82 (m, 2H), 1.57-1.52 (m, 1H)

Example 25: Preparation of 2-(4-(6-(4-cyano-2-fluorobenzyloxy)pyridin-2-yl)-2-fluorobenzyl)-1-(2-methoxyethyl)-1H-benzo[d]imidazole-6-carboxylic acid

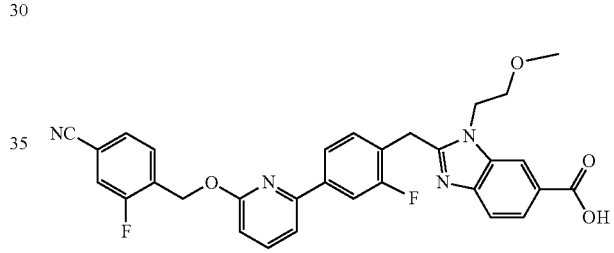

¹H NMR (400 MHz, DMSO) δ 8.26-8.23 (d, 1H), 7.95-7.57 (m, 9H), 7.46-7.30 (m, 1H), 7.00-6.92 (m, 1H), 5.62 (s, 2H), 4.61-4.60 (m, 2H), 4.59-4.40 (d, 2H), 3.86 (t, 2H), 3.20 (s, 3H)

Example 26: Preparation of 2-((3'-(4-cyano-2-fluorobenzyloxy)-3-fluorobiphenyl-4-yl)methyl)-1-(2-methoxyethyl)-1H-benzo[d]imidazole-6-carboxylic acid

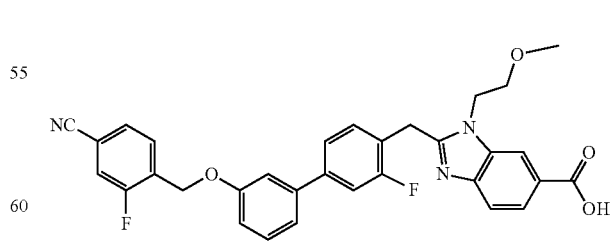

¹H NMR (400 MHz, DMSO) δ 8.36 (s, 1H), 7.95-7.92 (d, 2H), 7.81-7.75 (m, 2H), 7.71-7.57 (m, 3H), 7.49-7.40 (m, 3H), 7.36-7.34 (d, 1H), 7.10-7.08 (dd, 1H), 5.35 (s, 2H), 4.70 (s, 2H), 4.48 (s, 2H), 3.70 (t, 2H), 3.38 (s, 3H)

Example 27: Preparation of 2-((3'-(4-cyano-2-fluo-robenzyloxy)biphenyl-4-yl)methyl)-1-(furan-2-ylmethyl)-1H-benzo[d]imidazole-6-carboxylic acid

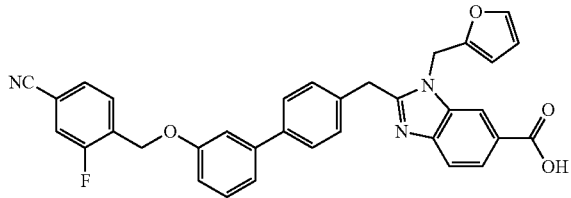 [SMILES: N#Cc1ccc(COc2cccc(-c3ccc(Cc4nc5ccc(C(=O)O)cc5n4Cc4ccco4)cc3)c2)c(F)c1]

$^1$H NMR (400 MHz, DMSO) δ 8.25 (s, 1H), 7.95-7.92 (dd, 1H), 7.82-7.78 (m, 2H), 7.75-7.73 (m, 1H), 7.67-7.62 (m, 3H), 7.58 (s, 1H), 7.41-7.39 (d, 3H), 7.31-7.25 (m, 2H), 7.05-7.02 (dd, 1H), 6.43-6.37 (d, 2H), 5.62 (s, 2H), 5.33 (s, 1H), 4.46 (s, 2H)

Example 28: Preparation of 2-((3'-(4-cyano-2-fluorobenzyloxy)-3-fluorobiphenyl-4-yl)methyl)-1-(furan-2-ylmethyl)-1H-benzo[d]imidazole-6-carboxylic acid

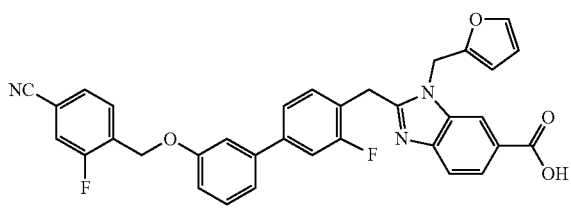 [SMILES: N#Cc1ccc(COc2cccc(-c3ccc(Cc4nc5ccc(C(=O)O)cc5n4Cc4ccco4)c(F)c3)c2)c(F)c1]

$^1$H NMR (400 MHz, DMSO) δ 8.29 (s, 1H), 7.95-7.93 (d, 1H), 7.83-7.74 (m, 3H), 7.67-7.54 (m, 3H), 7.51-7.49 (dd, 1H), 7.44-7.37 (m, 3H), 7.34-7.31 (m, 1H), 7.09 (d, 1H), 6.52 (s, 1H), 6.41 (s, 1H), 5.69 (s, 2H), 5.35 (s, 2H), 4.48 (s, 2H)

Example 29: Preparation of 2-((3'-(4-cyano-2-fluorobenzyloxy)-2-methylbiphenyl-4-yl)methyl)-1-(furan-2-ylmethyl)-1H-benzo[d]imidazole-6-carboxylic acid

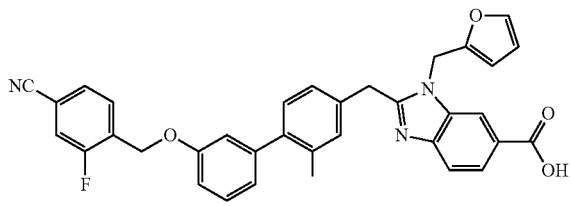 [SMILES: Cc1cc(Cc2nc3ccc(C(=O)O)cc3n2Cc2ccco2)ccc1-c1cccc(OCc2ccc(C#N)cc2F)c1]

$^1$H NMR (400 MHz, CDCl$_3$) δ 8.23 (s, 1H), 8.08-8.05 (dd, 1H), 7.85-7.83 (d, 1H), 7.72-7.68 (t, 1H), 7.50-7.48 (dd, 1H), 7.39-7.31 (m, 3H), 7.16 (s, 3H), 6.95-6.87 (m, 3H), 6.29-6.28 (m, 1H), 6.16 (d, 1H), 5.26 (s, 2H), 5.19 (s, 2H), 4.47 (s, 2H)

Example 30: Preparation of 2-(4-(6-(4-cyano-2-fluorobenzyloxy)pyridin-2-yl)-3-methylbenzyl)-1-(furan-2-ylmethyl)-1H-benzo[d]imidazole-6-carboxylic acid

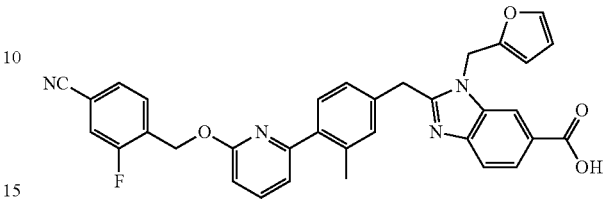

$^1$H NMR (400 MHz, CDCl$_3$) δ 8.22 (s, 1H), 8.07-8.05 (dd, 1H), 7.84-7.82 (d, 1H), 7.69-7.60 (m, 2H), 7.45-7.43 (dd, 1H), 7.37-7.33 (m, 3H), 7.18-7.16 (m, 2H), 7.02-7.01 (d, 1H), 6.79 (d, 1H), 6.29-6.27 (m, 1H), 6.18 (d, 1H), 5.52 (s, 2H), 5.24 (s, 2H), 4.47 (s, 2H)

Example 31: Preparation of 2-(4-(6-((4-chloro-2-fluorophenoxy)methyl)pyridin-2-yl)-2-fluorobenzyl)-1-(2-methoxyethyl)-1H-benzo[d]imidazole-6-carboxylic acid

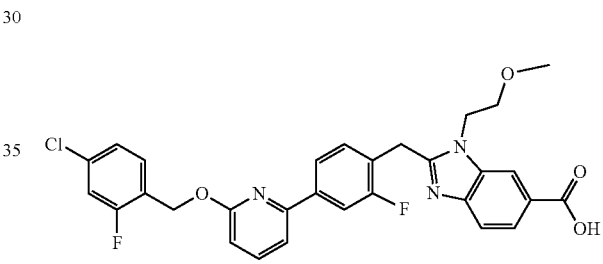

$^1$H NMR (400 MHz, DMSO) δ 8.35 (s, 1H), 8.03-7.91 (m, 5H), 7.69-7.67 (d, 1H), 7.53-7.47 (m, 3H), 7.35-7.31 (t, 1H), 7.24-7.21 (m, 1H), 5.37 (s, 2H), 4.69 (s, 2H), 4.58 (s, 2H), 3.69-3.67 (t, 2H), 3.20 (s, 3H)

Example 32: Preparation of 2-((3'-(4-chloro-2-fluorobenzyloxy)-3-fluorobiphenyl-4-yl)methyl)-1-(oxazol-5-ylmethyl)-1H-benzo[d]imidazole-6-carboxylic acid

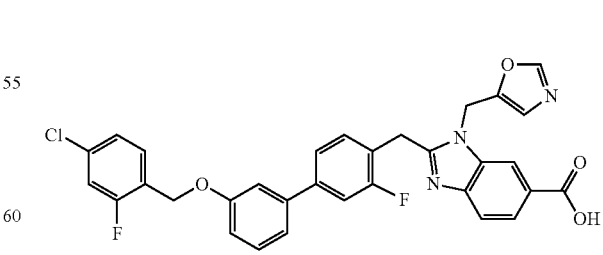

$^1$H NMR (400 MHz, DMSO) δ 8.32 (s, 1H), 8.31 (s, 1H), 7.82-7.77 (dd, 1H), 7.66-7.49 (m, 5H), 7.43-7.31 (m, 5H), 7.26 (s, 1H), 7.07-7.04 (dd, 1H), 5.83 (s, 2H), 5.23 (s, 2H), 4.48 (s, 2H)

Example 33: Preparation of 2-((3'-(4-chloro-2-fluorobenzyloxy)-2-fluorobiphenyl-4-yl)methyl)-1-(oxazol-5-ylmethyl)-1H-benzo[d]imidazole-6-carboxylic acid

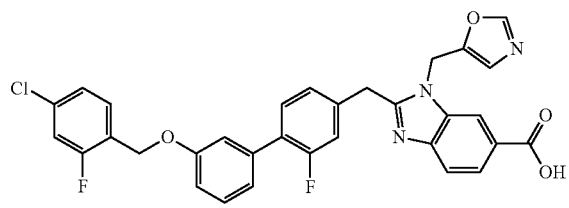

¹H NMR (400 MHz, DMSO) δ 8.31-8.22 (d, 2H), 7.84-7.81 (dd, 1H), 7.67-7.60 (m, 2H), 7.52-7.45 (m, 2H), 7.42-7.33 (m, 2H), 7.28-7.21 (m, 2H), 7.17-7.13 (m, 3H), 7.08-7.05 (dd, 1H), 5.79 (s, 2H), 5.18 (s, 2H), 4.49 (s, 2H)

Example 34: Preparation of 2-(4-(6-(4-chloro-2-fluorobenzyloxy)pyridin-2-yl)-2-fluorobenzyl)-1-(oxazol-5-ylmethyl)-1H-benzo[d]imidazole-6-carboxylic acid

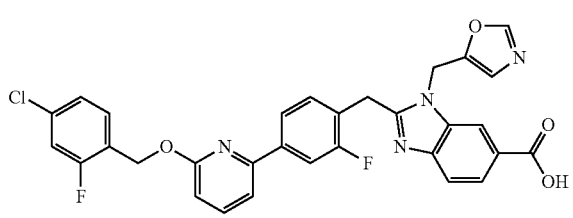 [SMILES: O=C(O)c1ccc2nc(Cc3ccc(-c4cccc(OCc5ccc(Cl)cc5F)c4)cc3F)n(Cc3cnco3)c2c1]

¹H NMR (400 MHz, DMSO) δ 8.33 (s, 1H), 8.31 (s, 1H), 7.92-7.79 (m, 4H), 7.66-7.59 (m, 3H), 7.51-7.50 (dd, 1H), 7.49-7.40 (t, 1H), 7.34-7.31 (dd, 1H), 6.89-6.87 (d, 1H), 5.83 (s, 2H), 5.52 (s, 2H), 4.50 (s, 2H)

Example 35: Preparation of 2-(4-(6-(4-chloro-2-fluorobenzyloxy)pyridin-2-yl)-3-fluorobenzyl)-1-(oxazol-5-ylmethyl)-1H-benzo[d]imidazole-6-carboxylic acid

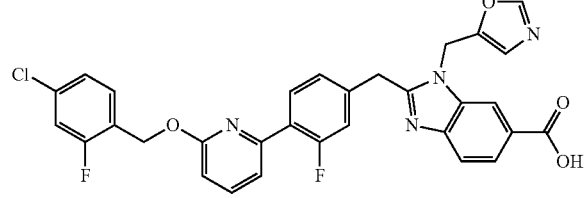

¹H NMR (400 MHz, DMSO) δ 8.30 (s, 1H), 8.27 (s, 1H), 7.95-7.91 (t, 1H), 7.84-7.82 (t, 2H), 7.67-7.65 (m, 1H), 7.60 (t, 1H), 7.49 (dd, 1H), 7.44 (dd, 1H) 7.33-7.27 (m, 3H), 6.90-6.88 (d, 1H), 5.79 (s, 2H), 5.47 (s, 2H), 4.51 (s, 2H)

Example 36: Preparation of 2-((3'-(4-chloro-2-fluorobenzyloxy)-3-fluorobiphenyl-4-yl)methyl)-1-(2-methoxyethyl)-1H-benzo[d]imidazole-6-carboxylic acid

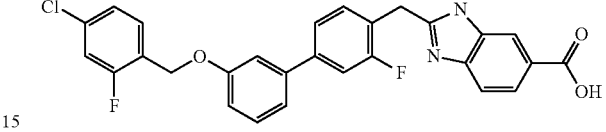

¹H NMR (400 MHz, DMSO) δ 8.19 (s, 1H), 7.80-7.77 (dd, 1H), 7.65-7.57 (m, 3H), 7.53-7.50 (m, 2H), 7.42-7.31 (m, 5H), 7.06-7.04 (dd, 1H), 5.23 (s, 2H), 4.57-4.54 (t, 2H), 4.40 (s, 2H), 3.67-3.64 (t, 2H), 3.20 (s, 3H)

Example 37: Preparation of 2-(4-(6-(4-chloro-2-fluorobenzyloxy)pyridin-2-yl)-2,6-difluorobenzyl)-1-(2-methoxyethyl)-1H-benzo[d]imidazole-6-carboxylic acid

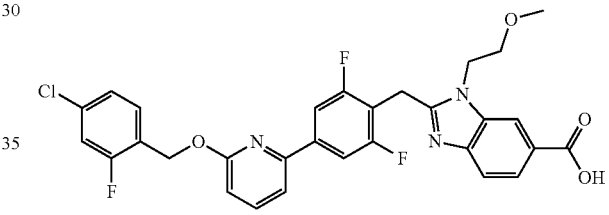

¹H NMR (400 MHz, DMSO) δ 12.79 (br s, 1H), 8.19 (s, 1H), 7.90-7.85 (t, 3H), 7.77-7.70 (t) 2H), 7.64-7.60 (t, 1H), 7.54-7.49 (m, 2H), 7.34-7.32 (dd, 1H), 6.94-6.92 (d, 1H), 5.54 (s, 2H), 4.64-4.62 (t, 2H), 4.44 (s, 2H), 3.73-3.70 (t, 2H), 3.24 (s, 3H)

Example 38: Preparation of 2-(4-(6-(4-cyano-2-fluorobenzyloxy)pyridin-2-yl)-3-fluorobenzyl)-1-(2-methoxyethyl)-1H-benzo[d]imidazole-6-carboxylic acid

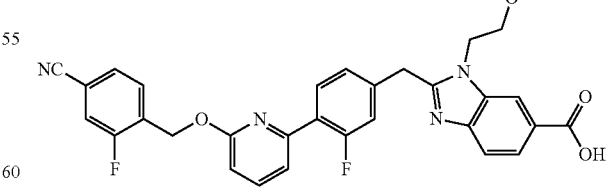

¹H NMR (400 MHz, MeOD-d₄) δ 8.63 (s, 1H), 8.30-8.27 (dd, 1H), 8.08-8.03 (t, 1H), 7.85-7.81 (m) 2H), 7.75-7.71 (t, 1H), 7.62-7.52 (m, 3H), 7.36-7.33 (d, 2H), 6.95-6.91 (d, 1H), 5.52 (s, 2H), 4.88-4.86 (m, 2H), 4.81 (s, 2H), 3.92-3.84 (t, 2H), 3.33 (s, 3H)

Example 39: Preparation of 2-((3'-(4-chloro-2-fluorobenzyloxy)-2-fluorobiphenyl-4-yl)methyl)-1-(2-methoxyethyl)-1H-benzo[d]imidazole-6-carboxylic acid

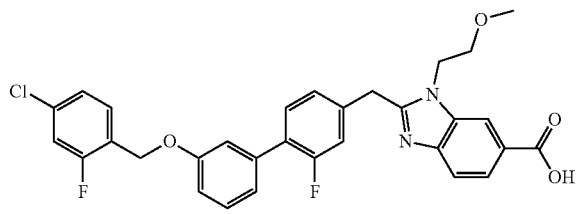 [SMILES: COCCn1c(Cc2ccc(-c3cccc(OCc4ccc(Cl)cc4F)c3)c(F)c2)nc2ccc(C(=O)O)cc21]

¹H NMR (400 MHz, CDCl₃) δ 8.52 (s, 1H), 8.22-8.19 (dd, 1H), 7.80-7.77 (d, 1H), 7.58-7.54 (m, 2H), 7.43-7.39 (t, 1H), 7.29-7.25 (m, 4H), 7.19-7.17 (m, 2H), 7.08-7.06 (m, 1H), 5.18 (s, 2H), 4.77-4.75 (t, 2H), 4.71 (s, 2H), 3.81-3.79 (t, 2H), 3.30 (s, 3H)

Example 40: Preparation of 2-((3'-(4-cyano-2-fluorobenzyloxy)-2-fluorobiphenyl-4-yl)methyl)-1-(2-methoxyethyl)-1H-benzo[d]imidazole-6-carboxylic acid

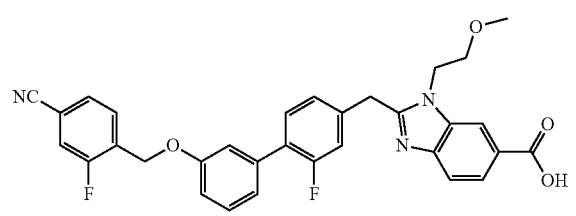 [SMILES: COCCn1c(Cc2ccc(-c3cccc(OCc4ccc(C#N)cc4F)c3)c(F)c2)nc2ccc(C(=O)O)cc21]

¹H NMR (400 MHz, MeOD-d₄) δ 8.33 (s, 1H), 8.06-8.04 (dd, 1H), 7.80-7.69 (m, 3H), 7.64-7.61 (m) 1H), 7.52-7.48 (m, 1H), 7.42-7.38 (m, 1H), 7.21-7.17 (m, 4H), 7.07-7.05 (m, 1H), 5.31-5.26 (m, 2H), 4.57-4.53 (m, 4H), 3.71-3.68 (t, 2H), 3.27 (s, 3H)

Example 41: Preparation of (R)-2-((3'-(4-chloro-2-fluorobenzyloxy)-3-fluorobiphenyl-4-yl)methyl)-1-((tetrahydrofuran-2-yl)methyl)-1H-benzo[d]imidazole-6-carboxylic acid

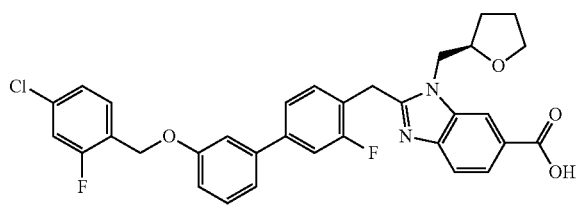 [SMILES: O=C(O)c1ccc2nc(Cc3ccc(-c4cccc(OCc5ccc(Cl)cc5F)c4)c(F)c3)n(C[C@H]3CCCO3)c2c1]

¹H NMR (400 MHz, DMSO-d₆) δ 8.21 (s, 1H), 7.80-7.77 (dd, 1H), 7.66-7.60 (m, 3H), 7.54-7.51 (m, 2H), 7.43-7.31 (m, 5H), 7.07-7.04 (m, 1H), 5.23 (s, 2H), 4.56-4.33 (m, 4H), 4.18-4.13 (m, 1H), 3.82-3.77 (q, 1H), 3.77-3.61 (q, 1H), 2.10-2.04 (m, 1H), 1.88-1.79 (m, 2H), 1.66-1.58 (m, 1H)

Example 42: Preparation of (R)-2-((3'-(4-chloro-2-fluorobenzyloxy)-2-fluorobiphenyl-4-yl)methyl)-1-((tetrahydrofuran-2-yl)methyl)-1H-benzo[d]imidazole-6-carboxylic acid

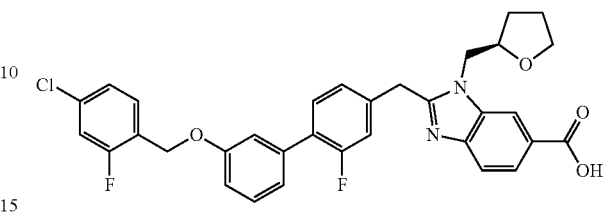

¹H NMR (400 MHz, DMSO-d₆) δ 8.21 (s, 1H), 7.81-7.79 (dd, 1H), 7.64-7.60 (m, 2H), 7.53-7.49 (m) 2H), 7.43-7.24 (m, 4H), 7.18-7.14 (m, 2H), 7.08-7.06 (dd, 1H), 5.19 (s, 2H), 4.53-4.30 (m, 4H), 4.10-4.08 (m, 1H), 3.80-3.75 (q, 1H), 3.63-3.58 (q, 1H), 2.07-2.03 (m, 1H), 1.88-1.78 (m, 2H), 1.63-1.61 (m, 1H)

Example 43: Preparation of 2-(4-(6-(4-chloro-2-fluorobenzyloxy)pyridin-2-yl)-2-fluorobenzyl)-1-(2-fluoroethyl)-1H-benzo[d]imidazole-6-carboxylic acid

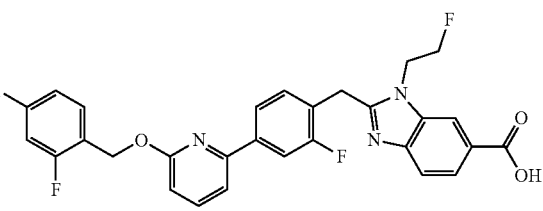

¹H NMR (400 MHz, DMSO-d₆) δ 8.20 (s, 1H), 7.96-7.89 (m, 2H), 7.87-7.79 (m, 2H), 7.68-7.55 (m) 3H), 7.52-7.42 (m, 2H), 7.36-7.30 (d, 1H), 6.89-6.87 (d, 1H), 5.53 (s, 2H), 4.83-4.78 (m, 2H), 4.71 (s, 2H), 4.41 (s, 2H)

Example 44: Preparation of 2-(4-(6-(4-cyano-2-fluorobenzyloxy)pyridin-2-yl)-2-fluorobenzyl)-1-(2-fluoroethyl)-1H-benzo[d]imidazole-6-carboxylic acid

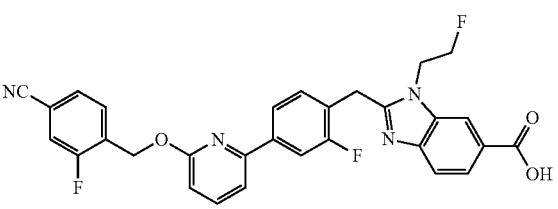 [SMILES: N#Cc1ccc(COc2cccc(-c3ccc(Cc4nc5ccc(C(=O)O)cc5n4CCF)c(F)c3)n2)c(F)c1]

¹H NMR (400 MHz, DMSO-d₆) δ 8.18 (s, 1H), 7.94-7.83 (m, 4H), 7.80-7.72 (m, 3H), 7.70-7.66 (d) 1H), 7.52-7.42 (m, 1H), 6.94-6.92 (d, 1H), 5.62 (s, 2H), 4.83-4.77 (m, 2H), 4.71 (s, 2H), 4.41 (s, 2H)

Example 45: Preparation of (R)-2-(4-(6-((4-chloro-2-fluorophenoxy)methyl)pyridin-2-yl)-2-fluorobenzyl)-1-((tetrahydrofuran-2-yl)methyl)-1H-benzo[d]imidazole-6-carboxylic acid

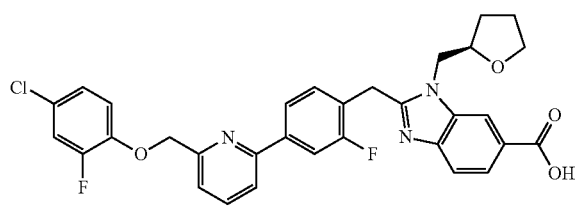 [SMILES: O=C(O)c1ccc2nc(Cc3ccc(-c4cccc(COc5ccc(Cl)cc5F)n4)cc3F)n(C[C@H]3CCCO3)c2c1]

$^1$H NMR (400 MHz, CDCl$_3$) δ 8.26 (s, 1H), 8.02-7.91 (m, 4H), 7.80-7.78 (dd) 1H), 7.60-7.58 (d, 1H), 7.52-7.44 (m, 3H), 7.36-7.31 (t, 1H), 7.24-7.21 (m, 1H), 5.37 (s, 2H), 4.57-4.34 (m, 4H), 4.19-4.15 (m, 1H), 3.82-3.77 (q, 1H), 3.66-3.61 (q, 1H), 2.10-2.04 (m, 1H), 1.89-1.80 (m, 2H), 1.67-1.63 (m, 1H)

Example 46: Preparation of (R)-2-((3'-(4-cyano-2-fluorobenzyloxy)-3-fluorobiphenyl-4-yl)methyl)-1-((tetrahydrofuran-2-yl)methyl)-1H-benzo[d]imidazole-6-carboxylic acid

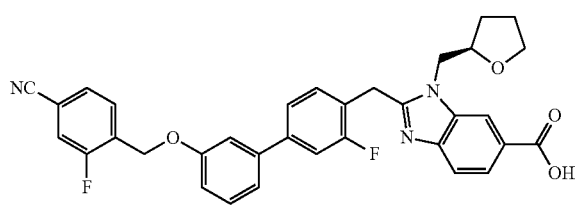 [SMILES: N#Cc1ccc(COc2cccc(-c3ccc(Cc4nc5ccc(C(=O)O)cc5n4C[C@H]4CCCO4)c(F)c3)c2)c(F)c1]

$^1$H NMR (400 MHz, DMSO-d$_6$) δ 8.21 (s, 1H), 8.08-7.93 (m, 1H), 7.83-7.67 (m, 4H), 7.61-7.51 (m) 3H), 7.44-7.39 (m, 3H), 7.35-7.32 (m, 1H), 7.08-7.06 (m, 1H), 5.35-5.30 (m, 2H), 4.56-4.35 (m, 4H), 4.16-4.14 (m, 1H), 3.82-3.77 (q, 1H), 3.66-3.62 (q, 1H), 2.10-2.05 (m, 1H), 1.88-1.80 (m, 2H), 1.67-1.60 (m, 1H)

Example 47: Preparation of (R)-2-((3'-(4-cyano-2-fluorobenzyloxy)-2-fluorobiphenyl-4-yl)methyl)-1-((tetrahydrofuran-2-yl)methyl)-1H-benzo[d]imidazole-6-carboxylic acid

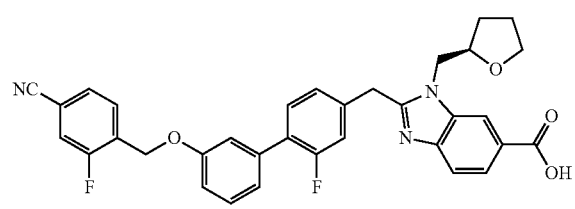 [SMILES: N#Cc1ccc(COc2cccc(-c3ccc(Cc4nc5ccc(C(=O)O)cc5n4C[C@H]4CCCO4)cc3F)c2)c(F)c1]

$^1$H NMR (400 MHz, DMSO-d$_6$) δ 8.20 (s, 1H), 8.08-7.92 (m, 1H), 7.81-7.61 (m, 5H), 7.58-7.49 (m) 2H), 7.43-7.39 (m, 1H), 7.31-7.24 (m, 2H), 7.21-7.13 (m, 2H), 7.12-7.07 (m, 1H), 5.30-5.25 (m, 2H), 4.53-4.50 (m, 2H), 4.43 (s, 2H), 4.39-4.32 (m, 1H), 4.14-4.10 (m, 1H), 3.80-3.75 (q, 1H), 3.63-3.58 (q, 1H), 2.09-2.00 (m, 1H), 1.79-1.77 (m, 2H), 1.62-1.58 (m, 1H)

Example 48: Preparation of 2-((3'-(4-chloro-2-fluorobenzyloxy)-3,5-difluorobiphenyl-4-yl)methyl)-1-(2-methoxyethyl)-1H-benzo[d]imidazole-6-carboxylic acid

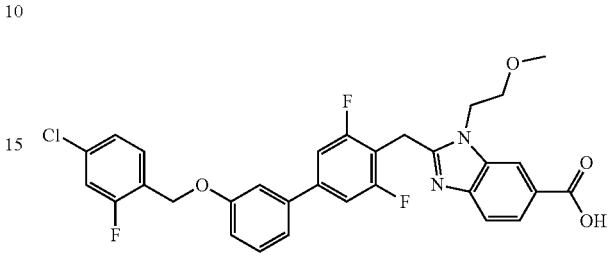

$^1$H NMR (400 MHz, CDCl$_3$) δ 8.19 (s, 1H), 8.09-8.07 (m, 1H), 7.91-7.89 (m) 1H), 7.49-7.45 (t, 1H), 7.35-7.32 (t, 1H), 7.19-7.10 (m, 6H), 6.99-6.96 (m, 1H), 5.12 (s, 2H), 4.62 (br s, 2H), 4.47-4.45 (m, 2H), 3.73-3.70 (t, 2H), 3.29 (s, 3H)

Example 49: Preparation of 2-(4-(6-(4-chloro-2-fluorobenzyloxy)pyridin-2-yl)-2-fluorobenzyl)-1-(thiophen-2-ylmethyl)-1H-benzo[d]imidazole-6-carboxylic acid

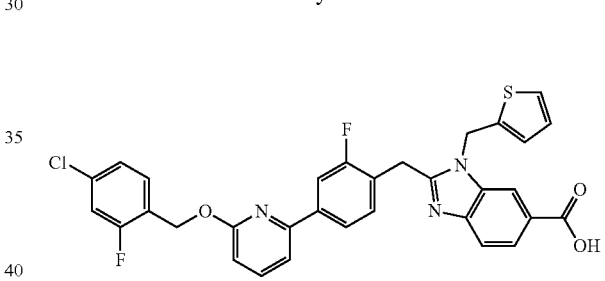

$^1$H NMR (400 MHz, DMSO-d$_6$) δ 8.25 (s, 1H), 7.91-7.79 (m, 4H), 7.66-7.60 (m, 3H), 7.51-7.48 (dd) 1H), 7.46-7.41 (m, 2H), 7.34-7.31 (m, 1H), 7.14-7.13 (d, 1H), 7.00-6.97 (t, 1H), 6.90-6.87 (d, 1H), 5.88 (s, 2H), 5.52 (s, 2H), 4.47 (s, 2H)

Example 50: Preparation of 2-(4-(6-(4-chloro-2-fluorobenzyloxy)pyridin-2-yl)-3-fluorobenzyl)-1-(thiophen-2-ylmethyl)-1H-benzo[d]imidazole-6-carboxylic acid

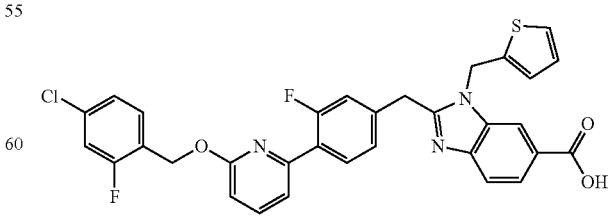

$^1$H NMR (400 MHz, DMSO-d$_6$) δ 8.26 (s, 1H), 7.94-7.90 (t, 1H), 7.86-7.81 (m, 2H), 7.68-7.66 (d, 1H), 7.64-7.58 (t, 1H), 7.51-7.48 (dd, 1H), 7.43-7.40 (m, 2H), 7.33-7.25 (m,

3H), 7.07-7.06 (d, 1H), 6.96-6.93 (m, 1H), 6.90-6.88 (d, 1H), 5.86 (s, 2H), 5.47 (s, 2H), 4.49 (s, 2H)

Example 51: Preparation of (R)-2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid

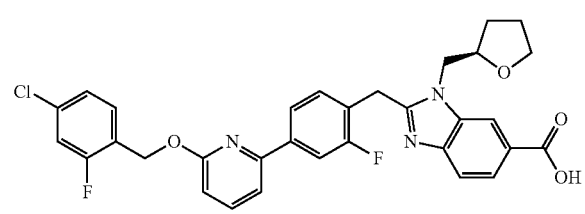 [SMILES: O=C(O)c1ccc2nc(Cc3ccc(-c4cccc(OCc5ccc(Cl)cc5F)n4)cc3F)n(C[C@H]3CCCO3)c2c1]

$^1$H NMR (400 MHz, DMSO-d$_6$) δ 8.23 (s, 1H), 7.94-7.78 (m, 4H), 7.66-7.58 (m, 3H), 7.52-7.43 (m, 2H), 7.34-7.31 (dd, 1H), 6.90-6.88 (d, 1H), 5.52 (s, 2H), 4.58-4.37 (m, 4H), 4.19-4.13 (m, 1H), 3.82-3.77 (q, 1H), 3.66-3.60 (q, 1H), 2.10-2.04 (m, 1H), 1.89-1.78 (m, 2H), 1.67-1.60 (m, 1H)

Example 52: Preparation of (R)-2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid

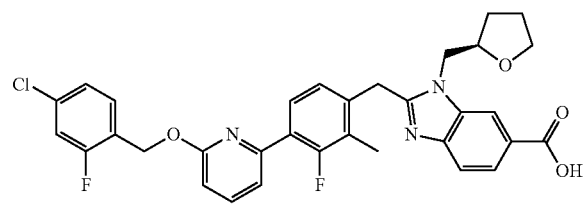 [SMILES: Cc1c(Cc2nc3ccc(C(=O)O)cc3n2C[C@H]2CCCO2)ccc(-c2cccc(OCc3ccc(Cl)cc3F)n2)c1F]

$^1$H NMR (400 MHz, DMSO-d$_6$) δ 8.21 (s, 1H), 7.98-7.94 (t, 1H), 7.89-7.79 (m, 2H), 7.64-7.58 (m, 2H), 7.53-7.43 (m, 2H), 7.34-7.29 (m, 3H), 6.91-6.89 (d, 1H), 5.47 (s, 2H), 4.54-4.31 (m, 4H), 4.13-4.07 (m, 1H), 3.80-3.75 (q, 1H), 3.63-3.58 (q, 1H), 2.09-2.00 (m, 1H), 1.88-1.78 (m, 2H), 1.65-1.58 (m, 1H)

Example 53: Preparation of 2-(4-(6-(4-chloro-2-fluorobenzyloxy)pyridin-2-yl)-2-methylbenzyl)-1-(2-methoxyethyl)-1H-benzo[d]imidazole-6-carboxylic acid

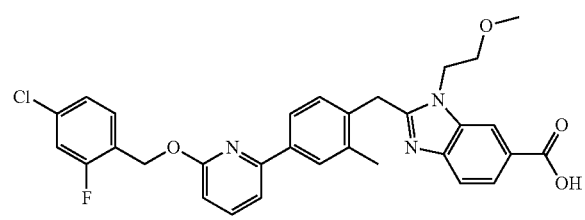 [SMILES: COCCn1c(Cc2ccc(-c3cccc(OCc4ccc(Cl)cc4F)n3)cc2C)nc2ccc(C(=O)O)cc21]

$^1$H NMR (400 MHz, MeOD-d$_4$) δ 8.61 (s, 1H), 8.27-8.25 (d, 1H), 8.04 (s, 1H), 7.97-7.95 (d) 1H), 7.80-7.76 (m, 2H), 7.57-7.53 (m, 2H), 7.35-7.33 (m, 2H), 7.26-7.21 (m, 2H), 6.85-6.83 (d, 1H), 5.56 (s, 2H), 4.86-4.85 (m, 2H), 4.79 (s, 2H), 3.88-3.87 (m, 2H), 3.33 (s, 3H), 2.41 (s, 3H)

Example 54: Preparation of 2-(4-(6-(4-cyano-2-fluorobenzyloxy)pyridin-2-yl)-2-methylbenzyl)-1-(2-methoxyethyl)-1H-benzo[d]imidazole-6-carboxylic acid

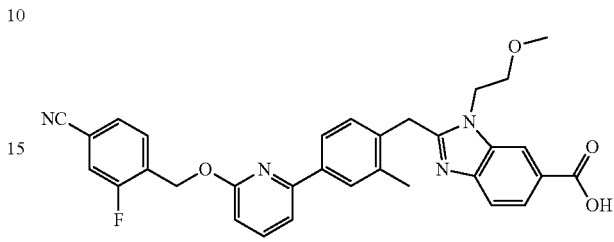

$^1$H NMR (400 MHz, DMSO-d$_6$) δ 8.19 (s, 1H), 8.05-7.65 (m, 7H), 7.59-7.52 (m, 2H), 7.17-7.15 (d, 1H), 6.88-6.84 (m, 1H), 5.61-5.57 (m, 2H), 4.51 (s, 2H), 4.38 (s, 2H), 3.63 (s, 2H), 3.20 (s, 3H), 2.33 (s, 3H)

Example 55: Preparation of 2-(4-(6-(4-chloro-2-fluorobenzyloxy)pyridin-2-yl)-3-fluorobenzyl)-1-(2-fluoroethyl)-1H-benzo[d]imidazole-6-carboxylic acid

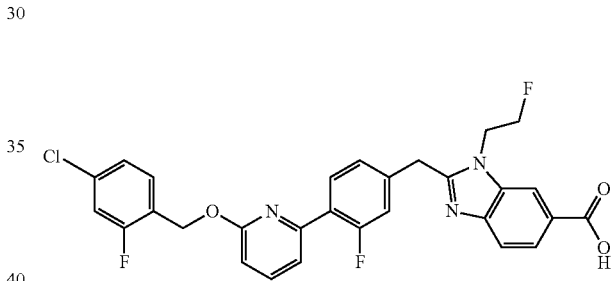

$^1$H NMR (400 MHz, MeOD-d$_4$) δ 8.39 (s, 1H), 8.11-8.04 (m, 2H), 7.78-7.74 (m, 2H), 7.56-7.47 (m) 2H), 7.29-7.20 (m, 4H), 6.85-6.83 (d, 1H), 5.50 (s, 2H), 4.93-4.81 (m, 2H), 4.76-4.72 (m, 2H), 4.59 (s, 2H)

Example 56: Preparation of 2-((3'-(4-chloro-2-fluorobenzyloxy)-3-fluorobiphenyl-4-yl)methyl)-1-(2-fluoroethyl)-1H-benzo[d]imidazole-6-carboxylic acid

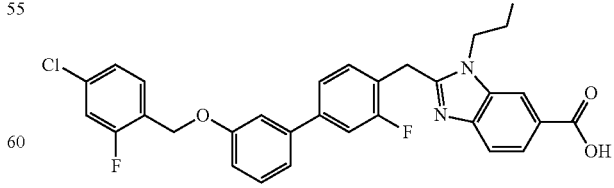

$^1$H NMR (400 MHz, DMSO-d$_6$) δ 8.19 (s, 1H), 7.82-7.79 (d, 1H), 7.68-7.57 (m, 3H), 7.56-7.50 (m, 2H), 7.47-7.30 (m, 5H), 7.07-7.04 (d, 1H), 5.23 (s, 2H), 4.84-4.83 (m, 2H), 4.80 (s, 2H), 4.40 (s, 2H)

Example 57: Preparation of 2-((3'-(4-cyano-2-fluorobenzyloxy)-3-fluorobiphenyl-4-yl)methyl)-1-(2-fluoroethyl)-1H-benzo[d]imidazole-6-carboxylic acid

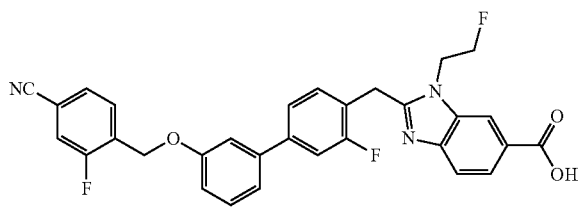 [SMILES: N#Cc1ccc(COc2cccc(-c3ccc(Cc4nc5ccc(C(=O)O)cc5n4CCF)c(F)c3)c2)c(F)c1]

¹H NMR (400 MHz, DMSO-d₆) δ 8.22 (s, 1H), 7.96-7.93 (d, 1H), 7.87-7.79 (m, 3H), 7.61-7.59 (d, 2H), 7.59-7.58 (d, 1H), 7.47-7.44 (m, 3H), 7.35-7.33 (d, 1H), 7.09-7.07 (d, 1H), 5.35 (s, 2H), 4.84-4.83 (m, 2H), 4.80 (s, 2H), 4.40 (s, 2H)

Example 58: Preparation of 2-(4-(6-(4-cyano-2-fluorobenzyloxy)pyridin-2-yl)-3-fluorobenzyl)-1-(2-fluoroethyl)-1H-benzo[d]imidazole-6-carboxylic acid

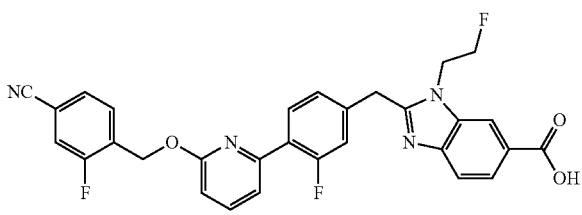 [SMILES: N#Cc1ccc(COc2cccc(-c3ccc(Cc4nc5ccc(C(=O)O)cc5n4CCF)cc3F)n2)c(F)c1]

¹H NMR (400 MHz, DMSO-d₆) δ 8.21 (s, 1H), 7.99-7.81 (m, 4H), 7.77-7.72 (m, 2H), 7.67-7.64 (d, 1H), 7.50-7.45 (m, 2H), 7.33-7.27 (m, 2H), 6.95-6.93 (d, 1H), 5.57 (s, 2H), 4.77-4.66 (m, 2H), 4.43 (s, 2H)

Example 59: Preparation of (S)-2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid

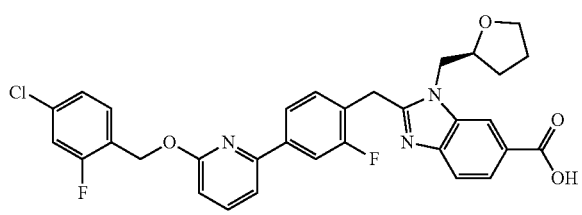 [SMILES: O=C(O)c1ccc2nc(Cc3ccc(-c4cccc(OCc5ccc(Cl)cc5F)n4)cc3F)n(C[C@@H]3CCCO3)c2c1]

¹H NMR (400 MHz, MeOD-d₄) δ 8.21 (s, 1H), 7.93-7.77 (m, 4H), 7.66-7.57 (m, 3H), 7.51-7.42 (m) 2H), 7.33-7.30 (dd, 1H), 6.90 (d, 1H), 5.52 (s, 2H), 4.56-4.33 (m, 4H), 4.19-4.13 (m, 1H), 3.82-3.77 (q, 1H), 3.66-3.60 (q, 1H), 2.10-2.05 (m, 1H), 1.88-1.79 (m, 2H), 1.69-1.58 (m, 1H)

Example 61: Preparation of 2-(4-(6-(4-chloro-2-fluorobenzyloxy)pyridin-2-yl)-2,3-difluorobenzyl)-1-((tetrahydrofuran-2-yl)methyl)-1H-benzo[d]imidazole-6-carboxylic acid

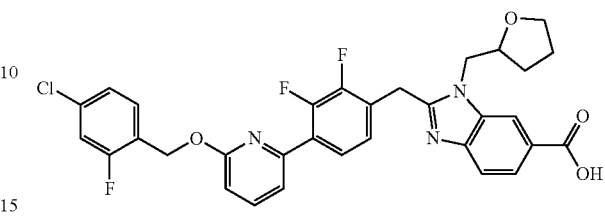

¹H NMR (400 MHz, DMF-d₆) δ 8.41 (s, 1H), 8.34-8.30 (m, 2H), 8.23-8.19 (t, 1H), 8.11-8.09 (d, 1H), 8.05-8.01 (t, 1H), 7.93-7.91 (d, 2H), 7.79-7.74 (m, 2H), 7.40-7.38 (d, 1H), 5.90 (s, 2H), 5.11-5.04 (m, 4H), 4.94-4.88 (m, 2H), 4.63-4.61 (m, 2H), 4.50-4.40 (m, 2H), 4.25-4.20 (q, 1H), 4.09-4.03 (q, 1H), 2.56-2.49 (m, 1H), 2.33-2.24 (m, 2H), 2.12-2.05 (m, 1H)

Example 62: Preparation of 2-(4-(6-(4-cyano-2-fluorobenzyloxy)pyridin-2-yl)-2,3-difluorobenzyl)-1-((tetrahydrofuran-2-yl)methyl)-1H-benzo[d]imidazole-6-carboxylic acid

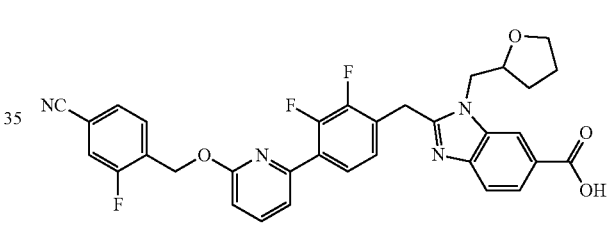

¹H NMR (400 MHz, MeOD-d₄) δ 8.49 (s, 1H), 8.16-8.14 (d, 1H), 7.87-7.70 (m, 4H), 7.66-7.57 (m) 2H), 7.53-7.50 (d, 1H), 7.30-7.27 (t, 1H), 6.97-6.95 (d, 1H), 5.62 (s, 2H), 4.81-4.70 (m, 3H), 4.57-4.51 (m, 1H), 4.33-4.28 (m, 1H), 3.98-3.90 (m, 1H), 3.79-3.70 (m, 1H), 2.27-2.20 (m, 1H), 2.00-1.95 (m, 2H), 1.81-1.76 (m, 1H)

Example 63: Preparation of 2-(4-(6-(4-chloro-2-fluorobenzyloxy)pyridin-2-yl)-2-methoxybenzyl)-1-((tetrahydrofuran-2-yl)methyl)-1H-benzo[d]imidazole-6-carboxylic acid

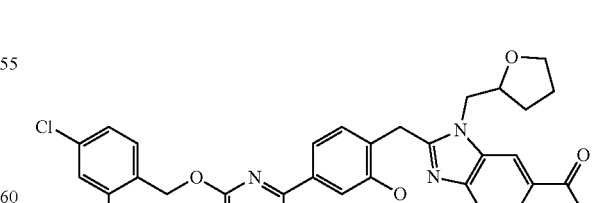

¹H NMR (400 MHz, DMSO-d₆) δ 8.41 (s, 1H), 7.97-7.95 (d, 1H), 7.85-7.81 (t, 1H), 7.72-7.64 (m, 4H), 7.61-7.57 (t, 1H), 7.51-7.48 (dd, 1H), 7.39-7.37 (d, 1H), 7.33-7.30 (d, 1H), 6.89-6.87 (d, 1H), 5.34 (s, 2H), 4.68-4.43 (m, 4H), 4.16-4.13 (m, 1H), 3.86-3.76 (m, 4H), 3.67-3.61 (q, 1H), 3.48-3.38 (q, 1H), 2.12-2.04 (m, 1H), 1.94-1.79 (m, 2H), 1.71-1.62 (m, 1H)

Example 64: Preparation of 2-(4-(6-(4-cyano-2-fluorobenzyloxy)pyridin-2-yl)-2-methoxybenzyl)-1-((tetrahydrofuran-2-yl)methyl)-1H-benzo[d]imidazole-6-carboxylic acid

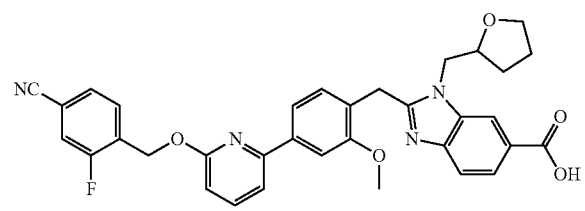 [SMILES: COc1cc(-c2cccc(OCc3ccc(C#N)cc3F)n2)ccc1Cc1nc2ccc(C(=O)O)cc2n1CC1CCCO1]

$^1$H NMR (400 MHz, MeOD-d$_4$) δ 8.58 (s, 1H), 8.25-8.23 (d, 1H), 7.84-7.75 (m, 2H), 7.75-7.72 (m, 3H), 7.69-7.55 (m, 2H), 7.50-7.48 (d, 1H), 6.92-6.89 (d, 2H), 5.68 (s, 2H), 4.75-4.58 (m, 4H), 4.29-4.24 (m, 1H), 3.99-3.91 (m, 1H), 3.86 (s, 3H), 3.80-3.74 (m, 1H), 2.26-2.17 (m, 1H), 2.05-1.93 (m, 2H), 1.83-1.74 (m, 1H)

Example 65: Preparation of 2-(4-(6-(4-chloro-2-fluorobenzyloxy)pyridin-2-yl)-2,6-difluorobenzyl)-1-((tetrahydrofuran-2-yl)methyl)-1H-benzo[d]imidazole-6-carboxylic acid

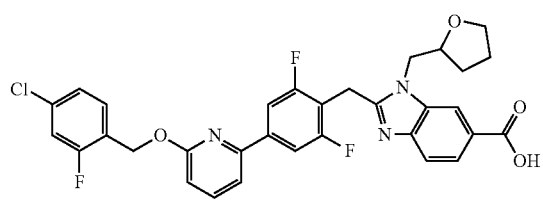 [SMILES: O=C(O)c1ccc2nc(Cc3c(F)cc(-c4cccc(OCc5ccc(Cl)cc5F)n4)cc3F)n(CC3CCCO3)c2c1]

$^1$H NMR (400 MHz, CDCl$_3$) δ 8.16 (s, 1H), 7.99-7.96 (dd, 2H), 7.76-7.74 (d, 13H), 7.65-7.57 (m, 3H), 7.47-7.43 (t, 1H), 7.27-7.25 (m, 2H), 7.14-7.11 (d, 2H), 6.78-6.76 (d, 1H), 4.49-4.42 (m, 3H), 4.34-4.24 (m, 2H), 3.94-3.88 (q, 1H), 3.80-3.75 (q, 1H), 2.17-2.05 (m, 1H), 1.96-1.86 (m, 2H), 1.69-1.62 (m, 1H)

Example 66: Preparation of (S)-2-(4-(6-(4-cyano-2-fluorobenzyloxy)pyridin-2-yl)-2-fluorobenzyl)-1-((tetrahydrofuran-2-yl)methyl)-1H-benzo[d]imidazole-6-carboxylic acid

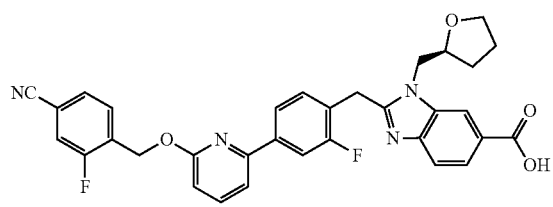 [SMILES: N#Cc1ccc(COc2cccc(-c3ccc(Cc4nc5ccc(C(=O)O)cc5n4C[C@@H]4CCCO4)c(F)c3)n2)c(F)c1]

$^1$H NMR (400 MHz, DMSO-d$_6$) δ 8.21 (s, 1H), 7.94-7.79 (m, 4H), 7.79-7.72 (m, 3H), 7.72-7.65 (d, 1H), 7.59-7.56 (d, 1H), 7.45-7.41 (t, 1H), 6.94-6.92 (d, 1H), 5.62 (s, 2H), 4.57-4.33 (m, 4H), 4.18-4.12 (m, 1H), 3.82-3.76 (q, 1H), 3.65-3.60 (q, 1H), 2.11-2.03 (m, 1H), 1.88-1.66 (m, 2H), 1.66-1.58 (m, 1H)

Example 67: Preparation of (S)-2-(4-(6-(4-cyano-2-fluorobenzyloxy)pyridin-2-yl)-3-fluorobenzyl)-1-((tetrahydrofuran-2-yl)methyl)-1H-benzo[d]imidazole-6-carboxylic acid

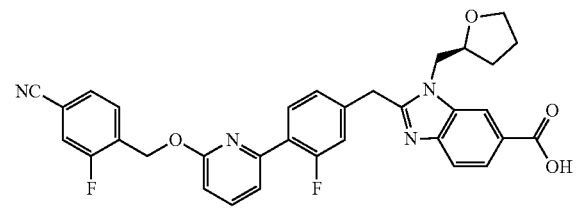 [SMILES: N#Cc1ccc(COc2cccc(-c3ccc(Cc4nc5ccc(C(=O)O)cc5n4C[C@@H]4CCCO4)cc3F)n2)c(F)c1]

$^1$H NMR (400 MHz, DMSO-d$_6$) δ 8.21 (s, 1H), 7.95-7.84 (m, 4H), 7.81-7.79 (dd, 1H), 7.77-7.71 (m, 1H), 7.64-7.61 (d, 1H), 7.48-7.44 (m, 1H), 7.32-7.28 (m, 2H), 6.95-6.93 (d, 1H), 5.57 (s, 2H), 4.53-4.44 (m, 3H), 4.36-4.34 (m, 1H), 4.12-4.06 (m, 1H), 3.80-3.74 (q, 1H), 3.63-3.57 (q, 1H), 2.09-2.01 (m, 1H), 1.89-1.74 (m, 2H), 1.65-1.57 (m, 1H)

Example 68: Preparation of 2-(4-(6-(4-cyano-2-fluorobenzyloxy)pyridin-2-yl)-2-methylbenzyl)-1-((tetrahydrofuran-2-yl)methyl)-1H-benzo[d]imidazole-6-carboxylic acid

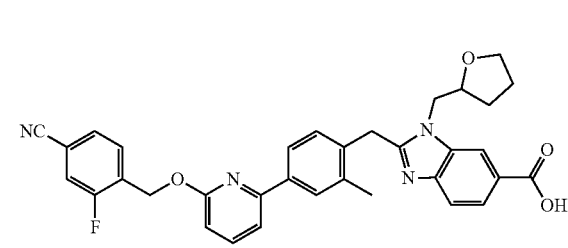 [SMILES: Cc1cc(-c2cccc(OCc3ccc(C#N)cc3F)n2)ccc1Cc1nc2ccc(C(=O)O)cc2n1CC1CCCO1]

$^1$H NMR (400 MHz, DMSO-d$_6$) δ 8.20 (s, 1H), 7.94-7.71 (m, 5H), 7.58-7.51 (m, 2H), 7.18-7.16 (d, 1H), 6.94-6.84 (m, 1H), 5.61 (s, 2H), 4.50-4.44 (d, 1H), 4.39 (s, 2H), 4.33-4.27 (m, 1H), 3.86-3.78 (m, 1H), 3.69-3.61 (m, 1H), 2.33 (s, 3H), 2.09-2.00 (m, 1H), 1.91-1.80 (m, 2H), 1.65-1.58 (m, 1H)

Example 69: Preparation of 2-(4-(6-(4-chloro-2-fluorobenzyloxy)pyridin-2-yl)-2-methylbenzyl)-1-((tetrahydrofuran-2-yl)methyl)-1H-benzo[d]imidazole-6-carboxylic acid

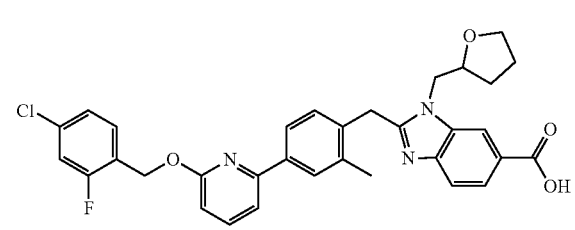 [SMILES: Cc1cc(-c2cccc(OCc3ccc(Cl)cc3F)n2)ccc1Cc1nc2ccc(C(=O)O)cc2n1CC1CCCO1]

¹H NMR (400 MHz, DMF-d₆) δ 8.62 (s, 1H), 8.32 (s, 1H), 8.26-8.19 (m, 3H), 8.05-7.98 (m, 3H), 7.93-7.90 (d, 1H), 7.75-7.73 (d, 1H), 7.26-7.24 (d, 1H), 5.94 (s, 2H), 4.89-4.70 (m, 4H), 4.58-4.52 (m, 1H), 4.25-4.22 (q, 1H), 4.08-4.03 (q, 1H), 2.52-2.45 (m, 1H), 2.33-2.21 (m, 2H), 2.19-2.07 (m, 1H)

Example 70: Preparation of 2-(4-(6-(4-chloro-2-fluorobenzyloxy)pyridin-2-yl)-2,5-difluorobenzyl)-1-((tetrahydrofuran-2-yl)methyl)-1H-benzo[d]imidazole-6-carboxylic acid

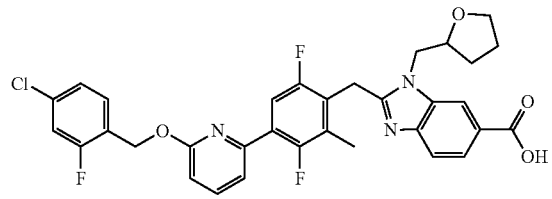 [SMILES: Cc1c(F)c(-c2cccc(OCc3ccc(Cl)cc3F)n2)cc(F)c1Cc1nc2ccc(C(=O)O)cc2n1CC1CCCO1]

¹H NMR (400 MHz, MeOD-d₄) δ 8.24 (s, 1H), 7.99-7.97 (d, 1H), 7.85-7.80 (m, 1H), 7.73-7.71 (d, 1H), 7.68-7.66 (d, 1H), 7.53-7.49 (m, 2H), 7.21-7.18 (m, 2H), 7.12-7.08 (d, 1H), 6.84-6.82 (d, 1H), 5.51 (s, 2H), 4.51-4.42 (m, 3H), 4.34-4.24 (m, 2H), 3.90-3.85 (q, 1H), 3.76-3.71 (q, 1H), 2.19-2.14 (m, 1H), 2.03-1.89 (m, 2H), 1.72-1.67 (m, 1H)

Example 71: Preparation of 2-(4-(6-(4-cyano-2-fluorobenzyloxy)pyridin-2-yl)-2,5-difluorobenzyl)-1-((tetrahydrofuran-2-yl)methyl)-1H-benzo[d]imidazole-6-carboxylic acid

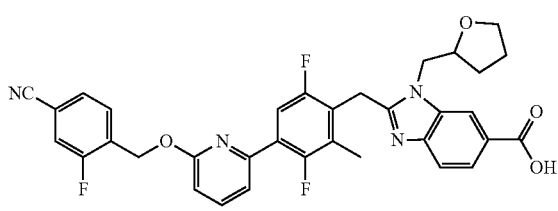 [SMILES: Cc1c(F)c(-c2cccc(OCc3ccc(C#N)cc3F)n2)cc(F)c1Cc1nc2ccc(C(=O)O)cc2n1CC1CCCO1]

¹H NMR (400 MHz, DMF-d₆) δ 8.65 (s, 1H), 8.36-8.32 (m, 2H), 8.20-8.12 (m, 4H), 8.08-8.00 (m, 1H), 7.96-7.94 (d, 1H), 7.83-7.78 (m, 1H), 7.42-7.40 (d, 1H), 6.02 (s, 2H), 5.00-4.92 (m, 1H), 4.88-4.78 (m, 2H), 4.60-4.58 (m, 1H), 4.30-4.29 (d, 1H), 4.23-4.20 (m, 1H), 4.08-4.02 (m, 1H), 2.53-2.47 (m, 1H), 2.33-2.21 (m, 2H), 2.11-2.03 (m, 1H)

Example 72: Preparation of 2-(4-(6-(4-chloro-2-fluorobenzyloxy)pyridin-2-yl)-2-fluorobenzyl)-1-((1-ethyl-1H-imidazole-5-yl)methyl)-1H-benzo[d]imidazole-6-carboxylic acid

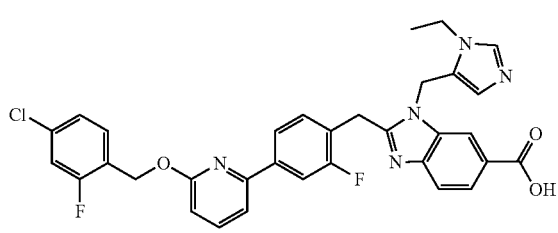 [SMILES: CCn1cncc1Cn1c(Cc2ccc(-c3cccc(OCc4ccc(Cl)cc4F)n3)cc2F)nc2ccc(C(=O)O)cc21]

¹H NMR (400 MHz, DMSO-d₆) δ 8.17 (s, 1H), 7.89-7.79 (m, 4H), 7.67-7.60 (m, 4H), 7.51-7.49 (dd, 1H), 7.43-7.39 (t, 1H), 7.34-7.32 (dd, 1H), 6.89-6.87 (d, 1H), 6.47 (s, 2H), 5.72 (s, 2H), 5.52 (s, 2H), 4.04-3.94 (q, 2H), 1.20-1.15 (t, 3H)

Example 73: Preparation of (S)-2-(4-(6-(4-cyano-2-fluorobenzyloxy)pyridin-2-yl)-2-fluorobenzyl)-1-(oxetan-2-ylmethyl)-1H-benzo[d]imidazole-6-carboxylic acid

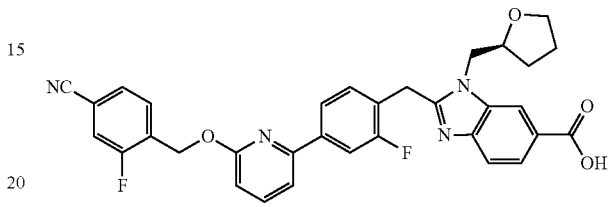

¹H NMR (400 MHz, DMSO-d₆) δ 8.25 (s, 1H), 7.94-7.83 (m, 4H), 7.80-7.72 (m, 3H), 7.67-7.66 (m, 1H), 7.59-7.57 (d, 1H), 7.45-7.41 (t, 1H), 6.94-6.90 (m, 1H), 5.62 (s, 2H), 5.05-5.03 (m, 1H), 4.76-4.70 (m, 1H), 4.58-4.45 (m, 5H), 2.72-2.68 (m, 1H), 2.40-2.34 (m, 1H)

Example 74: Preparation of (S)-2-(4-(6-(4-cyano-2-fluorobenzyloxy)pyridin-2-yl)-3-fluorobenzyl)-1-(oxetan-2-ylmethyl)-1H-benzo[d]imidazole-6-carboxylic acid

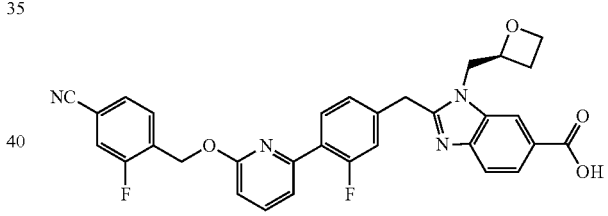

¹H NMR (400 MHz, DMSO-d₆) δ 8.24 (s, 1H), 7.93-7.84 (m, 4H) 7.82-7.79 (dd, 1H), 7.77-7.71 (m, 1H), 7.63 (d, 1H), 7.47-7.45 (m, 1H), 7.32-7.28 (m, 2H), 6.95-6.93 (d, 1H), 5.58 (s, 2H), 5.02-4.96 (m, 1H), 4.73-4.68 (m, 1H), 4.59-4.54 (m, 1H), 4.51-4.48 (m, 3H), 4.38-4.33 (m, 1H), 2.71-2.63 (m, 1H), 2.41-2.35 (m, 1H)

Example 75: Preparation of 2-(4-(6-(4-chlorobenzyloxy)pyridin-2-yl)-2-fluorobenzyl)-1-((tetrahydrofuran-2-yl)methyl)-1H-benzo[d]imidazole-6-carboxylic acid

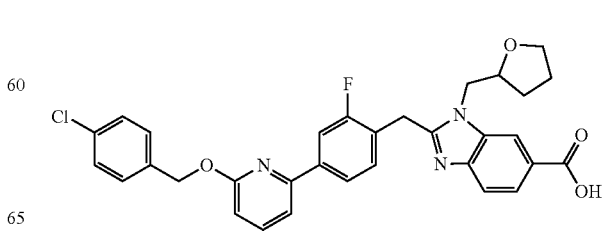

¹H NMR (400 MHz, DMSO) δ 12.97 (br s, 1H), 8.21 (s, 1H), 7.91-7.77 (m, 4H), 7.64-7.63 (d, 1H), 7.59-7.57 (d, 1H), 7.54-7.52 (d, 2H), 7.46-7.41 (m, 3H), 6.90-6.88 (d, 1H), 5.49 (s, 2H), 4.55-4.33 (m, 4H), 4.18-4.16 (m, 1H), 3.82-3.77 (m, 1H), 3.66-3.61 (m, 1H), 3.09-2.03 (m, 1H), 1.88-1.81 (m, 1H), 1.65-1.60 (m, 1H)

Example 76: Preparation of 2-(2-fluoro-4-(6-(4-methylbenzyloxy)pyridin-2-yl)benzyl)-1-((tetrahydrofuran-2-yl)methyl)-1H-benzo[d]imidazole-6-carboxylic acid

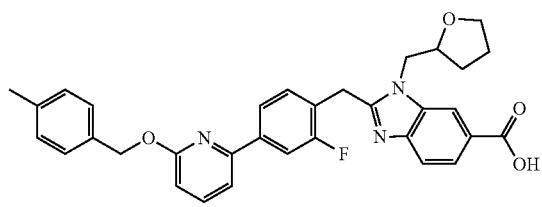 [SMILES: Cc1ccc(COc2cccc(-c3ccc(Cc4nc5ccc(C(=O)O)cc5n4CC4CCCO4)c(F)c3)n2)cc1]

¹H NMR (400 MHz, DMSO) δ 8.29 (s, 1H), 7.95-7.94 (d, 1H), 7.92 (s, 1H), 7.86-7.80 (m, 2H), 7.64-7.61 (d, 2H), 7.49-7.45 (t, 1H), 7.40-7.38 (d, 2H), 7.20-7.18 (d, 2H), 6.87-6.85 (d, 1H), 5.44 (s, 2H), 4.58-4.39 (m, 4H), 4.20-4.14 (m, 1H), 3.83-3.77 (m, 1H), 3.66-3.61 (m, 1H), 2.30 (s, 3H), 2.13-2.05 (m, 1H), 1.91-1.79 (m, 2H), 1.66-1.61 (m, 1H)

Example 77: Preparation of 2-(2-fluoro-4-(6-(4-(trifluoromethyl)benzyloxy)pyridin-2-yl)benzyl)-1-((tetrahydrofuran-2-yl)methyl)-1H-benzo[d]imidazole-6-carboxylic acid

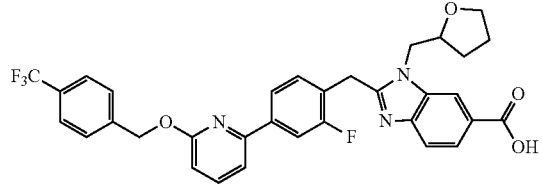 [SMILES: O=C(O)c1ccc2nc(Cc3ccc(-c4cccc(OCc5ccc(C(F)(F)F)cc5)n4)cc3F)n(CC3CCCO3)c2c1]

¹H NMR (400 MHz, DMSO) δ 8.39 (s, 1H), 7.94-7.84 (m, 4H), 7.77-7.66 (m, 6H), 7.66-7.48 (t, 1H), 6.96-6.94 (d, 1H), 5.60 (s, 2H), 4.69-4.54 (m, 4H), 4.15-4.14 (m, 1H), 3.82-3.77 (m, 1H), 3.65-3.60 (m, 1H), 2.14-2.06 (m, 1H), 1.91-1.79 (m, 2H), 1.68-1.65 (m, 1H)

Example 78: Preparation of (S)-2-(4-(6-(4-chloro-2-fluorobenzyloxy)pyridin-2-yl)-2-fluorobenzyl)-1-(oxetan-2-ylmethyl)-1H-benzo[d]imidazole-6-carboxylic acid

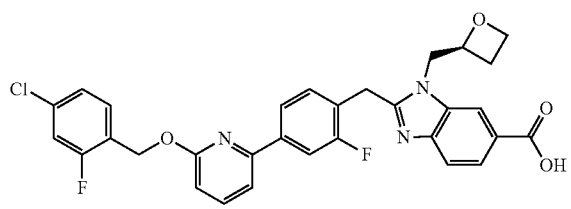 [SMILES: O=C(O)c1ccc2nc(Cc3ccc(-c4cccc(OCc5ccc(Cl)cc5F)n4)cc3F)n(C[C@@H]3CCO3)c2c1]

¹H NMR (400 MHz, DMSO) δ 8.25-8.24 (d, 1H), 7.93-7.78 (m, 4H), 7.66-7.58 (m, 3H), 7.51-7.48 (dd, 1H), 7.46-7.41 (t, 1H), 7.34-7.31 (dd, 1H), 6.90-6.87 (d, 1H), 5.56 (s, 2H), 5.07-5.02 (m, 1H), 4.76-4.70 (m, 1H), 4.62-4.33 (m, 5H), 2.73-2.66 (1H), 2.43-2.40 (m, 1H)

Example 79: Preparation of (S)-2-(4-(6-(4-chloro-2-fluorobenzyloxy)pyridin-2-yl)-3-fluorobenzyl)-1-(oxetan-2-ylmethyl)-1H-benzo[d]imidazole-6-carboxylic acid

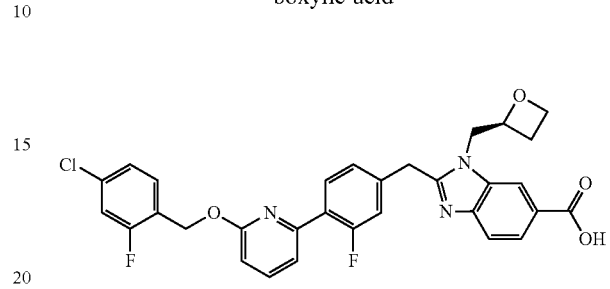

¹H NMR (400 MHz, DMSO) δ 8.25 (s, 1H), 7.98-7.94 (t, 1H), 7.86-7.80 (m, 2H), 7.65-7.58 (m, 2H), 7.50-7.43 (m, 2H), 7.33-7.29 (m, 3H), 6.90-6.88 (d, 1H), 5.47 (s, 2H), 5.02-4.96 (m, 1H), 4.74-4.68 (m, 1H), 4.60-4.39 (m, 4H), 4.37-4.33 (m, 1H), 2.71-2.63 (m, 1H), 2.40-2.32 (m, 1H)

Example 80: Preparation of 2-(2-fluoro-4-(6-(3-methylbenzyloxy)pyridin-2-yl)benzyl)-1-((tetrahydrofuran-2-yl)methyl)-1H-benzo[d]imidazole-6-carboxylic acid

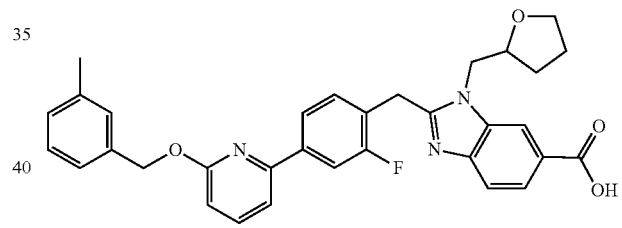

¹H NMR (400 MHz, DMSO) δ 8.15 (s, 1H), 7.91-7.88 (m, 2H), 7.84-7.76 (m, 2H), 7.63-7.61 (d, 1H), 7.52-7.50 (d, 1H), 7.44-7.40 (t, 1H), 7.33 (s, 1H), 7.30-7.24 (m, 2H), 7.14-7.12 (m, 1H), 6.88-6.86 (d, 1H), 4.52-4.30 (m, 4H), 4.19-4.15 (m, 1H), 3.82-3.77 (m, 1H), 3.66-3.60 (m, 1H), 2.32 (s, 3H), 2.11-2.03 (m, 1H), 1.90 (s, 1H), 1.88-1.78 (m, 2H), 1.67-1.65 (m, 1H)

Example 81: Preparation of 2-(2-fluoro-4-(6-(3-methoxybenzyloxy)pyridin-2-yl)benzyl)-1-((tetrahydrofuran-2-yl)methyl)-1H-benzo[d]imidazole-6-carboxylic acid

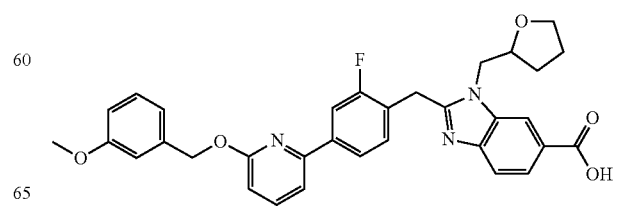

¹H NMR (400 MHz, DMSO) δ 8.21 (s, 1H), 7.94-7.88 (m, 3H), 7.84-7.77 (m, 2H), 7.64-7.57 (dd, 2H), 7.45-7.41 (dd, 1H), 7.31-7.28 (dd, 1H), 7.10-7.06 (dd, 2H), 6.89-6.86 (m, 2H), 5.46 (s, 2H), 4.56-4.50 (m, 1H), 4.45-4.42 (d, 1H), 4.38-4.33 (m, 1H), 3.82-3.74 (m, 5H), 3.74-3.55 (m, 1H), 2.10-2.05 (m, 1H), 1.88-1.81 (m, 2H), 1.65-1.61 (m, 1H)

Example 82: Preparation of (S)-2-(4-(6-(4-chloro-2-fluorobenzyloxy)pyridin-2-yl)-2,3-difluorobenzyl)-1-(oxetan-2-ylmethyl)-1H-benzo[d]imidazole-6-carboxylic acid

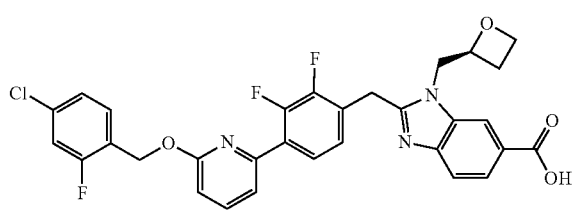 [SMILES: O=C(O)c1ccc2nc(Cc3ccc(-c4cccc(OCc5ccc(Cl)cc5F)n4)c(F)c3F)n(C[C@@H]3CCO3)c2c1]

¹H NMR (400 MHz, DMSO) δ 8.26 (s, 1H), 7.91-7.87 (dd, 1H), 7.80-7.74 (m, 2H), 7.63-7.59 (m, 2H), 7.51-7.48 (m, 2H), 7.34-7.28 (m, 2H), 6.97-6.94 (d, 1H), 5.49 (s, 2H), 5.10-5.05 (m, 1H), 4.78-4.73 (m, 1H), 4.65-4.48 (m, 4H), 4.39-4.33 (m, 1H), 2.76-2.68 (m, 1H), 2.43-2.38 (m, 1H)

Example 83: Preparation of 2-(4-(6-(benzyloxy)pyridin-2-yl)-2-fluorobenzyl)-1-((tetrahydrofuran-2-yl)methyl)-1H-benzo[d]imidazole-6-carboxylic acid

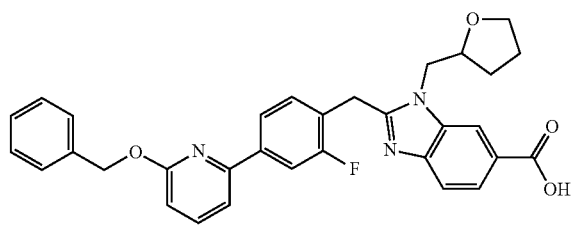 [SMILES: O=C(O)c1ccc2nc(Cc3ccc(-c4cccc(OCc5ccccc5)n4)cc3F)n(CC3CCCO3)c2c1]

¹H NMR (400 MHz, DMSO) δ 8.47 (s, 1H), 8.01-7.95 (m, 3H), 7.86-7.82 (dd, 1H), 7.76-7.73 (d, 1H), 7.67-7.65 (d, 1H), 7.57-7.37 (m, 2H), 7.34-7.30 (m, 1H), 6.91-6.89 (d, 1H), 5.49 (s, 2H), 4.74-4.51 (m, 4H), 4.21-4.15 (m, 1H), 3.83-3.78 (m, 1H), 3.66-3.60 (m, 1H), 2.15-2.07 (m, 1H), 1.94-1.82 (m, 2H), 1.70-1.67 (m, 1H)

Example 84: Preparation of (S)-2-(4-(6-(4-chloro-2-fluorobenzyloxy)pyridin-2-yl)-2,6-difluorobenzyl)-1-(oxetan-2-ylmethyl)-1H-benzo[d]imidazole-6-carboxylic acid

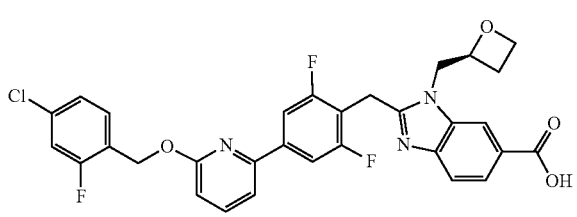 [SMILES: O=C(O)c1ccc2nc(Cc3c(F)cc(-c4cccc(OCc5ccc(Cl)cc5F)n4)cc3F)n(C[C@@H]3CCO3)c2c1]

¹H NMR (400 MHz, DMSO) δ 8.31 (s, 1H), 7.90-7.81 (m, 4H), 7.76-7.74 (d, 1H), 7.64-7.58 (m, 2H), 7.52-7.49 (m, 2H), 7.34-7.31 (m, 1H), 6.96-6.92 (m, 1H), 5.54 (s, 2H), 5.15-5.10 (m, 1H), 4.88-4.82 (m, 1H), 4.73-4.35 (m, 7H), 2.77-2.73 (m, 1H), 2.45-2.33 (m, 1H)

Example 85: Preparation of 2-(4-(6-(3,4-difluorobenzyloxy)pyridin-2-yl)-2-fluorobenzyl)-1-((tetrahydrofuran-2-yl)methyl)-1H-benzo[d]imidazole-6-carboxylic acid

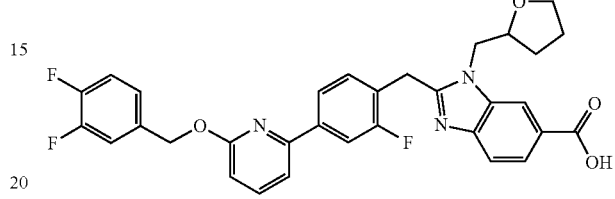

¹H NMR (400 MHz, DMSO) δ 8.38 (s, 1H), 7.95-7.91 (m, 3H), 7.87-7.83 (m, 1H), 7.69-7.66 (m, 2H), 7.61-7.56 (m, 1H), 7.52-7.42 (m, 2H), 7.37 (m, 1H), 6.92-6.90 (d, 1H), 5.48 (s, 2H), 4.68-4.45 (m, 4H), 4.18-4.17 (m, 1H), 3.83-3.77 (m, 1H), 3.66-3.60 (m, 1H), 2.12-2.06 (m, 1H), 1.91-1.79 (m, 2H), 1.67-1.65 (m, 1H)

Example 86: Preparation of (S)-2-(4-(6-(4-chloro-2-fluorobenzyloxy)pyridin-2-yl)-2,5-difluorobenzyl)-1-(oxetan-2-ylmethyl)-1H-benzo[d]imidazole-6-carboxylic acid

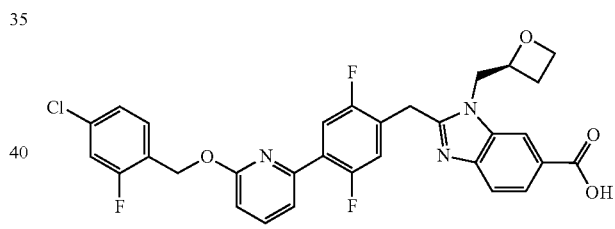

¹H NMR (400 MHz, DMSO) δ 8.26 (s, 1H), 7.90-7.78 (m, 3H), 7.62-7.59 (m, 2H), 7.53-7.49 (m, 2H), 7.41-7.37 (m, 1H), 7.34-7.32 (m, 1H), 6.96-6.94 (d, 1H), 5.51 (s, 2H), 5.09-5.06 (m, 1H), 4.79-4.73 (m, 1H), 4.65-4.60 (m, 1H), 4.55-4.49 (m, 1H), 4.47-4.42 (m, 3H), 4.38-4.33 (m, 1H), 2.72-2.71 (m, 1H), 2.39-2.38 (m, 1H)

Example 87: Preparation of 2-(4-(6-(4-cyanobenzyloxy)pyridin-2-yl)-2-fluorobenzyl)-1-((tetrahydrofuran-2-yl)methyl)-1H-benzo[d]imidazole-6-carboxylic acid

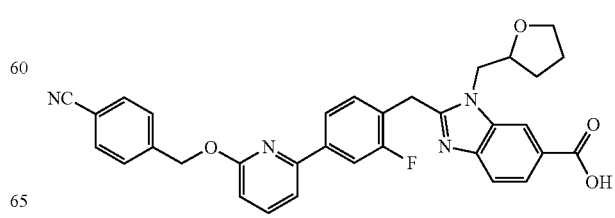

¹H NMR (400 MHz, DMSO) δ 8.39 (s, 1H), 7.94-7.85 (m, 6H), 7.70-7.66 (m, 4H), 7.52-7.48 (m, 1H), 6.96-6.94 (d, 1H), 5.60 (s, 2H), 4.66-4.46 (m, 4H), 4.19-4.15 (m, 1H), 3.82-3.73 (m, 1H), 3.65-3.60 (m, 1H), 2.12-2.06 (m, 1H), 1.92-1.81 (m, 2H), 1.67-1.63 (m, 1H)

Example 88: Preparation of 2-(2-fluoro-4-(6-(4-nitrobenzyloxy)pyridin-2-yl)benzyl)-1-((tetrahydrofuran-2-yl)methyl)-1H-benzo[d]imidazole-6-carboxylic acid

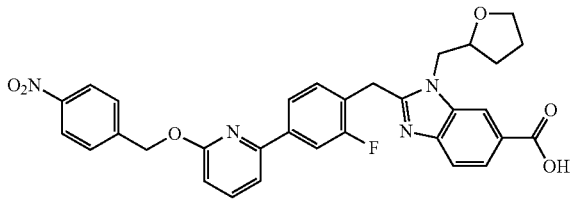 [SMILES: O=C(O)c1ccc2nc(Cc3ccc(-c4cccc(OCc5ccc([N+](=O)[O-])cc5)n4)cc3F)n(CC3CCCO3)c2c1]

¹H NMR (400 MHz, DMSO) δ 8.43 (s, 1H), 8.26-8.24 (d, 2H), 7.98-7.86 (m, 4H), 7.77-7.76 (d, 2H), 7.72-7.67 (m, 2H), 7.54-7.50 (dd, 1H), 6.98-6.96 (d, 1H), 5.65 (s, 2H), 4.65-4.48 (m, 5H), 4.20-4.14 (m, 1H), 3.81-3.77 (m, 2H), 3.69-3.57 (m, 2H), 2.11-2.08 (m, 1H), 1.90-1.80 (m, 2H), 1.66-1.65 (m, 1H)

Example 89: Preparation of 2-(4-(6-(4-bromo-2-fluorobenzyloxy)pyridin-2-yl)-2-fluorobenzyl)-1-((tetrahydrofuran-2-yl)methyl)-1H-benzo[d]imidazole-6-carboxylic acid

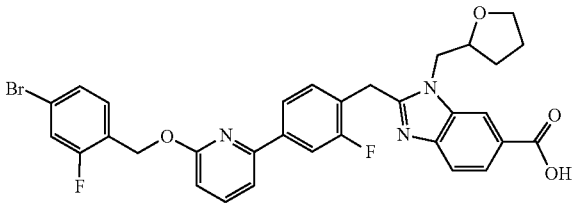 [SMILES: O=C(O)c1ccc2nc(Cc3ccc(-c4cccc(OCc5ccc(Br)cc5F)n4)cc3F)n(CC3CCCO3)c2c1]

¹H NMR (400 MHz, DMSO) δ 8.34 (s, 1H), 7.95-7.83 (m, 4H), 7.68-7.60 (m, 3H), 7.56-7.44 (m, 3H), 6.91-6.89 (d, 1H), 5.51 (s, 2H), 4.66-4.43 (m, 4H), 4.18-4.16 (m, 1H), 3.89-3.79 (m, 2H), 3.65-3.60 (m, 2H), 2.12-2.07 (m, 1H), 1.89-1.81 (m, 2H), 1.67-1.64 (m, 1H)

Example 90: Preparation of 2-(3-fluoro-4-(6-(3-methylbenzyloxy)pyridin-2-yl)benzyl)-1-((tetrahydrofuran-2-yl)methyl)-1H-benzo[d]imidazole-6-carboxylic acid

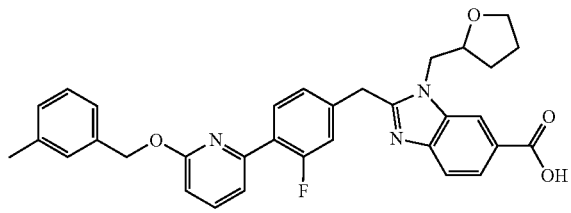 [SMILES: Cc1cccc(COc2cccc(-c3ccc(Cc4nc5ccc(C(=O)O)cc5n4CC4CCCO4)cc3F)n2)c1]

¹H NMR (400 MHz, DMSO) δ 12.75 (br s, 1H), 8.20 (s, 1H), 7.98-7.94 (dd, 1H), 7.84-7.79 (m, 2H), 7.64-7.61 (d, 1H), 7.43-7.25 (m, 5H), 7.14-7.12 (m, 1H), 6.89-6.87 (d, 1H), 5.39 (s, 2H), 4.53-4.52 (m, 1H), 4.49-4.48 (m, 1H), 4.45-4.30 (m, 1H), 4.11-4.09 (m, 1H), 3.79-3.75 (m, 1H), 3.63-3.60 (m, 1H), 2.31 (s, 3H), 2.06-2.0 (m, 1H), 1.85-1.79 (m, 2H), 1.63-1.60 (m, 1H)

Example 91: Preparation of 2-(4-(6-(4-chloro-2-fluorobenzyloxy)-5-fluoropyridin-2-yl)-2-fluorobenzyl)-1-((tetrahydrofuran-2-yl)methyl)-1H-benzo[d]imidazole-6-carboxylic acid

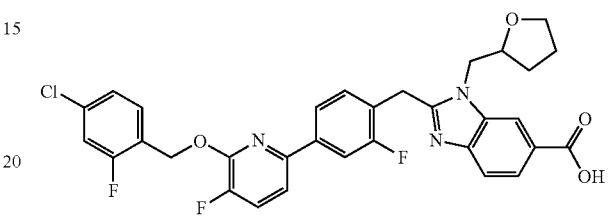

¹H NMR (400 MHz, DMSO) δ 8.21 (s, 1H), 7.90-7.77 (m, 4H), 7.72-7.64 (m, 2H), 7.59-7.56 (d, 1H), 7.53-7.50 (dd, 1H), 7.46-7.42 (dd, 1H), 7.36-7.31 (dd, 1H), 5.62 (s, 2H), 4.56-4.49 (m, 1H), 4.45-4.42 (d, 1H), 4.40-4.33 (m, 1H), 4.17-4.13 (m, 1H), 3.82-3.77 (m, 1H), 3.66-3.61 (m, 1H), 2.12-2.05 (m, 1H), 1.91-1.80 (m, 2H), 1.67-1.62 (m, 1H)

Example 92: Preparation of 2-((3'-(4-chloro-2-fluorobenzyloxy)-2,4'-difluorobiphenyl-4-yl)methyl)-1-((tetrahydrofuran-2-yl)methyl)-1H-benzo[d]imidazole-6-carboxylic acid

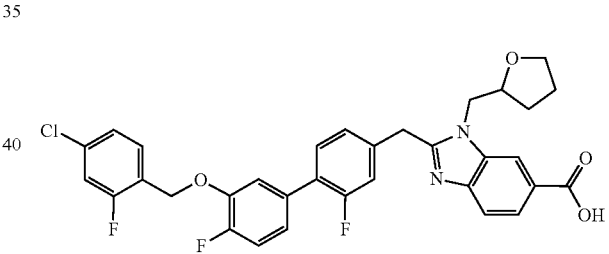

¹H NMR (400 MHz, DMSO) δ 8.52 (s, 1H), 8.21-8.18 (d, 1H), 7.78-7.77 (d, 1H), 7.58-7.52 (m, 2H), 7.34-7.18 (m, 7H), 5.25 (s, 2H), 4.76-4.72 (m, 3H), 4.56-4.50 (m, 1H), 4.29-4.27 (m, 1H), 3.96-3.91 (m, 1H), 3.79-3.76 (m, 1H), 2.26-2.21 (m, 1H), 2.02-1.97 (m, 2H), 1.81-1.74 (m, 1H)

Example 93: Preparation of 2-((3'-(4-cyano-2-fluorobenzyloxy)-2,4'-difluorobiphenyl-4-yl)methyl)-1-((tetrahydrofuran-2-yl)methyl)-1H-benzo[d]imidazole-6-carboxylic acid

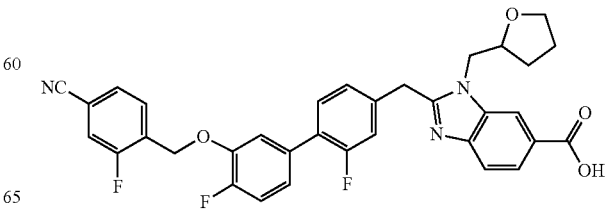

¹H NMR (400 MHz, DMSO) δ 8.52 (s, 1H), 8.20-8.18 (m, 1H), 7.78-7.73 (m, 2H), 7.70-7.68 (m, 2H), 7.56-7.54 (m, 1H), 7.35-7.19 (m, 5H), 5.34 (s, 2H), 4.75-4.70 (m, 3H), 4.56-4.50 (m, 1H), 4.29-4.27 (m, 1H), 3.94-3.90 (m, 1H), 3.79-3.75 (m, 1H), 2.24-2.22 (m, 1H), 2.20-1.96 (m, 2H), 1.79-1.76 (m, 1H)

Example 94: Preparation of 2-(4-(6-(4-chlorobenzyloxy)pyridin-2-yl)-3-fluorobenzyl)-1-((tetrahydrofuran-2-yl)methyl)-1H-benzo[d]imidazole-6-carboxylic acid

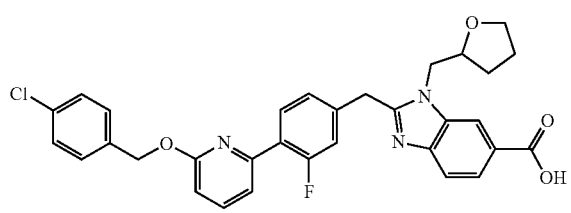 [SMILES: O=C(O)c1ccc2nc(Cc3ccc(-c4cccc(OCc5ccc(Cl)cc5)n4)c(F)c3)n(CC3CCCO3)c2c1]

¹H NMR (400 MHz, DMSO) δ 8.21 (s, 1H), 7.97-7.93 (m, 1H), 7.85-7.79 (m, 2H), 7.64-7.62 (d, 1H), 7.53-7.42 (m, 7H), 7.32-7.26 (m, 3H), 6.91-6.89 (d, 1H), 5.44 (s, 2H), 4.53-4.48 (m, 1H), 4.44 (s, 2H), 4.36-4.30 (m, 1H), 4.11-4.09 (m, 1H), 3.79-3.75 (m, 1H), 3.63-3.59 (m, 1H), 2.08-2.01 (m, 1H), 1.83-1.81 (m, 2H), 1.68-1.55 (m, 1H)

Example 95: Preparation of 2-((3'-(4-chloro-2-fluorobenzyloxy)-3,4'-difluorobiphenyl-4-yl)methyl)-1-((tetrahydrofuran-2-yl)methyl)-1H-benzo[d]imidazole-6-carboxylic acid

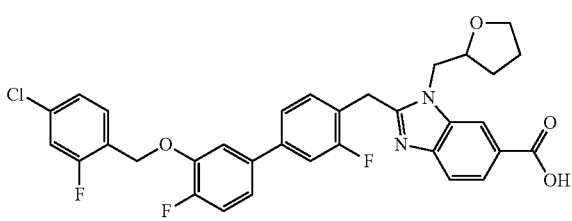 [SMILES: O=C(O)c1ccc2nc(Cc3ccc(-c4ccc(F)c(OCc5ccc(Cl)cc5F)c4)cc3F)n(CC3CCCO3)c2c1]

¹H NMR (400 MHz, DMSO) δ 12.77 (s, 1H), 8.22 (s, 1H), 7.80-7.78 (d, 1H), 7.66-7.58 (m, 4H), 7.44-7.42 (m, 2H), 7.40-7.31 (m, 4H), 5.35 (s, 2H), 4.56-4.33 (m, 4H), 4.16-4.15 (m, 1H), 3.81-3.77 (m, 1H), 3.66-3.63 (m, 1H), 2.09-2.07 (m, 1H), 1.87-1.81 (m, 2H), 1.65-1.62 (m, 1H)

Example 96: Preparation of 2-((3'-(4-cyano-2-fluorobenzyloxy)-3,4'-difluorobiphenyl-4-yl)methyl)-1-((tetrahydrofuran-2-yl)methyl)-1H-benzo[d]imidazole-6-carboxylic acid

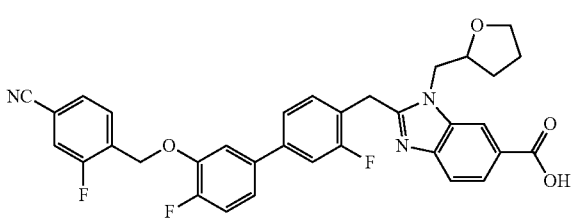 [SMILES: N#Cc1ccc(COc2cc(-c3ccc(Cc4nc5ccc(C(=O)O)cc5n4CC4CCCO4)c(F)c3)ccc2F)c(F)c1]

¹H NMR (400 MHz, DMSO) δ 8.39 (s, 1H), 8.09 (s, 1H), 7.94-7.92 (d, 1H), 7.79-7.64 (m, 6H), 7.59-7.47 (m, 3H), 7.36-7.34 (d, 2H), 5.41 (s, 2H), 4.69-4.46 (m, 4H), 4.18-4.16 (m, 1H), 3.81-3.78 (m, 1H), 3.66-3.60 (m, 1H), 2.11-2.09 (m, 1H), 1.88-1.82 (m, 2H), 1.68-1.65 (m, 1H)

Example 97: Preparation of 2-(3-fluoro-4-(6-(4-(trifluoromethyl)benzyloxy)pyridin-2-yl)benzyl)-1-((tetrahydrofuran-2-yl)methyl)-1H-benzo[d]imidazole-6-carboxylic acid

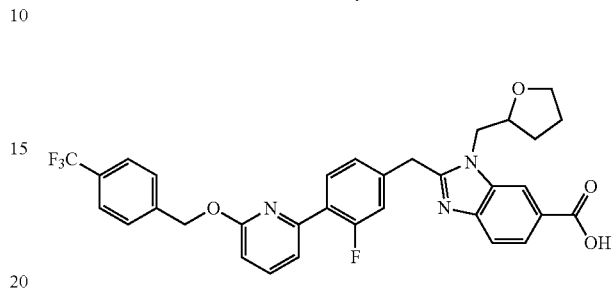

¹H NMR (400 MHz, DMSO) δ 8.21 (s, 1H), 7.93-7.81 (m, 3H), 7.79-7.69 (m, 4H), 7.63-7.61 (d, 1H), 7.46-7.43 (d, 1H), 7.32-7.26 (m, 1H), 6.95-6.93 (d, 1H), 5.55 (s, 2H), 4.53-4.48 (m, 1H), 4.44 (s, 2H), 4.10-4.08 (m, 1H), 3.78-3.74 (m, 1H), 3.62-3.59 (m, 1H), 2.06-2.04 (m, 1H), 1.85-1.79 (m, 2H), 1.62-1.60 (m, 1H)

Example 98: Preparation of 2-(4-(6-(3,4-difluorobenzyloxy)pyridin-2-yl)-3-fluorobenzyl)-1-((tetrahydrofuran-2-yl)methyl)-1H-benzo[d]imidazole-6-carboxylic acid

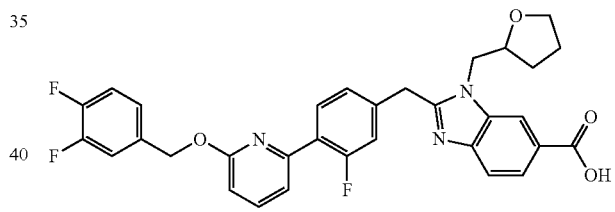

¹H NMR (400 MHz, DMSO) δ 8.21 (s, 1H), 7.98-7.93 (dd, 1H), 7.86-7.79 (m, 2H), 7.64-7.62 (d, 1H), 7.59-7.54 (m, 1H), 7.48-7.41 (m, 2H), 7.36-7.28 (m, 3H), 6.92-6.90 (m, 1H), 5.42 (s, 2H), 4.53-4.49 (m, 1H), 4.45 (s, 2H), 4.36-4.30 (m, 1H), 4.11-4.09 (m, 1H), 3.78-3.75 (m, 1H), 3.63-3.60 (m, 1H), 2.04-1.91 (m, 1), 1.89-1.72 (m, 2H), 1.65-1.55 (m, 1H)

Example 99: Preparation of 2-(4-(6-(4-chloro-3-fluorobenzyloxy)pyridin-2-yl)-3-fluorobenzyl)-1-((tetrahydrofuran-2-yl)methyl)-1H-benzo[d]imidazole-6-carboxylic acid

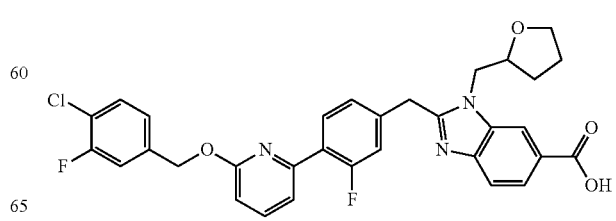

¹H NMR (400 MHz, DMSO) δ 8.25 (s, 1H), 7.94 (t, 1H), 7.87-7.82 (m, 2H), 7.66-7.58 (m, 2H), 7.53 (dd, 1H), 7.44 (dd, 1H), 7.37-7.29 (m, 3H), 6.94-6.92 (d, 1H), 5.45 (s, 2H), 4.57-4.52 (m, 3H), 4.40-4.34 (m, 1H), 4.11-4.10 (m, 1H), 3.80-3.75 (m, 1H), 3.63-3.58 (m, 1H), 2.09-1.99 (m, 1H), 1.96-1.88 (m, 2H), 1.64-1.61 (m, 1H)

Example 100: Preparation of 2-(4-(6-(3-chloro-5-fluorobenzyloxy)pyridin-2-yl)-3-fluorobenzyl)-1-((tetrahydrofuran-2-yl)methyl)-1H-benzo[d]imidazole-6-carboxylic acid

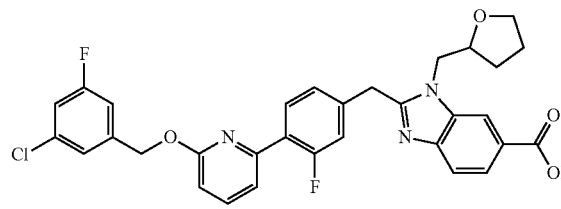

¹H NMR (400 MHz, DMSO) δ 8.40 (s, 1H), 7.98-7.94 (m, 2H), 7.89-7.85 (m, 1H), 7.74-7.72 (d, 1H), 7.47-7.33 (m, 6H), 6.98-6.96 (m, 1H), 5.46 (s, 2H), 4.68-4.61 (m, 3H), 4.61-4.46 (m, 1H), 4.15-4.13 (m, 1H), 3.82-3.78 (m, 2H), 3.64-3.59 (m, 2H), 2.08-2.07 (m, 1H), 1.91-1.80 (m, 2H), 1.68-1.66 (m, 1H)

Example 101: Preparation of 2-(4-(6-(2-chloro-6-fluorobenzyloxy)pyridin-2-yl)-3-fluorobenzyl)-1-((tetrahydrofuran-2-yl)methyl)-1H-benzo[d]imidazole-6-carboxylic acid

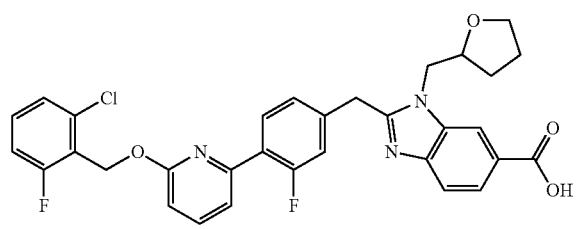 [SMILES: O=C(O)c1ccc2nc(Cc3ccc(-c4cccc(OCc5c(F)cccc5Cl)n4)c(F)c3)n(CC3CCCO3)c2c1]

¹H NMR (400 MHz, DMSO) δ 8.20 (s, 1H), 8.05-8.01 (m, 1H), 7.86-7.80 (m, 2H), 7.63-7.61 (d, 1H), 7.53-7.42 (m, 3H), 7.33-7.30 (m, 3H), 6.87-6.85 (d, 1H), 5.52 (s, 2H), 4.52-4.45 (m, 3H), 4.36-4.30 (m, 1H), 4.11-4.10 (m, 1H), 3.81-3.76 (m, 1H), 3.64-3.58 (m, 1H), 2.09-2.01 (m, 1H), 1.90-1.77 (m, 2H), 1.65-1.61 (m, 1H)

Example 102: Preparation of 2-((5-(3-(4-chloro-2-fluorobenzyloxy)-4-fluorophenyl)pyridin-2-yl)methyl)-1-((tetrahydrofuran-2-yl)methyl)-1H-benzo[d]imidazole-6-carboxylic acid

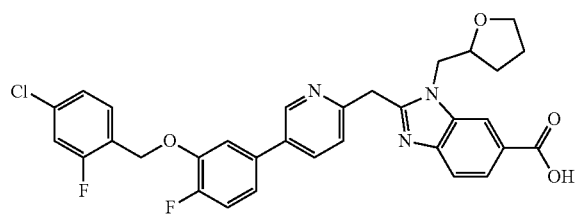 [SMILES: O=C(O)c1ccc2nc(Cc3ccc(-c4ccc(F)c(OCc5ccc(Cl)cc5F)c4)cn3)n(CC3CCCO3)c2c1]

¹H NMR (400 MHz, DMSO) δ 8.84 (s, 1H), 8.25 (s, 1H), 8.12-8.10 (d, 1H), 7.83-7.81 (d, 1H), 7.67-7.61 (m, 3H), 7.53-7.51 (m, 2H), 7.38-7.33 (m, 3H), 5.33 (s, 2H), 4.61-4.57 (m, 3H), 4.46-4.40 (m, 1H), 4.14-4.13 (m, 1H), 3.81-3.76 (m, 1H), 3.64-3.58 (m, 1H), 2.08-2.03 (m, 1H), 1.84-1.79 (m, 2H), 1.63-1.58 (m, 1H)

Example 103: Preparation of (S)-2-(4-(6-(4-cyano-2-fluorobenzyloxy)pyridin-2-yl)-2,6-difluorobenzyl)-1-(oxetan-2-ylmethyl)-1H-benzo[d]imidazole-6-carboxylic acid

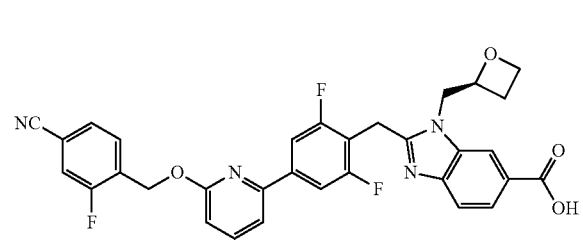 [SMILES: N#Cc1ccc(COc2cccc(-c3cc(F)c(Cc4nc5ccc(C(=O)O)cc5n4C[C@@H]4CCO4)c(F)c3)n2)c(F)c1]

¹H NMR (400 MHz, DMSO) δ 8.27 (s, 1H), 7.97-7.75 (m, 8H), 7.58-7.56 (m, 1H), 7.01-6.69 (m, 1H), 5.66 (s, 2H), 5.15-5.13 (m, 1H), 4.85-4.79 (m, 1H), 4.71-4.67 (m, 1H), 4.60-4.40 (m, 3H), 4.39-4.35 (m, 1H), 2.79-2.75 (m, 1H), 2.46-2.39 (m, 1H)

Examples 104 to 109, 111 and 112 below were prepared in the same manner as in Example 110, except that starting materials according to the structure of the compound to be prepared were used.

Example 104: Preparation of 2-((4-(3-(4-cyano-2-fluorobenzyloxy)phenyl)-2-oxopyridin-1(2H)-yl)methyl)-1-(2-methoxyethyl)-1H-benzo[d]imidazole-6-carboxylic acid

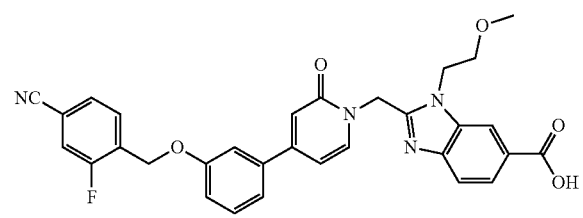 [SMILES: COCCn1c(Cn2ccc(-c3cccc(OCc4ccc(C#N)cc4F)c3)cc2=O)nc2ccc(C(=O)O)cc21]

¹H NMR (400 MHz, DMSO) δ 8.23 (s, 1H), 8.08 (s, 1H), 7.95-7.93 (d, 1H), 7.83-7.56 (m, 5H), 7.46-7.35 (m, 3H), 7.16-7.14 (m, 1H), 6.76-6.71 (m, 2H), 5.47 (s, 2H), 5.36-5.31 (d, 2H), 4.70-4.68 (m, 2H), 3.88-3.69 (m, 2H), 3.24 (s, 3H)

Example 105: Preparation of 2-((4-(6-(4-chloro-2-fluorobenzyloxy)pyridin-2-yl)-2-oxopyridin-1(2H)-yl)methyl)-1-((tetrahydrofuran-2-yl)methyl)-1H-benzo[d]imidazole-6-carboxylic acid

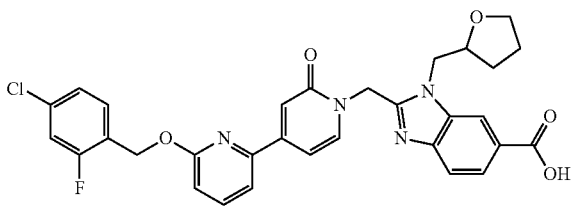 [SMILES: O=C(O)c1ccc2nc(Cn3ccc(-c4cccc(OCc5ccc(Cl)cc5F)n4)cc3=O)n(CC3CCCO3)c2c1]

¹H NMR (400 MHz, DMSO) δ 8.26 (s, 1H), 7.99-7.97 (d, 1H), 7.90-7.86 (dd, 1H), 7.81-7.78 (dd, 1H), 7.71-7.69 (d, 1H), 7.63-7.59 (m, 2H), 7.52-7.49 (dd, 1H), 7.34-7.32 (dd, 1H), 7.12-7.11 (d, 1H), 7.01-6.98 (m, 2H), 5.58-5.40 (m, 4H), 4.68-4.67 (m, 1H), 4.54-4.48 (m, 1H), 4.20-4.19 (m, 1H), 3.86-3.81 (m, 1H), 3.67-3.62 (m, 1H), 2.14-2.06 (m, 1H), 1.88-1.79 (m, 2H), 1.69-1.67 (m, 1H)

Example 106: Preparation of 2-((4-(3-(4-chloro-2-fluorobenzyloxy)phenyl)-2-oxopyridin-1(2H)-yl)methyl)-1-((tetrahydrofuran-2-yl)methyl)-1H-benzo[d]imidazole-6-carboxylic acid

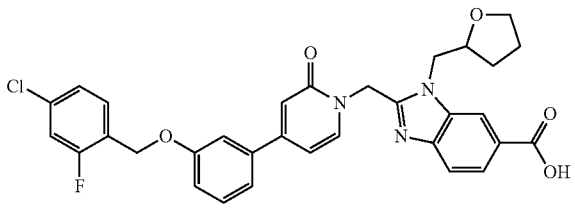 [SMILES: O=C(O)c1ccc2nc(Cn3ccc(-c4cccc(OCc5ccc(Cl)cc5F)c4)cc3=O)n(CC3CCCO3)c2c1]

¹H NMR (400 MHz, DMSO) δ 8.26 (s, 1H), 7.95 (m, 1H), 7.80-7.79 (m, 1H), 7.76 (m, 2H), 7.53-7.50 (m, 1H), 7.44-7.36 (m, 4H), 7.14 (m, 1H), 6.74-6.71 (m, 2H), 5.56-5.39 (m, 2H), 5.24 (s, 2H), 4.68-4.65 (m, 1H), 4.54-4.50 (m, 1H), 4.19 (m, 1H), 3.83-3.81 (m, 1H), 3.64-3.63 (m, 1H), 2.10-2.09 (m, 1H), 1.84 (m, 2H), 1.66-1.64 (m, 1H)

Example 107: Preparation of 2-((4-(3-(4-cyano-2-fluorobenzyloxy)phenyl)-2-oxopyridin-1(2H)-yl)methyl)-1-((tetrahydrofuran-2-yl)methyl)-1H-benzo[d]imidazole-6-carboxylic acid

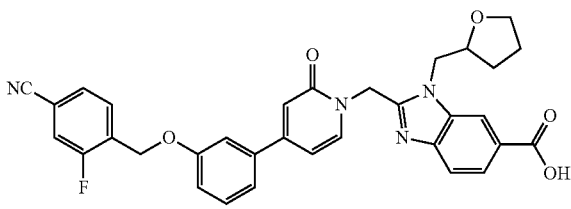 [SMILES: N#Cc1ccc(COc2cccc(-c3ccn(Cc4nc5ccc(C(=O)O)cc5n4CC4CCCO4)c(=O)c3)c2)c(F)c1]

¹H NMR (400 MHz, DMSO) δ 8.26 (dd, 1H), 7.96-7.93 (m, 2H), 7.83-7.65 (m, 3H), 7.63-7.61 (m, 1H), 7.46-7.40 (m, 2H), 7.37-7.34 (m, 1H), 7.17-7.13 (m, 1H), 6.75-6.70 (m, 2H), 5.56-5.52 (d, 1H), 5.43-5.39 (d, 1H), 5.36-5.30 (m, 2H), 4.68-4.64 (m, 1H), 4.54-4.49 (m, 1H), 4.21-4.18 (m, 1H), 3.88-3.80 (m, 1H), 3.67-3.61 (m, 1H), 2.12-2.08 (m, 1H), 1.88-1.80 (m, 2H), 1.69-1.62 (m, 1H)

Example 108: Preparation of (S)-2-((4-(6-(4-chloro-2-fluorobenzyloxy)pyridin-2-yl)-2-oxopyridin-1(2H)-yl)methyl)-1-((tetrahydrofuran-2-yl)methyl)-1H-benzo[d]imidazole-6-carboxylic acid

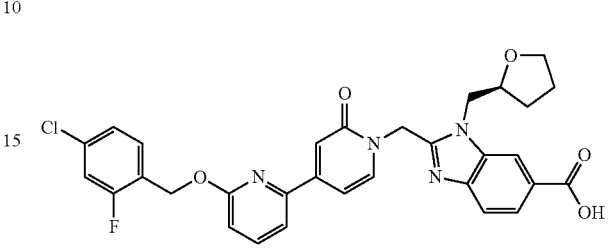

¹H NMR (400 MHz, DMSO) δ 8.26 (s, 1H), 7.98-7.97 (d, 1H), 7.90-7.86 (dd, 1H), 7.81-7.78 (dd, 1H), 7.70-7.69 (d, 1H), 7.63-7.59 (m, 2H), 7.51-7.48 (dd, 1H), 7.34-7.31 (dd, 1H), 7.11 (d, 1H), 7.01-6.98 (m, 2H), 5.58-5.40 (m, 4H), 4.68-4.64 (m, 1H), 4.54-4.48 (m, 1H), 4.22-4.16 (m, 1H), 3.86-3.80 (m, 1H), 3.67-3.61 (m, 1H), 2.14-2.06 (m, 1H), 1.88-1.83 (m, 2H), 1.70-1.60 (m, 1H)

Example 109: Preparation of (S)-2-((4-(6-(4-cyano-2-fluorobenzyloxy)pyridin-2-yl)-2-oxopyridin-1(2H)-yl)methyl)-1-((tetrahydrofuran-2-yl)methyl)-1H-benzo[d]imidazole-6-carboxylic acid

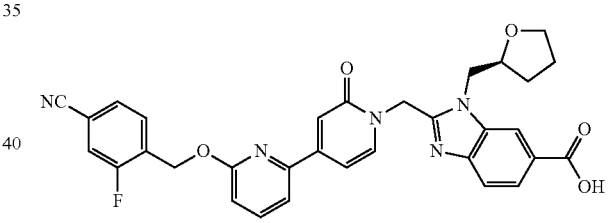

¹H NMR (400 MHz, DMSO) δ 8.26 (s, 1H), 7.98-7.88 (m, 3H), 7.81-7.70 (m, 4H), 7.60 (d, 1H), 7.08 (d, 1H), 7.03 (d, 1H), 6.95 (dd, 1H), 5.60-5.39 (m, 4H), 4.68-4.63 (m, 1H), 4.53-4.48 (m, 1H), 4.22-4.16 (m, 1H), 3.85-3.80 (m, 1H), 3.67-3.61 (m, 1H), 2.12-2.06 (m, 1H), 1.91-1.83 (m, 2H), 1.69-1.58 (m, 1H)

Example 111: Preparation of (S)-2-((4-(6-(4-cyano-2-fluorobenzyloxy)pyridin-2-yl)-2-oxopyridin-1(2H)-yl)methyl)-1-(oxetan-2-ylmethyl)-1H-benzo[d]imidazole-6-carboxylic acid

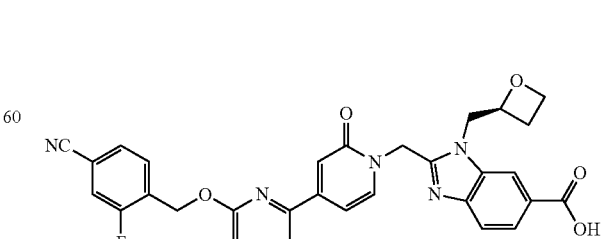

¹H NMR (400 MHz, DMSO) δ 8.28 (s, 1H), 7.98-7.86 (m, 3H), 7.82-7.60 (m, 5H), 7.10-6.95 (m, 3), 5.60-5.43 (m, 4H), 5.12-5.06 (m, 1H), 4.88-4.70 (m, 2H), 4.52-4.47 (m, 1H), 4.38-4.33 (m, 1H), 2.77-2.68 (m, 1H), 2.43-2.39 (m, 1H)

Example 112: Preparation of 2-((4-(6-(4-chloro-2-fluorobenzyloxy)pyridin-2-yl)-6-oxopyrimidin-1(6H)-yl)methyl)-1-((tetrahydrofuran-2-yl)methyl)-1H-benzo[d]imidazole-6-carboxylic acid

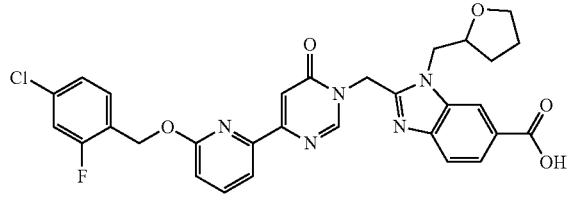 [SMILES: O=C(O)c1ccc2nc(Cn3cnc(-c4cccc(OCc5ccc(Cl)cc5F)n4)cc3=O)n(CC3CCCO3)c2c1]

¹H NMR (400 MHz, DMSO) δ 8.80 (s, 1H), 8.23 (s, 1H), 7.99-7.92 (m, 2H), 7.81-7.79 (d, 1H), 7.63-7.59 (m, 2H), 7.50-7.48 (d, 1H), 7.39-7.29 (m, 2H), 7.06-7.04 (d, 1H), 5.60-5.47 (m, 4H), 4.80-4.76 (m, 1H), 4.68-4.59 (m, 1H), 4.23-4.21 (m, 1H), 3.87-3.82 (m, 1H), 3.68-3.63 (m, 1H), 2.15-2.07 (m, 1H), 1.87-1.80 (m, 2H), 1.69-1.61 (m, 1H)

Examples 113 to 130 and 132 to 135 below were prepared in the same manner as in Example 60, except that starting materials according to the structure of the compound to be prepared were used.

Example 113: Preparation of (S)-2-(4-(6-((4-cyano-2-fluorobenzyl)oxy)pyridin-2-yl)-2,3-difluorobenzyl)-1-(oxetan-2-ylmethyl)-1H-benzo[d]imidazole-6-carboxylic acid

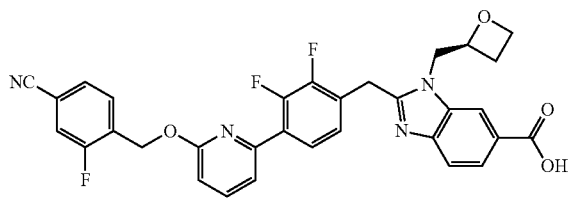 [SMILES: N#Cc1ccc(COc2cccc(-c3ccc(Cc4nc5ccc(C(=O)O)cc5n4C[C@@H]4CCO4)c(F)c3F)n2)c(F)c1]

¹H NMR (400 MHz, DMSO-d₆) δ 8.28 (s, 1H), 7.99-7.94 (m, 2H), 7.83-7.77 (m, 4H), 7.63-7.61 (d, 1H), 7.54-7.52 (dd, 1H), 7.33-7.30 (t, 1H), 7.04-7.02 (d, 1H), 5.61 (s, 2H), 5.12-5.10 (m, 1H), 4.81-4.75 (m, 1H), 4.67-4.60 (m, 2H), 4.53-4.50 (m, 2H), 4.41-4.36 (m, 1H), 2.77-2.73 (m, 1H), 2.44-2.39 (m, 1H)

Example 114: Preparation of 2-(4-(6-((4-cyano-2-fluorobenzyl)oxy)pyridin-2-yl)-3-fluorobenzyl)-1-(oxetan-2-ylmethyl)-1H-benzo[d]imidazole-6-carboxylic acid

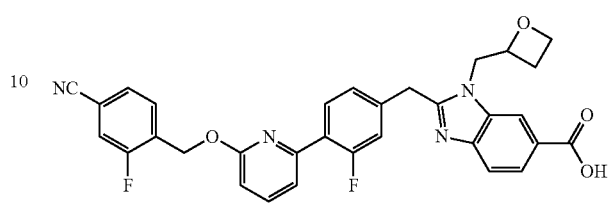

¹H NMR (400 MHz, DMSO-d₆) δ 8.28 (s, 1H), 7.97-7.88 (m, 3H), 7.84-7.83 (m, 1H), 7.79-7.75 (m, 2H), 7.68-7.66 (d, 1H), 7.36-7.32 (m, 2H), 6.99-6.97 (d, 1H), 5.61 (s, 2H), 5.03-5.02 (m, 1H), 4.77-4.71 (m, 1H), 4.63-4.59 (m, 1H), 4.56-4.51 (m, 3H), 4.42-4.37 (m, 1H), 2.73-2.69 (m, 1H), 2.43-2.38 (m, 1H)

Example 115: Preparation of (S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid

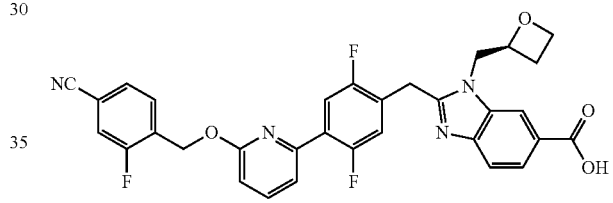

¹H NMR (400 MHz, DMSO-d₆) δ 8.29 (s, 1H), 7.97-7.91 (m, 2H), 7.83-7.75 (m, 4H), 7.64-7.62 (d, 1H), 7.57-7.55 (d, 1H), 7.44-7.39 (m, 1H), 7.03-7.01 (d, 1H), 5.64 (s, 2H), 5.13-5.09 (m, 1H), 4.81-4.76 (m, 1H), 4.68-4.63 (m, 1H), 4.58-4.54 (m, 3H), 4.41-4.36 (m, 1H), 2.77-2.63 (m, 1H), 2.45-2.40 (m, 1H)

Example 116: Preparation of (S)-2-(4-(6-((4-chloro-2-fluorobenzyl)oxy)pyridin-2-yl)-2,5-difluorobenzyl)-1-((tetrahydrofuran-2-yl)methyl)-1H-benzo[d]imidazole-6-carboxylic acid

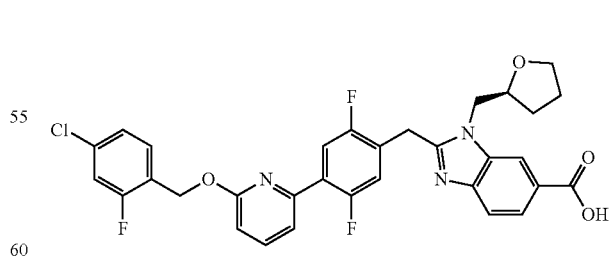

¹H NMR (400 MHz, DMSO-d₆) δ 8.38 (s, 1H), 7.93-7.85 (m, 3H), 7.71-7.69 (d, 1H), 7.65-7.61 (t, 1H), 7.56-7.49 (m, 3H), 7.37-7.35 (dd, 1H), 6.99-6.97 (d, 1H), 5.53 (s, 2H), 4.71-4.64 (m, 1H), 4.60-4.50 (m, 3H), 4.24-4.22 (m, 1H), 3.85-3.80 (q, 1H), 3.69-3.63 (q, 1H), 2.89-2.84 (m, 1H), 2.59-2.54 (m, 2H), 1.71-1.68 (m, 1H)

Example 117: Preparation of (S)-2-(4-(6-((4-chloro-2-fluorobenzyl)oxy)-5-fluoropyridin-2-yl)-3-fluorobenzyl)-1-(oxetan-2-ylmethyl)-1H-benzo[d]imidazole-6-carboxylic acid

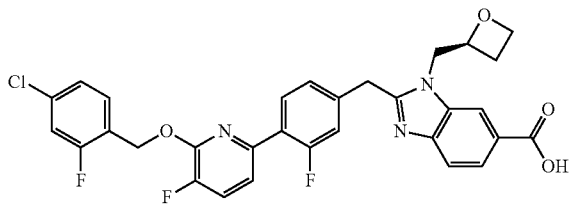 [SMILES: O=C(O)c1ccc2nc(Cc3ccc(-c4ccc(F)c(OCc5ccc(Cl)cc5F)n4)c(F)c3)n(C[C@@H]3CCO3)c2c1]

¹H NMR (400 MHz, DMSO-d₆) δ 8.30 (s, 1H), 7.98-7.94 (t, 1H), 7.86-7.82 (m, 2H), 7.69-7.63 (m, 2H), 7.55-7.48 (m, 2H), 7.38-7.33 (m, 3H), 5.59 (s, 2H), 4.78-4.72 (m, 1H), 4.64-4.49 (m, 4H), 4.42-4.38 (m, 1H), 2.55-2.53 (m, 1H), 2.39-2.35 (m, 1H)

Example 118: Preparation of (S)-2-(4-(6-((4-cyanobenzyl)oxy)pyridin-2-yl)-3-fluorobenzyl)-1-(oxetan-2-ylmethyl)-1H-benzo[d]imidazole-6-carboxylic acid

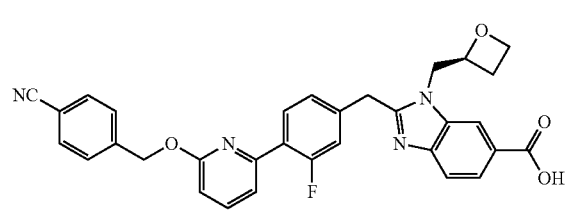 [SMILES: N#Cc1ccc(COc2cccc(-c3ccc(Cc4nc5ccc(C(=O)O)cc5n4C[C@@H]4CCO4)cc3F)n2)cc1]

¹H NMR (400 MHz, DMSO-d₆) δ 8.51 (s, 1H), 8.10-8.02 (m, 6H), 7.90-7.83 (m, 4H), 7.64-7.62 (dd, 1H), 7.54-7.47 (m, 2H), 7.14-7.12 (m, 1H), 5.72 (s, 2H), 5.19-5.17 (m, 1H), 4.98-4.93 (m, 1H), 4.83-4.66 (m, 4H), 4.57-4.55 (m, 1H), 2.88-2.84 (m, 1H), 2.59-2.54 (m, 1H)

Example 119: Preparation of (S)-2-(4-(6-((2,4-difluorobenzyl)oxy)pyridin-2-yl)-3-fluorobenzyl)-1-(oxetan-2-ylmethyl)-1H-benzo[d]imidazole-6-carboxylic acid

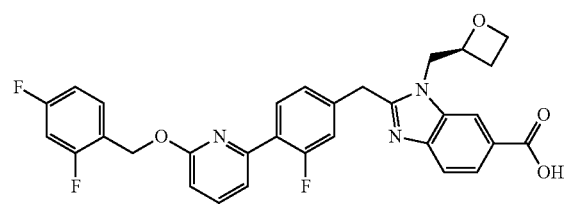 [SMILES: O=C(O)c1ccc2nc(Cc3ccc(-c4cccc(OCc5ccc(F)cc5F)n4)c(F)c3)n(C[C@@H]3CCO3)c2c1]

¹H NMR (400 MHz, DMSO-d₆) δ 8.30 (s, 1H), 8.04-8.00 (t, 1H), 7.88-7.84 (m, 2H), 7.80-7.64 (m, 2H), 7.49-7.47 (dd, 1H), 7.37-7.30 (m, 3H), 7.17-7.12 (m, 1H), 6.92-.6.90 (d, 1H), 5.49 (s, 2H), 5.04-5.01 (m, 1H), 4.78-4.72 (m, 1H), 4.64-4.57 (m, 1H), 4.54-4.48 (m, 3H), 4.41-4.37 (m, 1H), 2.73-2.69 (m, 1H), 2.43-2.38 (m, 1H)

Example 120: Preparation of (S)-2-(4-(6-((4-cyano-2-fluorobenzyl)oxy)pyridin-2-yl)-2,5-difluorobenzyl)-1-((tetrahydrofuran-2-yl)methyl)-1H-benzo[d]imidazole-6-carboxylic acid ¹H NMR (400 MHz, MeOD-d₄) δ 8.63 (s, 1H), 8.29-8.27 (dd, 1H), 7.88-7.76 (m, 3H), 7.76-7.72 (t, 1H), 7.63-7.46 (m, 3H), 7.46-7.41 (m, 1H), 6.99-.6.97 (d, 1H), 5.64 (s, 2H), 4.86-4.79 (m, 2H), 4.69-4.63 (m, 1H), 4.36-4.34 (m, 1H), 3.98-3.93 (q, 1H), 3.81-3.75 (q, 1H), 2.32-2.27 (m, 1H), 2.10-2.00 (m, 2H), 1.84-1.79 (m, 1H)

Example 121: Preparation of (S)-2-(3-fluoro-4-(6-((4-(trifluoromethyl)benzyl)oxy)pyridin-2-yl)benzyl)-1-(oxetan-2-ylmethyl)-1H-benzo[d]imidazole-6-carboxylic acid ¹H NMR (400 MHz, CDCl₃) δ 8.14 (s, 1H), 8.09-8.07 (d, 1H), 7.98-7.94 (t, 1H), 7.90-7.88 (d, 1H), 7.67-7.55 (m, 5H), 7.44-7.42 (d, 1H), 7.20-.7.18 (d, 1H), 7.12-7.09 (d, 1H), 6.79-6.77 (d, 1H), 5.55 (s, 2H), 5.14-5.12 (m, 1H), 4.70-4.60 (m, 3H), 4.44-4.30 (m, 3H), 2.73-2.67 (m, 1H), 2.40-2.36 (m, 1H)

Example 122: Preparation of (S)-2-(3-fluoro-4-(6-((4-methoxybenzyl)oxy)pyridin-2-yl)benzyl)-1-(oxetan-2-ylmethyl)-1H-benzo[d]imidazole-6-carboxylic acid ¹H NMR (400 MHz, DMSO-d₆) δ 8.24 (s, 1H), 8.02-7.98 (t, 1H), 7.88-7.84 (m, 2H), 7.64-7.62 (m, 1H), 7.48-7.46 (d, 1H), 7.35-7.31 (m, 3H), 7.09-7.07 (m, 2H), 6.94-.6.90 (m, 2H), 5.45 (s, 2H), 5.04-5.01 (m, 1H), 4.69-4.38 (m, 6H), 2.71-2.68 (m, 1H), 2.43-2.38 (m, 1H)

Example 123: Preparation of (S)-2-(4-(6-((4-chlorobenzyl)oxy)pyridin-2-yl)-3-fluorobenzyl)-1-(oxetan-2-ylmethyl)-1H-benzo[d]imidazole-6-carboxylic acid

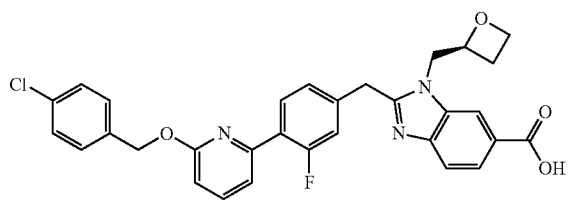 [SMILES: O=C(O)c1ccc2nc(Cc3ccc(-c4cccc(OCc5ccc(Cl)cc5)n4)c(F)c3)n(C[C@@H]3CCO3)c2c1]

¹H NMR (400 MHz, DMSO-d₆) δ 8.43 (s, 1H), 8.15-8.11 (t, 1H), 8.03-7.97 (m, 2H), 7.83-7.81 (d, 1H), 7.70-7.68 (m, 2H), 7.64-7.60 (m, 3H), 7.51-7.46 (m, 2H), 7.09-7.07 (d, 1H), 5.62 (s, 2H), 5.15-5.14 (m, 1H), 4.91-4.86 (m, 1H), 4.77-4.73 (m, 1H), 4.70-4.61 (m, 3H), 4.56-4.51 (m, 1H), 2.87-2.83 (m, 1H), 2.57-2.52 (m, 1H)

Example 124: Preparation of (S)-2-(3-fluoro-4-(6-((4-nitrobenzyl)oxy)pyridin-2-yl)benzyl)-1-(oxetan-2-ylmethyl)-1H-benzo[d]imidazole-6-carboxylic acid

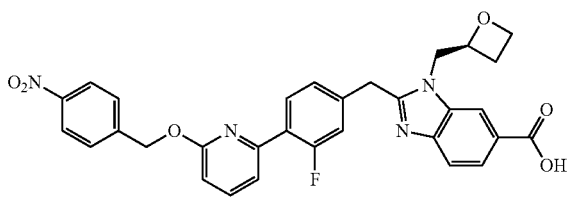 [SMILES: O=C(O)c1ccc2nc(Cc3ccc(-c4cccc(OCc5ccc([N+](=O)[O-])cc5)n4)c(F)c3)n(C[C@@H]3CCO3)c2c1]

¹H NMR (400 MHz, DMSO) δ 8.30-8.27 (m, 3H), 7.96-7.89 (m, 2H), 7.85 (dd, 1H), 7.79-7.77 (d, 2H), 7.68-7.66 (d, 1H), 7.50 (dd, 1H), 7.36-7.30 (m, 2H), 7.01-6.99 (d, 1H), 5.64 (s, 2H), 5.02-5.01 (m, 1H), 4.77-4.71 (m, 1H), 4.59-4.54 (dd, 1H), 4.52-4.46 (m, 3H), 4.42-4.37 (m, 1H), 2.73-2.69 (m, 1H), 2.43-2.39 (m, 1H)

Example 125: Preparation of (S)-2-(4-(6-((3,4-difluorobenzyl)oxy)pyridin-2-yl)-3-fluorobenzyl)-1-(oxetan-2-ylmethyl)-1H-benzo[d]imidazole-6-carboxylic acid

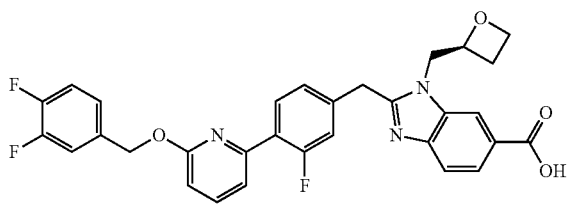 [SMILES: O=C(O)c1ccc2nc(Cc3ccc(-c4cccc(OCc5ccc(F)c(F)c5)n4)c(F)c3)n(C[C@@H]3CCO3)c2c1]

¹H NMR (400 MHz, DMSO) δ 8.07 (s, 1H), 8.03-7.99 (t, 1H), 7.90-7.85 (t, 1H), 7.84-7.83 (dd, 1H), 7.65-7.60 (m, 1H), 7.54-7.49 (m, 2H), 7.48-7.40 (m, 2H), 7.36-7.33 (m, 2H), 6.98-6.95 (d, 1H), 5.48 (s, 2H), 5.07-5.05 (m, 1H), 4.66-4.61 (dd, 1H), 4.55-4.48 (m, 4H), 4.45-4.41 (m, 1H), 2.75-2.70 (m, 1H), 2.47-2.40 (m, 1H)

Example 126: Preparation of (S)-2-(4-(6-((2-chloro-6-fluorobenzyl)oxy)pyridin-2-yl)-3-fluorobenzyl)-1-(oxetan-2-ylmethyl)-1H-benzo[d]imidazole-6-carboxylic acid

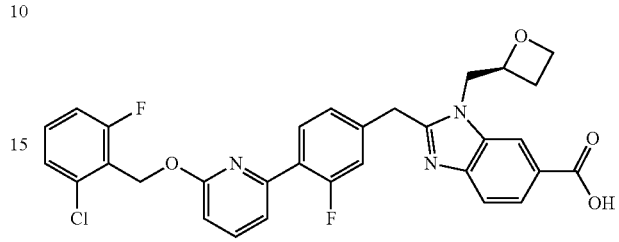

¹H NMR (400 MHz, DMSO) δ 8.13-8.07 (m, 2H), 7.91-7.87 (m, 2H), 7.58-7.47 (m, 4H), 7.40-7.35 (m, 3H), 6.92-6.90 (d, 1H), 5.59 (s, 2H), 5.08-5.06 (m, 1H), 4.66-4.62 (m, 1H), 4.57-4.50 (dd, 4H), 4.45-4.40 (m, 1H), 2.75-2.71 (m, 1H), 2.47-2.42 (m, 1H)

Example 127: Preparation of 2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid

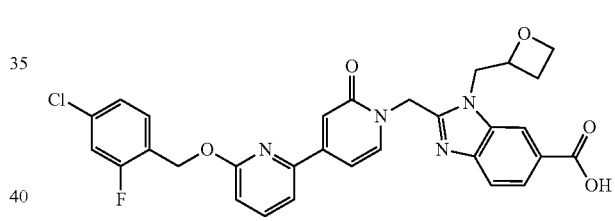

¹H NMR (400 MHz, DMSO) δ 8.35 (s, 1H), 8.05-8.03 (d, 1H), 7.97-7.93 (t, 1H), 7.88-7.85 (dd, 1H), 7.77-7.75 (d, 1H), 7.69-7.65 (m, 2H), 7.58-7.55 (m, 1H), 7.41-7.38 (dd, 1H), 7.18 (s, 1H), 7.08-7.05 (m, 2H), 5.67-5.48 (m, 4H), 5.16-5.14 (m, 1H), 4.91-4.89 (m, 1H), 4.81-4.77 (d, 1H), 4.59-4.54 (m, 1H), 4.44-4.40 (m, 1H), 2.82-2.74 (m, 1H), 2.56-2.46 (m, 1H)

Example 128: Preparation of (S)-2-(3-fluoro-4-(6-(pyridin-4-ylmethoxy)pyridin-2-yl)benzyl)-1-(oxetan-2-ylmethyl)-1H-benzo[d]imidazole-6-carboxylic acid

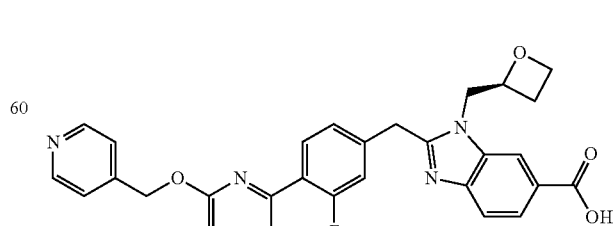

¹H NMR (400 MHz, DMSO) δ 8.78-8.71 (d, 2H), 8.35 (s, 1H), 8.06-8.02 (m, 2H), 7.99-7.97 (d, 1H), 7.76-7.74 (d, 1H), 7.65-7.63 (d, 3H), 7.49-7.43 (m, 2H), 7.16-7.14 (d, 1H), 5.68 (s, 2H), 5.17-5.15 (m, 1H), 4.87-4.81 (dd, 1H), 4.73-4.59 (m, 4H), 4.55-4.51 (m, 1H), 2.86-2.82 (m, 1H), 2.55-2.52 (m, 1H)

Example 129: Preparation of (S)-2-(3-fluoro-4-(6-(pyridin-3-ylmethoxy)pyridin-2-yl)benzyl)-1-(oxetan-2-ylmethyl)-1H-benzo[d]imidazole-6-carboxylic acid

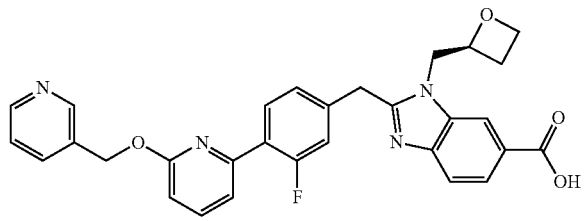 [SMILES: O=C(O)c1ccc2nc(Cc3ccc(-c4cccc(OCc5cccnc5)n4)c(F)c3)n(C[C@@H]3CCO3)c2c1]

¹H NMR (400 MHz, DMSO) δ 8.71 (s, 1H), 8.53-8.52 (d, 1H), 8.06 (s, 1H), 7.98-7.89 (m, 2H), 7.86-7.79 (m, 2H), 7.45-7.40 (m, 3H), 7.31-7.28 (m, 2H), 6.91-6.89 (d, 1H), 5.48 (s, 2H), 5.01-4.99 (m, 1H), 4.61-4.56 (dd, 1H), 4.48-4.39 (m, 4H), 4.37-4.34 (m, 1H), 2.66-2.62 (m, 1H), 2.40-2.34 (m, 1H)

Example 130: Preparation of 2-(4-(6-((4-cyano-2-fluorobenzyl)oxy)pyridin-2-yl)-3-fluorobenzyl)-1-((tetrahydrofuran-2-yl)methyl)-1H-benzo[d]imidazole-6-carboxylic acid

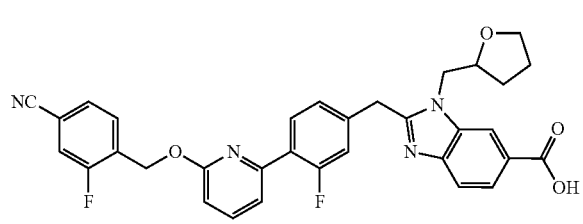 [SMILES: N#Cc1ccc(COc2cccc(-c3ccc(Cc4nc5ccc(C(=O)O)cc5n4CC4CCCO4)cc3F)n2)c(F)c1]

¹H NMR (400 MHz, DMSO) δ 8.21 (s, 1H), 7.93-7.86 (m, 4H), 7.85-7.83 (d, 1H), 7.79-7.71 (m) 1H), 7.69-7.61 (d, 1H), 7.47-7.44 (dd, 1H), 7.32-7.29 (m, 2H), 6.95-6.91 (d, 1H), 5.57 (s, 2H), 4.53-4.44 (m, 3H), 4.36-4.30 (m, 1H), 4.11-4.09 (m, 1H), 3.80-3.74 (q, 1H), 3.63-3.57 (q, 1H), 2.09-2.05 (m, 1H), 1.89-1.84 (m, 2H), 1.82-1.78 (m, 1H)

Example 132: Preparation of (S)-2-(4-(6-(benzo[d]thiazol-2-ylmethoxy)pyridin-2-yl)-3-fluorobenzyl)-1-(oxetan-2-ylmethyl)-1H-benzo[d]imidazole-6-carboxylic acid

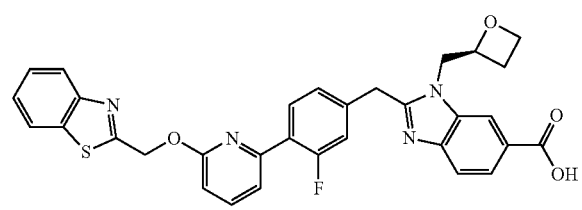 [SMILES: O=C(O)c1ccc2nc(Cc3ccc(-c4cccc(OCc5nc6ccccc6s5)n4)c(F)c3)n(C[C@@H]3CCO3)c2c1]

¹H NMR (400 MHz, DMSO) δ 8.46 (s, 1H), 8.28-8.25 (t, 1H), 8.19-8.13 (m, 3H), 8.08-8.06 (d, 1H), 7.98-7.96 (d, 1H), 7.88-7.87 (m, 1H), 7.78-7.75 (t, 1H), 7.67-7.65 (d, 1H), 7.51-7.47 (t, 1H), 7.41-7.37 (t, 1H), 6.97-6.95 (d, 1H), 5.93 (s, 2H), 5.22-5.19 (m, 1H), 5.01-4.91 (m, 2H), 4.58-4.52 (m, 1H), 4.34-4.28 (m, 1H), 2.79-2.74 (m, 1H), 2.42-2.38 (m, 2H), 2.17-2.02 (m, 1H)

Example 133: Preparation of (S)-2-(4-(6-((4-cyano-2-fluorobenzyl)oxy)pyridin-2-yl)-2-methylbenzyl)-1-(oxetan-2-ylmethyl)-1H-benzo[d]imidazole-6-carboxylic acid

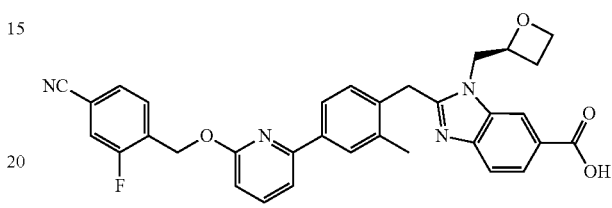

¹H NMR (400 MHz, DMSO) 8.49 (s, 1H), 7.99-7.91 (m, 3H), 7.87-7.82 (m, 2H), 7.78-7.70 (m, 3H), 7.64-7.61 (m, 1H), 7.26-7.24 (d, 1H), 6.93-6.89 (dd, 1H), 5.61 (s, 2H), 5.10-5.08 (m, 1H), 4.76-4.63 (m, 1H), 4.54-4.52 (m, 3H), 4.52-4.50 (m, 1H), 4.43-4.41 (m, 1H), 2.71-2.68 (m, 1H), 2.46-2.43 (m, 1H), 2.32 (s, 3H)

Example 134: Preparation of (S)-2-(4-(6-((4-chloro-2-fluorobenzyl)oxy)pyridin-2-yl)-2-methylbenzyl)-1-(oxetan-2-ylmethyl)-1H-benzo[d]imidazole-6-carboxylic acid

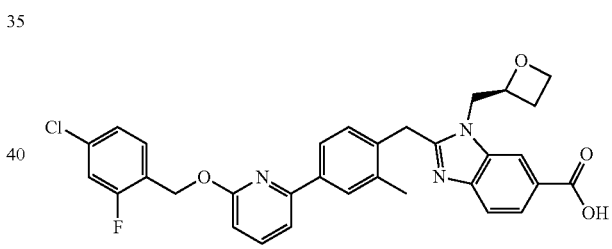

¹H NMR (400 MHz, DMSO) δ 8.22 (s, 1H), 7.91 (s, 1H), 7.84-7.78 (m, 3H), 7.63-7.48 (m, 4H), 7.33-7.31 (dd, 1H), 7.17-7.15 (d, 1H), 6.84-6.82 (d, 1H), 5.51 (s, 2H), 5.03-5.02 (m, 1H), 4.64-4.62 (m, 1H), 4.53-4.35 (m, 5H), 2.68-2.67 (m, 1H), 2.38-2.36 (m, 1H), 2.35 (s, 3H)

Example 135: Preparation of (S)-2-(4-(6-((cyclopropylmethoxy)pyridin-2-yl)-3-fluorobenzyl)-1-(oxetan-2-ylmethyl)-1H-benzo[d]imidazole-6-carboxylic acid

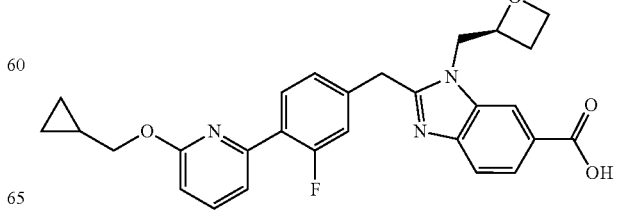

¹H NMR (400 MHz, DMSO) δ 8.30 (s, 1H), 8.21-8.16 (m, 2H), 8.14-8.11 (d, 1H), 8.01-7.98 (dd, 1H), 7.89-7.85 (t, 1H), 7.75-7.72 (d 1H), 7.55-7.53 (dd, 1H), 6.94-6.91 (d, 1H), 5.11-5.08 (m, 1H), 4.97-4.87 (m, 2H), 4.39-4.34 (m, 1H), 4.23-4.18 (d, 2H), 4.14-4.09 (m, 1H), 2.67-2.61 (m, 1H), 2.30-2.24 (m, 1H), 1.34-1.30 (m, 2H), 0.88-0.84 (m, 1H), 0.59-0.56 (m, 2H), 0.39-0.35 (m, 2H)

Experimental Example 1: cAMP Activity Test

The efficacy of the compound according to the present invention as a GLP-1 receptor agonist was determined by measuring cAMP (cyclic Adenosine Monophosphate) activity using a CHO-K1/GLP-1 receptor-expressing cell (Genscript, M00451) that expresses a human GLP-1 receptor.

Specifically, CHO-K1/GLP1 receptor-expressing cells in a Ham's F12 medium containing 10% FBS, 1% NEAA, 200 ug/ml Zeocin, and 100 ug/ml Hygromycin B were dispensed into a 96-well plate (SPL, 30096) at the amount of 30,000 cells/100 uL/well, and incubated in a 37° C., 5% $CO_2$ incubator. The next day, the medium was removed, and a 50 uL of HBSS medium containing 0.1% BSA, 0.5 mM IBMX, and 5 mM HEPES was added to each well. After dissolving a test substance (6.4 nM to 20 uM) of 2× concentration in the HBSS medium containing 0.1% BSA, 0.5 mM IBMX, and 5 mM HEPES, 50 uL of the HBSS medium in which the test substance was dissolved was added to each well, and incubated in a 37° C., 5% $CO_2$ incubator. The cAMP activity was measured according to the manufacturer's instructions using the cAMP dynamic HTRF kit (Cisbio, 62AM4PEC). After incubation, the medium was discarded, and the cells were lysed. cAMP-d2 and anti-cAMP cryptate conjugate were added thereto and reacted for 3 hours. After completion of the reaction, fluorescence was measured with a microplate reader (Molecular Device, Flexstation 3) (excitation wavelength of 313 nm, and emission wavelength of 665 nm and 620 nm). The cAMP activity was shown by fluorescence resonance energy transfer (FRET) which occurs when cAMP-d2 and anti-cAMP-cryptate were in close proximity to each other, and was calculated as a fluorescence ratio of 665 nm/620 nm. Intracellular cAMP competes with cAMP-d2 for anti-cAMP cryptate, and the measured signal of fluorescence resonance energy transfer (FRET) is inversely proportional to intracellular cAMP. The activity of the compounds was calculated based on the degree of change in the FRET signal, and the $EC_{50}$ of the compounds is shown in Table 1 below.

TABLE 1

| Ex. No. | $EC_{50}$ |
|---|---|
| 1 | 10 nM |
| 2 | 63 nM |
| 3 | 32 nM |
| 4 | 200 nM |
| 5 | 620 nM |
| 6 | 25 nM |
| 7 | 2000 nM |
| 8 | 120 nM |
| 9 | 75 nM |
| 10 | 24 nM |
| 11 | 6.5 nM |
| 12 | 85 nM |
| 13 | 35 nM |
| 14 | 93 nM |
| 15 | 16 nM |
| 16 | 82 nM |
| 17 | 8.2 nM |
| 18 | 110 nM |

TABLE 1-continued

| Ex. No. | $EC_{50}$ |
|---|---|
| 19 | 40 nM |
| 20 | 240 nM |
| 21 | 420 nM |
| 22 | 130 nM |
| 23 | 610 nM |
| 24 | 130 nM |
| 25 | 43 nM |
| 26 | 270 nM |
| 27 | 270 nM |
| 28 | 130 nM |
| 29 | 900 nM |
| 30 | 460 nM |
| 31 | 3200 nM |
| 32 | 32 nM |
| 33 | 60 nM |
| 34 | 9.2 nM |
| 35 | 9.0 nM |
| 36 | 88 nM |
| 37 | 13 nM |
| 38 | 140 nM |
| 39 | 250 nM |
| 40 | 260 nM |
| 41 | 110 nM |
| 42 | 250 nM |
| 43 | 72 nM |
| 44 | 230 nM |
| 45 | 3700 nM |
| 46 | 260 nM |
| 47 | 1300 nM |
| 48 | 42 nM |
| 49 | 14 nM |
| 50 | 15 nM |
| 51 | 52 nM |
| 52 | 110 nM |
| 53 | 39 nM |
| 54 | 110 nM |
| 55 | 210 nM |
| 56 | 800 nM |
| 57 | 850 nM |
| 58 | 170 nM |
| 59 | 5.8 nM |
| 60 | <3.2 nM |
| 61 | 8.7 nM |
| 62 | 37 nM |
| 63 | 160 nM |
| 64 | 110 nM |
| 65 | 5 nM |
| 66 | 4.6 nM |
| 67 | 11 nM |
| 68 | 29 nM |
| 69 | 31 nM |
| 70 | <3.2 nM |
| 71 | <3.2 nM |
| 72 | <3.2 nM |
| 73 | 5.2 nM |
| 74 | 5.8 nM |
| 75 | 23 nM |
| 76 | 38 nM |
| 77 | 28 nM |
| 78 | <3.2 nM |
| 79 | <3.2 nM |
| 80 | 190 nM |
| 81 | 210 nM |
| 82 | 4 nM |
| 83 | 160 nM |
| 84 | 4 nM |
| 85 | 74 nM |
| 86 | <3.2 nM |
| 87 | 18 nM |
| 88 | 16 nM |
| 89 | 11 nM |
| 90 | 250 nM |
| 91 | 7.2 nM |
| 92 | 78 nM |
| 93 | 1100 nM |
| 94 | 1.3 nM |
| 95 | 100 nM |
| 96 | 830 nM |

TABLE 1-continued

| Ex. No. | EC$_{50}$ |
|---|---|
| 97 | 31 nM |
| 98 | 61 nM |
| 99 | 70 nM |
| 100 | 320 nM |
| 101 | 320 nM |
| 102 | 460 nM |
| 103 | <3.2 nM |
| 104 | 240 nM |
| 105 | 46 nM |
| 106 | 110 nM |
| 107 | 380 nM |
| 108 | 130 nM |
| 109 | 130 nM |
| 110 | 16 nM |
| 111 | 20 nM |
| 112 | 290 nM |
| 113 | <3.2 nM |
| 114 | <3.2 nM |
| 115 | <3.2 nM |
| 116 | <3.2 nM |
| 117 | <3.2 nM |
| 118 | 4.3 nM |
| 119 | 12 nM |
| 120 | <3.2 nM |
| 121 | 15 nM |
| 122 | 9.5 nM |
| 123 | 14 nM |
| 124 | 4.3 nM |
| 125 | 37 nM |
| 126 | 510 nM |
| 127 | 20 nM |
| 128 | 260 nM |
| 129 | 490 nM |
| 130 | 21 nM |
| 131 | 1600 nM |
| 132 | 460 nM |
| 133 | 14 nM |
| 134 | 190 nM |

Experimental Example 2: hERG Inhibition Test

To measure the hERG (Human ether-a-go-go-related gene) channel inhibition rate of the compound according to the present invention, the following test was performed using a Predictor hERG Fluorescence Polarization assay kit (Invitrogen, PV5365).

Specifically, a test substance was dissolved in DMSO to prepare a 50 mM solution. A 4 mM solution was prepared by diluting the 50 mM solution with DMSO in a U bottom 96-well plate (SPL, 34096), and was then diluted 100-fold with a test buffer to prepare a 40 uM (4x) solution. The positive control E-4031 (3 mM) provided in the kit was diluted 25-fold with a test buffer to prepare a 120 uM solution) 5 uL of the diluted test substance solution was dispensed into a 384-well assay plate (corning, 3677). hERG Membrane (2x) and Tracer (4x) provided in the kit were respectively added at 10 uL and 5 uL, and then subjected to the reaction at room temperature for 2.5 hours. After completion of the reaction, fluorescence polarization (mP) was measured with a Multimode Plate Reader (Perkin-Elmer, Envision) (excitation wavelength of 531 nm, and emission wavelength 579 nm). The value of the percent inhibitory activity (% inhibition) at 10 uM of each test substance was calculated by the following equation, and the results are shown in Table 2:

(% inhibition)=100−{(mP of the compound according to the present invention−E-4031 mP)/(mP of the solvent control−E-4031 mP)}×100

TABLE 2

| Ex. No. | % inh. |
|---|---|
| 1 | 1.26 |
| 2 | −11.87 |
| 3 | 8.39 |
| 4 | −2.87 |
| 5 | 2.74 |
| 6 | 22.84 |
| 7 | 1.63 |
| 8 | 4.01 |
| 9 | 0.48 |
| 10 | −7.54 |
| 11 | −1.31 |
| 12 | −2.74 |
| 13 | −7.76 |
| 14 | −6.08 |
| 15 | 1.67 |
| 16 | −0.94 |
| 17 | −9.12 |
| 18 | 7.37 |
| 19 | 1.8 |
| 20 | 6.19 |
| 21 | −9.94 |
| 22 | −15.46 |
| 23 | −6.89 |
| 24 | −7.68 |
| 25 | 18.92 |
| 26 | 2.43 |
| 27 | −4.76 |
| 28 | 0.52 |
| 29 | −0.75 |
| 30 | 0.33 |
| 31 | −10.42 |
| 32 | −11.67 |
| 33 | −9.08 |
| 34 | −12.59 |
| 35 | −3.82 |
| 36 | −10.78 |
| 37 | −10.57 |
| 38 | 9.50 |
| 39 | −12.78 |
| 40 | 6.91 |
| 41 | −16.01 |
| 42 | −23.58 |
| 43 | −2.26 |
| 44 | 1.77 |
| 45 | 27.74 |
| 46 | 1.04 |
| 47 | −17.13 |
| 48 | 14.30 |
| 49 | 12.51 |
| 50 | 4.72 |
| 51 | −4.69 |
| 52 | 24.18 |
| 53 | 18.70 |
| 54 | 36.49 |
| 55 | 35.40 |
| 56 | 0.83 |
| 57 | 6.42 |
| 58 | 2.81 |
| 59 | −21.00 |
| 60 | −5.42 |
| 61 | −6.72 |
| 62 | −7.49 |
| 63 | −19.65 |
| 64 | −9.05 |
| 65 | 10.75 |
| 66 | −7.97 |
| 67 | 0.85 |
| 68 | −11.36 |
| 69 | −14.66 |
| 70 | −6.14 |
| 71 | −2.52 |
| 72 | −5.75 |
| 73 | −14.60 |
| 74 | −16.20 |
| 75 | −7.98 |
| 76 | −0.50 |
| 77 | −70.88 |
| 78 | −17.92 |

TABLE 2-continued

| Ex. No. | % inh. |
|---|---|
| 79 | -2.04 |
| 80 | -25.22 |
| 81 | -43.55 |
| 82 | 7.24 |
| 83 | 2.37 |
| 84 | -1.15 |
| 85 | -12.95 |
| 86 | 8.93 |
| 87 | 32.89 |
| 88 | 22.15 |
| 89 | 22.15 |
| 90 | 20.22 |
| 91 | -68.23 |
| 92 | 8.68 |
| 93 | 8.90 |
| 94 | 18.94 |
| 95 | -38.2 |
| 96 | 5.19 |
| 97 | 6.11 |
| 98 | -2.76 |
| 99 | -0.33 |
| 100 | -10.18 |
| 101 | -2.37 |
| 102 | -31.91 |
| 103 | 5.66 |
| 104 | 8.69 |
| 105 | 25.09 |
| 106 | -2.71 |
| 107 | 2.70 |
| 108 | 4 |
| 109 | 6.49 |
| 110 | 7.61 |
| 111 | 1.32 |
| 112 | 1.14 |
| 113 | -4.94 |
| 114 | -4.71 |
| 115 | -2.45 |
| 116 | 5.86 |
| 117 | 12.52 |
| 118 | 20.7 |
| 119 | 4.13 |
| 120 | -3.82 |
| 121 | -10.71 |
| 122 | -5.75 |
| 123 | -0.45 |
| 124 | 7.28 |
| 125 | -19.50 |
| 126 | -3.99 |
| 127 | 2.3 |
| 128 | -6.10 |
| 129 | -6.27 |
| 130 | -6.76 |
| 131 | -0.97 |
| 132 | -7.11 |
| 133 | 40.98 |
| 134 | 28.27 |
| 135 | -14.02 |

Experimental Example 3: CYP Inhibition Test

CYP inhibition was tested to confirm the effects of the compounds according to the present invention on liver metabolic enzymes. Corning (459500, 459400, 459100) kits were used for CYP1A2, CYP2C19, and CYP3A4, and Invitrogen (P2861, P2862) kits were used for CYP2C9 and CYP2D6, and the test method basically followed the test methods of each manufacturer.

The test compound was initially prepared by diluting the compound in DMSO (Sigma, 276855) to have a concentration of 50 mM. For Corning products, the test compound (50 mM) was diluted in acetonitrile to have a concentration of 50× of a final concentration (10 uM), and a NADPH-coenzyme mixture and an enzyme-substrate mixture were mixed at a predetermined concentration provided by the kit, according to the type of enzyme) 4 uL of the 50× test compound and 96 uL of the NADPH-coenzyme mixture were mixed in the U-bottom 96-well plate, and then reacted first in a 37° C. incubator for 10 minutes. Next, 100 uL of an enzyme-substrate mixture was added, and reacted in a 37° C. incubator for 15 minutes (CYP1A2) or 30 minutes (CYP2C19, CYP3A4), respectively. At the end of the reaction time, 75 uL of a reaction termination solution (0.5 M Tris base ((HOCH$_2$)$_3$CNH$_2$)) was added to terminate the reaction, the reaction product was transferred to a white plate, and the fluorescence wavelength was read by a microplate reader (Molecular Device, Flexstation 3)(for CYP1A2 and CYP2C19, excitation wavelength 410 nm, emission wavelength of 460 nm; for CYP3A4, excitation wavelength of 409 nm, emission wavelength of 530 nm).

For Invitrogen products, the test compound (50 mM) was diluted in a test buffer to have a concentration of 2.5× of a final concentration (10 uM). The enzyme mixture and the substrate mixture were mixed at a predetermined concentration provided by the kit, according to the type of enzyme) 80 uL of the 2.5× test compound prepared in the U-bottom 96-well plate and 100 uL of the enzyme mixture were mixed, reacted first for 10 minutes. Then, 20 uL of the substrate mixture was added thereto and reacted for 1 hour. After completion of the reaction, the reaction product was transferred to a white plate and the fluorescence wavelength was read by a microplate reader (Molecular Device, Flexstation 3) (for CYP2C9, excitation wavelength of 415 nm, emission wavelength of 460 nm; for CYP2D6, excitation wavelength of 415 nm, emission wavelength of 520 nm). The inhibition rate was calculated as the remaining activity value of the test compound-treated group compared to the solvent control group, using the fluorescence value of the solvent control group as a 100% activity value, as shown in the following equation:

Result value (Remaining Activity; unit %)=(fluorescence value of the test compound/fluorescence value of the solvent control)×100

The results are shown in Tables 3 to 7 below. Each of result values is expressed in % in Tables 3 to 7 below.

TABLE 3

| | CYP inhibition (remaining activity % at 10 uM) | | | | |
|---|---|---|---|---|---|
| Ex. No. | CYP1A2 | CYP2C9 | CYP2C19 | CYP2D6 | CYP3A4 |
| 1 | 72.42 | 10.88 | 53.97 | 12.29 | 62.40 |
| 2 | 75.01 | 30.51 | 46.46 | 60.87 | 96.54 |
| 3 | 104.23 | 25.74 | 58.66 | 78.91 | 83.23 |
| 4 | 107.72 | 28.14 | 59.04 | 74.19 | 66.27 |
| 5 | 95.21 | 16.98 | 49.07 | 78.45 | 82.47 |
| 6 | 102.54 | 29.26 | 60.8 | 72.46 | 76.93 |
| 7 | 94.28 | 7.15 | 62.55 | 77.27 | 83.82 |
| 8 | 105.99 | 48.39 | 75.52 | 94.77 | 104.45 |
| 9 | 107.70 | 37.16 | 70.75 | 93.00 | 104.89 |
| 10 | 105.32 | 55.40 | 52.55 | 86.39 | 92.13 |
| 11 | 101.16 | 61.97 | 58.37 | 94.32 | 81.52 |
| 12 | 102.57 | 36.48 | 35.61 | 83.91 | 84.44 |
| 13 | 106.72 | 49.26 | 62.62 | 97.94 | 97.88 |
| 14 | 103.89 | 28.15 | 54.49 | 83.25 | 87.21 |
| 15 | 105.28 | 41.28 | 36.52 | 76.82 | 96.44 |
| 16 | 109.5 | 35.13 | 45.55 | 80.09 | 88.33 |
| 17 | 109.79 | 40.31 | 73.44 | 87.81 | 93.13 |
| 18 | 104.17 | 19.64 | 34.78 | 62.81 | 92.13 |
| 19 | 104.64 | 14.25 | 29.17 | 81.66 | 80.58 |
| 20 | 101.53 | 46.10 | 74.33 | 78.28 | 101.89 |
| 21 | 102.14 | 22.84 | 61.28 | 75.30 | 97.30 |
| 22 | 111.06 | 18.00 | 60.44 | 81.32 | 92.78 |
| 23 | 100.73 | 8.13 | 76.83 | 79.54 | 25.44 |

TABLE 3-continued

| Ex. No. | CYP1A2 | CYP2C9 | CYP2C19 | CYP2D6 | CYP3A4 |
|---|---|---|---|---|---|
| 24 | 108.14 | 24.87 | 48.29 | 84.82 | 83.28 |
| 25 | 96.30 | 29.48 | 55.28 | 81.07 | 97.39 |
| 26 | 99.13 | 29.40 | 52.97 | 85.41 | 90.46 |
| 27 | 97.52 | 14.46 | 28.57 | 75.91 | 90.59 |
| 28 | 104.28 | 11.67 | 30.76 | 85.48 | 87.88 |
| 29 | 89.78 | 16.80 | 19.57 | 65.89 | 82.23 |
| 30 | 95.68 | 20.98 | 20.30 | 52.02 | 77.06 |

CYP inhibition (remaining activity % at 10 uM)

TABLE 4

| Ex. No. | CYP1A2 | CYP2C9 | CYP2C19 | CYP2D6 | CYP3A4 |
|---|---|---|---|---|---|
| 31 | 99.80 | 12.37 | 84.45 | 93.84 | 110.98 |
| 32 | 75.90 | 19.82 | 27.84 | 67.67 | 81.70 |
| 33 | 89.21 | 16.02 | 27.81 | 69.76 | 81.27 |
| 34 | 98.60 | 23.52 | 29.56 | 66.89 | 73.69 |
| 35 | 84.53 | 42.43 | 27.88 | 60.39 | 54.98 |
| 36 | 110.17 | 31.58 | 35.70 | 84.11 | 83.81 |
| 37 | 107.89 | 41.87 | 46.15 | 93.81 | 88.84 |
| 38 | 99.95 | 32.85 | 49.46 | 72.59 | 83.26 |
| 39 | 100.04 | 11.46 | 52.62 | 80.38 | 88.18 |
| 40 | 100.49 | 13.68 | 39.58 | 78.41 | 81.97 |
| 41 | 108.66 | 20.65 | 56.87 | 86.19 | 88.63 |
| 42 | 100.63 | 15.41 | 79.56 | 87.69 | 81.10 |
| 43 | 113.83 | 41.65 | 59.87 | 93.26 | 94.27 |
| 44 | 107.09 | 31.83 | 56.38 | 89.39 | 96.58 |
| 45 | 116.83 | 21.27 | 53.82 | 89.80 | 92.57 |
| 46 | 102.71 | 34.82 | 82.12 | 94.63 | 103.01 |
| 47 | 98.58 | 44.86 | 80.18 | 95.76 | 97.02 |
| 48 | 108.66 | 15.50 | 60.40 | 86.03 | 98.42 |
| 49 | 107.66 | 21.01 | 58.63 | 88.40 | 109.84 |
| 50 | 107.23 | 6.48 | 27.21 | 89.21 | 81.83 |
| 51 | 113.83 | 36.88 | 33.58 | 91.73 | 108.89 |
| 52 | 102.91 | 27.27 | 46.03 | 90.78 | 93.00 |
| 53 | 99.56 | 25.60 | 26.22 | 95.67 | 91.55 |
| 54 | 98.22 | 40.13 | 46.62 | 91.34 | 103.28 |
| 55 | 104.22 | 25.10 | 23.02 | 80.99 | 87.83 |
| 56 | 99.67 | 23.52 | 47.41 | 93.77 | 101.04 |
| 57 | 106.38 | 21.96 | 42.25 | 82.10 | 102.71 |
| 58 | 104.57 | 34.44 | 60.45 | 93.23 | 86.12 |
| 59 | 112.32 | 52.35 | 77.42 | 100.67 | 92.02 |
| 60 | 115.05 | 54.10 | 75.28 | 99.50 | 86.43 |

TABLE 5

| Ex. No. | CYP1A2 | CYP2C9 | CYP2C19 | CYP2D6 | CYP3A4 |
|---|---|---|---|---|---|
| 61 | 112.00 | 28.79 | 51.87 | 96.84 | 78.96 |
| 62 | 100.27 | 38.89 | 47.82 | 91.61 | 91.92 |
| 63 | 110.74 | 81.33 | 77.69 | 98.65 | 100.06 |
| 64 | 109.09 | 48.48 | 65.16 | 81.39 | 95.70 |
| 65 | 75.99 | 42.76 | 53.28 | 93.74 | 90.75 |
| 66 | 102.99 | 57.88 | 61.59 | 94.24 | 90.23 |
| 67 | 99.54 | 63.02 | 90.18 | 96.78 | 94.17 |
| 68 | 100.92 | 52.81 | 62.76 | 89.37 | 82.38 |
| 69 | 104.00 | 53.70 | 61.32 | 89.90 | 80.80 |
| 70 | 107.36 | 45.49 | 73.46 | 97.43 | 96.67 |
| 71 | 96.64 | 34.49 | 45.33 | 88.89 | 71.74 |
| 72 | 50.20 | 34.67 | 56.83 | 71.56 | 27.86 |
| 73 | 106.72 | 49.69 | 69.27 | 87.73 | 90.80 |
| 74 | 107.90 | 58.99 | 79.08 | 86.75 | 86.98 |
| 75 | 103.30 | 12.38 | 52.88 | 94.51 | 78.59 |
| 76 | 108.67 | 19.35 | 68.62 | 95.83 | 37.74 |
| 77 | 109.20 | 18.72 | 63.28 | 91.81 | 84.80 |
| 78 | 117.26 | 48.21 | 71.58 | 96.25 | 82.34 |
| 79 | 105.36 | 37.69 | 41.66 | 90.54 | 70.86 |
| 80 | 106.74 | 17.63 | 90.89 | 92.34 | 53.96 |

TABLE 5-continued

| Ex. No. | CYP1A2 | CYP2C9 | CYP2C19 | CYP2D6 | CYP3A4 |
|---|---|---|---|---|---|
| 81 | 104.21 | 15.55 | 61.94 | 90.05 | 46.78 |
| 82 | 110.56 | 28.71 | 35.13 | 92.76 | 79.17 |
| 83 | 110.37 | 33.09 | 73.98 | 96.93 | 94.71 |
| 84 | 114.31 | 30.24 | 57.59 | 93.81 | 86.43 |
| 85 | 116.00 | 25.59 | 61.49 | 93.81 | 85.00 |
| 86 | 108.19 | 44.74 | 66.61 | 93.73 | 86.62 |
| 87 | 99.15 | 21.03 | 44.90 | 83.26 | 92.80 |
| 88 | 100.93 | 23.07 | 47.62 | 88.91 | 78.63 |
| 89 | 103.62 | 36.39 | 76.22 | 95.81 | 99.30 |
| 90 | 107.93 | 20.48 | 64.96 | 90.91 | 10.52 |

TABLE 6

| Ex. No. | CYP1A2 | CYP2C9 | CYP2C19 | CYP2D6 | CYP3A4 |
|---|---|---|---|---|---|
| 91 | 71.41 | 54.70 | 84.89 | 91.07 | 82.39 |
| 92 | 89.26 | 23.19 | 59.43 | 90.93 | 84.39 |
| 93 | 99.48 | 12.77 | 64.82 | 91.30 | 96.89 |
| 94 | 107.24 | 21.50 | 52.42 | 83.59 | 74.71 |
| 95 | 109.31 | 15.52 | 54.19 | 86.41 | 89.42 |
| 96 | 99.04 | 22.28 | 76.26 | 90.36 | 83.45 |
| 97 | 111.22 | 16.35 | 49.74 | 87.71 | 76.63 |
| 98 | 114.47 | 24.09 | 65.18 | 92.76 | 66.06 |
| 99 | 107.41 | 18.08 | 47.66 | 85.68 | 79.18 |
| 100 | 106.59 | 15.97 | 58.10 | 91.44 | 81.71 |
| 101 | 102.61 | 41.54 | 73.00 | 95.03 | 86.69 |
| 102 | 99.57 | 12.65 | 88.31 | 84.79 | 118.35 |
| 103 | 103.43 | 40.32 | 51.41 | 45.09 | 116.74 |
| 104 | 106.22 | 82.68 | 97.64 | 97.88 | 96.36 |
| 105 | 106.13 | 61.41 | 67.79 | 85.24 | 74.17 |
| 106 | 107.66 | 42.47 | 77.82 | 94.73 | 98.23 |
| 107 | 103.40 | 64.36 | 85.47 | 94.78 | 97.57 |
| 108 | 105.60 | 59.37 | 92.18 | 93.78 | 92.37 |
| 109 | 96.16 | 79.16 | 83.89 | 96.36 | 91.87 |
| 110 | 100.22 | 71.78 | 95.40 | 95.40 | 92.46 |
| 111 | 102.11 | 73.86 | 91.41 | 95.85 | 94.96 |
| 112 | 106.11 | 60.48 | 77.49 | 95.56 | 93.18 |
| 113 | 101.14 | 26.35 | 25.15 | 81.08 | 95.67 |
| 114 | 100.27 | 53.91 | 81.85 | 90.37 | 89.71 |
| 115 | 104.22 | 34.42 | 57.13 | 94.05 | 89.89 |
| 116 | 104.18 | 39.93 | 70.86 | 91.84 | 77.30 |
| 117 | 106.88 | 38.30 | 72.93 | 85.98 | 90.89 |
| 118 | 107.54 | 23.20 | 42.76 | 91.00 | 65.03 |
| 119 | 103.59 | 31.81 | 62.05 | 91.08 | 77.60 |
| 120 | 100.43 | 15.95 | 37.51 | 83.88 | 96.11 |

TABLE 7

| Ex. No. | CYP1A2 | CYP2C9 | CYP2C19 | CYP2D6 | CYP3A4 |
|---|---|---|---|---|---|
| 121 | 106.63 | 14.48 | 41.57 | 87.03 | 108.67 |
| 122 | 102.25 | 20.08 | 77.57 | 87.86 | 86.20 |
| 123 | 107.73 | 24.34 | 49.67 | 97.41 | 111.65 |
| 124 | 99.82 | 36.23 | 32.31 | 94.52 | 104.43 |
| 125 | 105.68 | 48.25 | 93.59 | 106.95 | 105.69 |
| 126 | 105.07 | 71.05 | 88.48 | 99.82 | 105.90 |
| 127 | 96.13 | 68.21 | 94.03 | 93.45 | 94.15 |
| 128 | 83.49 | 63.11 | 87.55 | 77.61 | 29.34 |
| 129 | 95.24 | 84.59 | 100.56 | 95.8 | 44.29 |
| 130 | 97.75 | 52.88 | 85.28 | 90.98 | 87.47 |
| 131 | 99.90 | 54.08 | 94.68 | 93.15 | 105.25 |
| 132 | 89.15 | 6.37 | 65.57 | 82.55 | 106.17 |
| 133 | 104.58 | 25.09 | 32.20 | 86.57 | 98.02 |
| 134 | 107.05 | 28.3 | 38.02 | 88.87 | 98.86 |
| 135 | 98.36 | 74.38 | 87.87 | 95.56 | 84.62 |

The invention claimed is:

1. A compound represented by the following Formula 1, or a pharmaceutically acceptable salt thereof:

[Formula I]

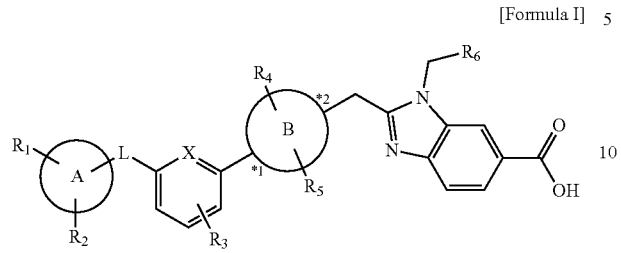

wherein

A is $C_{6-10}$ aryl; $C_{3-7}$ cycloalkyl; 5- or 6-membered heteroaryl containing one heteroatom selected from N, O, and S; 5- or 6-membered heterocycloalkyl containing one heteroatom selected from N, O, and S; or 9- or 10-membered fused heteroaryl containing at least one heteroatom selected from N, O, and S, B is any one of the following (1) to (5), (1) 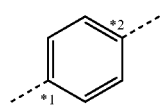

(2) 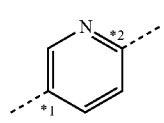

(3) 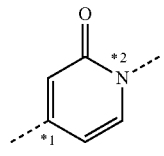

(4) 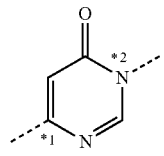

(5) 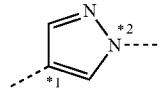

L is —(CH$_2$)n-O—, —O—(CH$_2$)n-, —(CH$_2$)n-NH—, —NH—(CH$_2$)n-, —(CH$_2$)n-N(C$_{1-5}$ alkyl)-, —N(C$_{1-5}$ alkyl)-(CH$_2$)n-, —CONH—, or —NHCO—, where n is 1 or 2, X is CH or N, $R_1$ and $R_2$ are each independently selected from the group consisting of hydrogen, $C_{1-5}$ alkyl, $C_{1-5}$ alkoxy, $C_{1-5}$ haloalkyl, halogen, cyano, and nitro, $R_3$ is hydrogen or halogen, $R_4$ and $R_5$ are each independently selected from the group consisting of hydrogen, $C_{1-5}$ alkyl, $C_{1-5}$ alkoxy, $C_{1-5}$ haloalkyl, halogen, cyano, and nitro, $R_6$ is —(CH$_2$)$_m$—O—(C$_{1-5}$ alkyl) (where m is 1 or 2); $C_{1-5}$ haloalkyl; 5- or 6-membered heteroaryl containing one or two heteroatoms selected from N, O, and S, which is unsubstituted or substituted with $C_{1-5}$ alkyl; or 4- or 5-membered heterocycloalkyl containing one heteroatom selected from N, O, and S, which is unsubstituted or substituted with $C_{1-5}$ alkyl.

2. The compound of claim 1, or a pharmaceutically acceptable salt thereof, wherein A is phenyl, pyridinyl, benzothiazolyl or cyclopropyl.

3. The compound of claim 1, or a pharmaceutically acceptable salt thereof, wherein L is —CH$_2$O—, or —OCH$_2$—.

4. The compound of claim 1, or a pharmaceutically acceptable salt thereof, wherein $R_1$ is hydrogen, methyl, methoxy, trifluoromethyl, fluoro, chloro, bromo, cyano, or nitro.

5. The compound of claim 1 or a pharmaceutically acceptable salt thereof, wherein $R_2$ is hydrogen, fluoro, chloro, or bromo.

6. The compound of claim 1, or a pharmaceutically acceptable salt thereof, wherein $R_3$ is hydrogen, fluoro, chloro, or bromo.

7. The compound of claim 1, or a pharmaceutically acceptable salt thereof, wherein $R_4$ is hydrogen, methyl, methoxy, fluoro, chloro, bromo, or nitro.

8. The compound of claim 1, or a pharmaceutically acceptable salt thereof, wherein $R_5$ is hydrogen, fluoro, chloro, or bromo.

9. The compound of claim 1, or a pharmaceutically acceptable salt thereof, wherein $R_6$ is —CH$_2$—O—CH$_3$; —CH$_2$F; furanyl; imidazolyl unsubstituted or substituted with methyl or ethyl; oxazolyl; pyridinyl; thiophenyl; oxetanyl; or tetrahydrofuranyl.

10. The compound of claim 1, wherein the compound is represented by the following Formula 1-1:

[Formula 1-1]

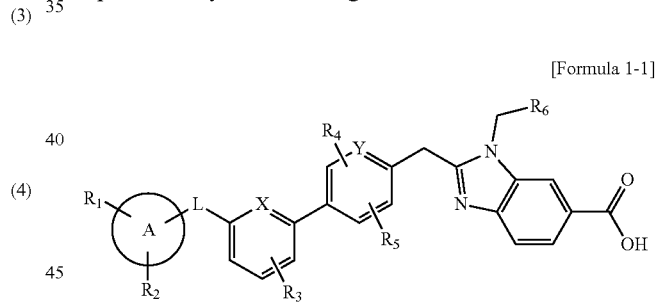

or a pharmaceutically acceptable salt thereof,
wherein,
Y is CH or N; and
A, L, X, and $R_1$ to $R_6$ are as defined in claim 1.

11. The compound of claim 1, wherein the compound is represented by the following Formula 1-2:

[Formula 1-2]

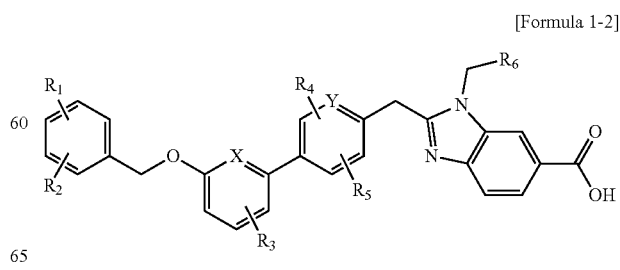

or a pharmaceutically acceptable salt thereof, wherein Y is CH or N; and

X and $R_1$ to $R_6$ are as defined in claim 1.

12. The compound of claim 1, wherein the compound is represented by the following Formula 1-3:

[Formula 1-3]

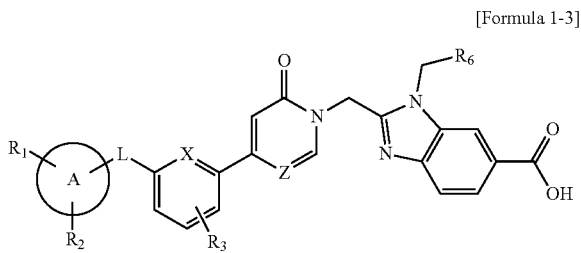

or a pharmaceutically acceptable salt thereof,
wherein
Z is CH or N; and
A, L, X and $R_1$, $R_2$, $R_3$ and $R_6$ are as defined in claim 1.

13. The compound of claim 1, wherein the compound is represented by the following Formula 1-4:

[Formula 1-4]

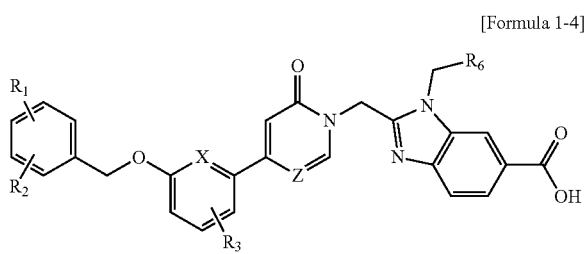

or a pharmaceutically acceptable salt thereof,
wherein
Z is CH or N; and
X and $R_1$, $R_2$, $R_3$ and $R_6$ are as defined in claim 1.

14. The compound of claim 1, wherein the compound is selected from the group consisting of:

1) 2-(4-(6-(4-chloro-2-fluorobenzyloxy)pyridin-2-yl)benzyl)-1-(pyridin-3-ylmethyl)-1H-benzo[d]imidazole-6-carboxylic acid,
2) 2-(4-(6-(4-chloro-2-fluorobenzyloxy)pyridin-2-yl)benzyl)-1-(2-methoxyethyl)-1H-benzo[d]imidazole-6-carboxylic acid,
3) 2-(4-(6-(4-chloro-2-fluorobenzyloxy)pyridin-2-yl)-2-fluorobenzyl)-1-(2-methoxyethyl)-1H-benzo[d]imidazole-6-carboxylic acid,
4) 2-(4-(6-(4-chloro-2-fluorobenzyloxy)pyridin-2-yl)-3-methylbenzyl)-1-(2-methoxyethyl)-1H-benzo[d]imidazole-6-carboxylic acid,
5) 2-(4-(6-(4-chloro-2-fluorobenzyloxy)pyridin-2-yl)-2-nitrobenzyl)-1-(2-methoxyethyl)-1H-benzo[d]imidazole-6-carboxylic acid,
6) 2-(4-(6-(4-chloro-2-fluorobenzyloxy)pyridin-2-yl)-3-fluorobenzyl)-1-(2-methoxyethyl)-1H-benzo[d]imidazole-6-carboxylic acid,
7) 2-(4-(6-((4-chloro-2-fluorophenoxy)methyl)pyridin-2-yl)-2-nitrobenzyl)-1-(2-methoxyethyl)-1H-benzo[d]imidazole-6-carboxylic acid,
8) 2-((3'-(4-cyano-2-fluorobenzyloxy) biphenyl-4-yl)methyl)-1-((tetrahydrofuran-2-yl)methyl)-1H-benzo[d]imidazole-6-carboxylic acid,
9) 2-((3'-(4-cyano-2-fluorobenzyloxy)-2-fluorobiphenyl-4-yl)methyl)-1-((tetrahydrofuran-2-yl)methyl)-1H-benzo[d]imidazole-6-carboxylic acid,
10) 2-(4-(6-(4-chloro-2-fluorobenzyloxy)pyridin-2-yl)benzyl)-1-((tetrahydrofuran-2-yl)methyl)-1H-benzo[d]imidazole-6-carboxylic acid,
11) 2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid,
12) 2-(4-(6-(4-chloro-2-fluorobenzyloxy)pyridin-2-yl)benzyl)-1-(furan-2-ylmethyl)-1H-benzo[d]imidazole-6-carboxylic acid,
13) 2-(4-(6-(4-chloro-2-fluorobenzyloxy)pyridin-2-yl)-2-fluorobenzyl)-1-(furan-2-ylmethyl)-1H-benzo[d]imidazole-6-carboxylic acid,
14) 2-((3'-(4-cyano-2-fluorobenzyloxy)-3-fluorobiphenyl-4-yl)methyl)-1-((tetrahydrofuran-2-yl)methyl)-1H-benzo[d]imidazole-6-carboxylic acid,
15) 2-(4-(6-(4-cyano-2-fluorobenzyloxy)pyridin-2-yl)-2-fluorobenzyl)-1-((tetrahydrofuran-2-yl)methyl)-1H-benzo[d]imidazole-6-carboxylic acid,
16) 2-((3'-(4-chloro-2-fluorobenzyloxy)-3-fluorobiphenyl-4-yl)methyl)-1-((tetrahydrofuran-2-yl)methyl)-1H-benzo[d]imidazole-6-carboxylic acid,
15) 2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid,
18) 2-(4-(6-(4-cyano-2-fluorobenzyloxy)pyridin-2-yl)benzyl)-1-(furan-2-ylmethyl)-1H-benzo[d]imidazole-6-carboxylic acid,
19) 2-(4-(6-(4-cyano-2-fluorobenzyloxy)pyridin-2-yl)-2-fluorobenzyl)-1-(furan-2-ylmethyl)-1H-benzo[d]imidazole-6-carboxylic acid,
20) 2-(4-(6-(4-cyano-2-fluorobenzyloxy)pyridin-2-yl)benzyl)-1-(2-methoxyethyl)-1H-benzo[d]imidazole-6-carboxylic acid,
21) 2-((3'-(4-cyano-2-fluorobenzyloxy) biphenyl-4-yl)methyl)-1-(2-methoxyethyl)-1H-benzo[d]imidazole-6-carboxylic acid,
22) 2-((3'-(4-chloro-2-fluorobenzyloxy) biphenyl-4-yl)methyl)-1-(2-methoxyethyl)-1H-benzo[d]imidazole-6-carboxylic acid,
23) 1-(furan-2-ylmethyl)-2-((5-(3-(3-methoxybenzyloxy)phenyl)pyridin-2-yl)methyl)-1H-benzo[d]imidazole-6-carboxylic acid,
24) 2-((3'-(4-chloro-2-fluorobenzyloxy) biphenyl-4-yl)methyl)-1-((tetrahydrofuran-2-yl)methyl)-1H-benzo[d]imidazole-6-carboxylic acid,
25) 2-(4-(6-(4-cyano-2-fluorobenzyloxy)pyridin-2-yl)-2-fluorobenzyl)-1-(2-methoxyethyl)-1H-benzo[d]imidazole-6-carboxylic acid,
26) 2-((3'-(4-cyano-2-fluorobenzyloxy)-3-fluorobiphenyl-4-yl)methyl)-1-(2-methoxyethyl)-1H-benzo[d]imidazole-6-carboxylic acid,
27) 2-((3'-(4-cyano-2-fluorobenzyloxy) biphenyl-4-yl)methyl)-1-(furan-2-ylmethyl)-1H-benzo[d]imidazole-6-carboxylic acid,
28) 2-((3'-(4-cyano-2-fluorobenzyloxy)-3-fluorobiphenyl-4-yl)methyl)-1-(furan-2-ylmethyl)-1H-benzo[d]imidazole-6-carboxylic acid,
29) 2-((3'-(4-cyano-2-fluorobenzyloxy)-2-methylbiphenyl-4-yl)methyl)-1-(furan-2-ylmethyl)-1H-benzo[d]imidazole-6-carboxylic acid,
30) 2-(4-(6-(4-cyano-2-fluorobenzyloxy)pyridin-2-yl)-3-methylbenzyl)-1-(furan-2-ylmethyl)-1H-benzo[d]imidazole-6-carboxylic acid, 31) 2-(4-(6-((4-chloro-2-fluorophenoxy)methyl)pyridin-2-yl)-2-fluorobenzyl)-1-(2-methoxyethyl)-1H-benzo[d]imidazole-6-carboxylic acid,
32) 2-((3'-(4-chloro-2-fluorobenzyloxy)-3-fluorobiphenyl-4-yl)methyl)-1-(oxazol-5-ylmethyl)-1H-benzo[d]imidazole-6-carboxylic acid,
33) 2-((3'-(4-chloro-2-fluorobenzyloxy)-2-fluorobiphenyl-4-yl)methyl)-1-(oxazol-5-ylmethyl)-1H-benzo[d]imidazole-6-carboxylic acid,
34) 2-(4-(6-(4-chloro-2-fluorobenzyloxy)pyridin-2-yl)-2-fluorobenzyl)-1-(oxazol-5-ylmethyl)-1H-benzo[d]imidazole-6-carboxylic acid,
35) 2-(4-(6-(4-chloro-2-fluorobenzyloxy)pyridin-2-yl)-3-fluorobenzyl)-1-(oxazol-5-ylmethyl)-1H-benzo[d]imidazole-6-carboxylic acid,
36) 2-((3'-(4-chloro-2-fluorobenzyloxy)-3-fluorobiphenyl-4-yl)methyl)-1-(2-methoxyethyl)-1H-benzo[d]imidazole-6-carboxylic acid,
37) 2-(4-(6-(4-chloro-2-fluorobenzyloxy)pyridin-2-yl)-2,6-difluorobenzyl)-1-(2-methoxyethyl)-1H-benzo[d]imidazole-6-carboxylic acid,
38) 2-(4-(6-(4-cyano-2-fluorobenzyloxy)pyridin-2-yl)-3-fluorobenzyl)-1-(2-methoxyethyl)-1H-benzo[d]imidazole-6-carboxylic acid,
39) 2-((3'-(4-chloro-2-fluorobenzyloxy)-2-fluorobiphenyl-4-yl)methyl)-1-(2-methoxyethyl)-1H-benzo[d]imidazole-6-carboxylic acid,
40) 2-((3'-(4-cyano-2-fluorobenzyloxy)-2-fluorobiphenyl-4-yl)methyl)-1-(2-methoxyethyl)-1H-benzo[d]imidazole-6-carboxylic acid,
41) (R)-2-((3'-(4-chloro-2-fluorobenzyloxy)-3-fluorobiphenyl-4-yl)methyl)-1-((tetrahydrofuran-2-yl)methyl)-1H-benzo[d]imidazole-6-carboxylic acid,
42) (R)-2-((3'-(4-chloro-2-fluorobenzyloxy)-2-fluorobiphenyl-4-yl)methyl)-1-((tetrahydrofuran-2-yl)methyl)-1H-benzo[d]imidazole-6-carboxylic acid,
43) 2-(4-(6-(4-chloro-2-fluorobenzyloxy)pyridin-2-yl)-2-fluorobenzyl)-1-(2-fluoroethyl)-1H-benzo[d]imidazole-6-carboxylic acid,
44) 2-(4-(6-(4-cyano-2-fluorobenzyloxy)pyridin-2-yl)-2-fluorobenzyl)-1-(2-fluoroethyl)-1H-benzo[d]imidazole-6-carboxylic acid,
45) (R)-2-(4-(6-((4-chloro-2-fluorophenoxy)methyl)pyridin-2-yl)-2-fluorobenzyl)-1-((tetrahydrofuran-2-yl)methyl)-1H-benzo[d]imidazole-6-carboxylic acid,
46) (R)-2-((3'-(4-cyano-2-fluorobenzyloxy)-3-fluorobiphenyl-4-yl)methyl)-1-((tetrahydrofuran-2-yl)methyl)-1H-benzo[d]imidazole-6-carboxylic acid,
47) (R)-2-((3'-(4-cyano-2-fluorobenzyloxy)-2-fluorobiphenyl-4-yl)methyl)-1-((tetrahydrofuran-2-yl)methyl)-1H-benzo[d]imidazole-6-carboxylic acid,
48) 2-((3'-(4-chloro-2-fluorobenzyloxy)-3,5-difluorobiphenyl-4-yl)methyl)-1-(2-methoxyethyl)-1H-benzo[d]imidazole-6-carboxylic acid,
49) 2-(4-(6-(4-chloro-2-fluorobenzyloxy)pyridin-2-yl)-2-fluorobenzyl)-1-(thiophen-2-ylmethyl)-1H-benzo[d]imidazole-6-carboxylic acid,
50) 2-(4-(6-(4-chloro-2-fluorobenzyloxy)pyridin-2-yl)-3-fluorobenzyl)-1-(thiophen-2-ylmethyl)-1H-benzo[d]imidazole-6-carboxylic acid,
51) (R)-2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid,
52) (R)-2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid,
53) 2-(4-(6-(4-chloro-2-fluorobenzyloxy)pyridin-2-yl)-2-methylbenzyl)-1-(2-methoxyethyl)-1H-benzo[d]imidazole-6-carboxylic acid,
54) 2-(4-(6-(4-cyano-2-fluorobenzyloxy)pyridin-2-yl)-2-methylbenzyl)-1-(2-methoxyethyl)-1H-benzo[d]imidazole-6-carboxylic acid,
55) 2-(4-(6-(4-chloro-2-fluorobenzyloxy)pyridin-2-yl)-3-fluorobenzyl)-1-(2-fluoroethyl)-1H-benzo[d]imidazole-6-carboxylic acid,
56) 2-((3'-(4-chloro-2-fluorobenzyloxy)-3-fluorobiphenyl-4-yl)methyl)-1-(2-fluoroethyl)-1H-benzo[d]imidazole-6-carboxylic acid,
57) 2-((3'-(4-cyano-2-fluorobenzyloxy)-3-fluorobiphenyl-4-yl)methyl)-1-(2-fluoroethyl)-1H-benzo[d]imidazole-6-carboxylic acid,
58) 2-(4-(6-(4-cyano-2-fluorobenzyloxy)pyridin-2-yl)-3-fluorobenzyl)-1-(2-fluoroethyl)-1H-benzo[d]imidazole-6-carboxylic acid,
59) (S)-2-(4-(6-(4-chloro-2-fluorobenzyloxy)pyridin-2-yl)-2-fluorobenzyl)-1-((tetrahydrofuran-2-yl)methyl)-1H-benzo[d]imidazole-6-carboxylic acid,
60) (S)-2-(4-(6-(4-chloro-2-fluorobenzyloxy)pyridin-2-yl)-3-fluorobenzyl)-1-((tetrahydrofuran-2-yl)methyl)-1H-benzo[d]imidazole-6-carboxylic acid,
61) 2-(4-(6-(4-chloro-2-fluorobenzyloxy)pyridin-2-yl)-2,3-difluorobenzyl)-1-((tetrahydrofuran-2-yl)methyl)-1H-benzo[d]imidazole-6-carboxylic acid,
62) 2-(4-(6-(4-cyano-2-fluorobenzyloxy)pyridin-2-yl)-2,3-difluorobenzyl)-1-((tetrahydrofuran-2-yl)methyl)-1H-benzo[d]imidazole-6-carboxylic acid,
63) 2-(4-(6-(4-chloro-2-fluorobenzyloxy)pyridin-2-yl)-2-methoxybenzyl)-1-((tetrahydrofuran-2-yl)methyl)-1H-benzo[d]imidazole-6-carboxylic acid,
64) 2-(4-(6-(4-cyano-2-fluorobenzyloxy)pyridin-2-yl)-2-methoxybenzyl)-1-((tetrahydrofuran-2-yl)methyl)-1H-benzo[d]imidazole-6-carboxylic acid,
65) 2-(4-(6-(4-chloro-2-fluorobenzyloxy)pyridin-2-yl)-2,6-difluorobenzyl)-1-((tetrahydrofuran-2-yl)methyl)-1H-benzo[d]imidazole-6-carboxylic acid,
66) (S)-2-(4-(6-(4-cyano-2-fluorobenzyloxy)pyridin-2-yl)-2-fluorobenzyl)-1-((tetrahydrofuran-2-yl)methyl)-1H-benzo[d]imidazole-6-carboxylic acid,
67) (S)-2-(4-(6-(4-cyano-2-fluorobenzyloxy)pyridin-2-yl)-3-fluorobenzyl)-1-((tetrahydrofuran-2-yl)methyl)-1H-benzo[d]imidazole-6-carboxylic acid,
68) 2-(4-(6-(4-cyano-2-fluorobenzyloxy)pyridin-2-yl)-2-methylbenzyl)-1-((tetrahydrofuran-2-yl)methyl)-1H-benzo[d]imidazole-6-carboxylic acid,
69) 2-(4-(6-(4-chloro-2-fluorobenzyloxy)pyridin-2-yl)-2-methylbenzyl)-1-((tetrahydrofuran-2-yl)methyl)-1H-benzo[d]imidazole-6-carboxylic acid,
70) 2-(4-(6-(4-chloro-2-fluorobenzyloxy)pyridin-2-yl)-2,5-difluorobenzyl)-1-((tetrahydrofuran-2-yl)methyl)-1H-benzo[d]imidazole-6-carboxylic acid,
71) 2-(4-(6-(4-cyano-2-fluorobenzyloxy)pyridin-2-yl)-2,5-difluorobenzyl)-1-((tetrahydrofuran-2-yl)methyl)-1H-benzo[d]imidazole-6-carboxylic acid,
72) 2-(4-(6-(4-chloro-2-fluorobenzyloxy)pyridin-2-yl)-2-fluorobenzyl)-1-((1-ethyl-1H-imidazol-5-yl)methyl)-1H-benzo[d]imidazole-6-carboxylic acid,
73) (S)-2-(4-(6-(4-cyano-2-fluorobenzyloxy)pyridin-2-yl)-2-fluorobenzyl)-1-(oxetan-2-ylmethyl)-1H-benzo[d]imidazole-6-carboxylic acid,
74) (S)-2-(4-(6-(4-cyano-2-fluorobenzyloxy)pyridin-2-yl)-3-fluorobenzyl)-1-(oxetan-2-ylmethyl)-1H-benzo[d]imidazole-6-carboxylic acid, 75) 2-(4-(6-(4-chlorobenzyloxy)pyridin-2-yl)-2-fluorobenzyl)-1-((tetrahydrofuran-2-yl)methyl)-1H-benzo[d]imidazole-6-carboxylic acid, 76) 2-(2-fluoro-4-(6-(4-methylbenzyloxy)pyridin-2-yl)benzyl)-1-((tetrahydrofuran-2-yl)methyl)-1H-benzo[d]imidazole-6-carboxylic acid, 77) 2-(2-fluoro-4-(6-(4-(trifluoromethyl)benzyloxy)pyridin-2-yl)benzyl)-1-((tetrahydrofuran-2-yl)methyl)-1H-benzo[d]imidazole-6-carboxylic acid, 78) (S)-2-(4-(6-(4-chloro-2-fluorobenzyloxy)pyridin-2-yl)-2-fluorobenzyl)-1-(oxetan-2-ylmethyl)-1H-benzo[d]imidazole-6-carboxylic acid, 79) (S)-2-(4-(6-(4-chloro-2-fluorobenzyloxy)pyridin-2-yl)-3-fluorobenzyl)-1-(oxetan-2-ylmethyl)-1H-benzo[d]imidazole-6-carboxylic acid, 80) 2-(2-fluoro-4-(6-(3-methylbenzyloxy)pyridin-2-yl)benzyl)-1-((tetrahydrofuran-2-yl)methyl)-1H-benzo[d]imidazole-6-carboxylic acid, 81) 2-(2-fluoro-4-(6-(3-methoxybenzyloxy)pyridin-2-yl)benzyl)-1-((tetrahydrofuran-2-yl)methyl)-1H-benzo[d]imidazole-6-carboxylic acid, 82) (S)-2-(4-(6-(4-chloro-2-fluorobenzyloxy)pyridin-2-yl)-2,3-difluorobenzyl)-1-(oxetan-2-ylmethyl)-1H-benzo[d]imidazole-6-carboxylic acid, 83) 2-(4-(6-(benzyloxy)pyridin-2-yl)-2-fluorobenzyl)-1-((tetrahydrofuran-2-yl)methyl)-1H-benzo[d]imidazole-6-carboxylic acid, 84) (S)-2-(4-(6-(4-chloro-2-fluorobenzyloxy)pyridin-2-yl)-2,6-difluorobenzyl)-1-(oxetan-2-ylmethyl)-1H-benzo[d]imidazole-6-carboxylic acid, 85) 2-(4-(6-(3,4-difluorobenzyloxy)pyridin-2-yl)-2-fluorobenzyl)-1-((tetrahydrofuran-2-yl)methyl)-1H-benzo[d]imidazole-6-carboxylic acid, 86) (S)-2-(4-(6-(4-chloro-2-fluorobenzyloxy)pyridin-2-yl)-2,5-difluorobenzyl)-1-(oxetan-2-ylmethyl)-1H-benzo[d]imidazole-6-carboxylic acid, 87) 2-(4-(6-(4-cyanobenzyloxy)pyridin-2-yl)-2-fluorobenzyl)-1-((tetrahydrofuran-2-yl)methyl)-1H-benzo[d]imidazole-6-carboxylic acid, 88) 2-(2-fluoro-4-(6-(4-nitrobenzyloxy)pyridin-2-yl)benzyl)-1-((tetrahydrofuran-2-yl)methyl)-1H-benzo[d]imidazole-6-carboxylic acid, 89) 2-(4-(6-(4-bromo-2-fluorobenzyloxy)pyridin-2-yl)-2-fluorobenzyl)-1-((tetrahydrofuran-2-yl)methyl)-1H-benzo[d]imidazole-6-carboxylic acid, 90) 2-(3-fluoro-4-(6-(3-methylbenzyloxy)pyridin-2-yl)benzyl)-1-((tetrahydrofuran-2-yl)methyl)-1H-benzo[d]imidazole-6-carboxylic acid, 91) 2-(4-(6-(4-chloro-2-fluorobenzyloxy)-5-fluoropyridin-2-yl)-2-fluorobenzyl)-1-((tetrahydrofuran-2-yl)methyl)-1H-benzo[d]imidazole-6-carboxylic acid, 92) 2-((3'-(4-chloro-2-fluorobenzyloxy)-2,4'-difluorobiphenyl-4-yl)methyl)-1-((tetrahydrofuran-2-yl)methyl)-1H-benzo[d]imidazole-6-carboxylic acid, 93) 2-((3'-(4-cyano-2-fluorobenzyloxy)-2,4'-difluorobiphenyl-4-yl)methyl)-1-((tetrahydrofuran-2-yl)methyl)-1H-benzo[d]imidazole-6-carboxylic acid, 94) 2-(4-(6-(4-chlorobenzyloxy)pyridin-2-yl)-3-fluorobenzyl)-1-((tetrahydrofuran-2-yl)methyl)-1H-benzo[d]imidazole-6-carboxylic acid, 95) 2-((3'-(4-chloro-2-fluorobenzyloxy)-3,4'-difluorobiphenyl-4-yl)methyl)-1-((tetrahydrofuran-2-yl)methyl)-1H-benzo[d]imidazole-6-carboxylic acid, 96) 2-((3'-(4-cyano-2-fluorobenzyloxy)-3,4'-difluorobiphenyl-4-yl)methyl)-1-((tetrahydrofuran-2-yl)methyl)-1H-benzo[d]imidazole-6-carboxylic acid, 97) 2-(3-fluoro-4-(6-(4-(trifluoromethyl)benzyloxy)pyridin-2-yl)benzyl)-1-((tetrahydrofuran-2-yl)methyl)-1H-benzo[d]imidazole-6-carboxylic acid, 98) 2-(4-(6-(3,4-difluorobenzyloxy)pyridin-2-yl)-3-fluorobenzyl)-1-((tetrahydrofuran-2-yl)methyl)-1H-benzo[d]imidazole-6-carboxylic acid, 99) 2-(4-(6-(4-chloro-3-fluorobenzyloxy)pyridin-2-yl)-3-fluorobenzyl)-1-((tetrahydrofuran-2-yl)methyl)-1H-benzo[d]imidazole-6-carboxylic acid, 100) 2-(4-(6-(3-chloro-5-fluorobenzyloxy)pyridin-2-yl)-3-fluorobenzyl)-1-((tetrahydrofuran-2-yl)methyl)-1H-benzo[d]imidazole-6-carboxylic acid, 101) 2-(4-(6-(2-chloro-6-fluorobenzyloxy)pyridin-2-yl)-3-fluorobenzyl)-1-((tetrahydrofuran-2-yl)methyl)-1H-benzo[d]imidazole-6-carboxylic acid, 102) 2-((5-(3-(4-chloro-2-fluorobenzyloxy)-4-fluorophenyl)pyridin-2-yl)methyl)-1-((tetrahydrofuran-2-yl)methyl)-1H-benzo[d]imidazole-6-carboxylic acid, 103) (S)-2-(4-(6-(4-cyano-2-fluorobenzyloxy)pyridin-2-yl)-2,6-difluorobenzyl)-1-(oxetan-2-ylmethyl)-1H-benzo[d]imidazole-6-carboxylic acid, 104) 2-((4-(3-(4-cyano-2-fluorobenzyloxy)phenyl)-2-oxopyridin-1 (2H)-yl)methyl)-1-(2-methoxyethyl)-1H-benzo[d]imidazole-6-carboxylic acid, 105) 2-((4-(6-(4-chloro-2-fluorobenzyloxy)pyridin-2-yl)-2-oxopyridin-1 (2H)-yl)methyl)-1-((tetrahydrofuran-2-yl)methyl)-1H-benzo[d]imidazole-6-carboxylic acid, 106) 2-((4-(3-(4-chloro-2-fluorobenzyloxy)phenyl)-2-oxopyridin-1 (2H)-yl)methyl)-1-((tetrahydrofuran-2-yl)methyl)-1H-benzo[d]imidazole-6-carboxylic acid, 107) 2-((4-(3-(4-cyano-2-fluorobenzyloxy)phenyl)-2-oxopyridin-1 (2H)-yl)methyl)-1-((tetrahydrofuran-2-yl)methyl)-1H-benzo[d]imidazole-6-carboxylic acid, 108) (S)-2-((4-(6-(4-chloro-2-fluorobenzyloxy)pyridin-2-yl)-2-oxopyridin-1 (2H)-yl)methyl)-1-((tetrahydrofuran-2-yl)methyl)-1H-benzo[d]imidazole-6-carboxylic acid, 109) (S)-2-((4-(6-(4-cyano-2-fluorobenzyloxy)pyridin-2-yl)-2-oxopyridin-1 (2H)-yl)methyl)-1-((tetrahydrofuran-2-yl)methyl)-1H-benzo[d]imidazole-6-carboxylic acid, 110) (S)-2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid, 111) (S)-2-((4-(6-(4-cyano-2-fluorobenzyloxy)pyridin-2-yl)-2-oxopyridin-1 (2H)-yl)methyl)-1-(oxetan-2-ylmethyl)-1H-benzo[d]imidazole-6-carboxylic acid, 112) 2-((4-(6-(4-chloro-2-fluorobenzyloxy)pyridin-2-yl)-6-oxopyrimidin-1 (6H)-yl)methyl)-1-((tetrahydrofuran-2-yl)methyl)-1H-benzo[d]imidazole-6-carboxylic acid, 113) (S)-2-(4-(6-((4-cyano-2-fluorobenzyl)oxy)pyridin-2-yl)-2,3-difluorobenzyl)-1-(oxetan-2-ylmethyl)-1H-benzo[d]imidazole-6-carboxylic acid, 114) 2-(4-(6-((4-cyano-2-fluorobenzyl)oxy)pyridin-2-yl)-3-fluorobenzyl)-1-(oxetan-2-ylmethyl)-1H-benzo[d]imidazole-6-carboxylic acid, 115) (S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid, 116) (S)-2-(4-(6-((4-chloro-2-fluorobenzyl)oxy)pyridin-2-yl)-2,5-difluorobenzyl)-1-((tetrahydrofuran-2-yl)methyl)-1H-benzo[d]imidazole-6-carboxylic acid, 117) (S)-2-(4-(6-((4-chloro-2-fluorobenzyl)oxy)-5-fluoropyridin-2-yl)-3-fluorobenzyl)-1-(oxetan-2-ylmethyl)-1H-benzo[d]imidazole-6-carboxylic acid, 118) (S)-2-(4-(6-((4-cyanobenzyl)oxy)pyridin-2-yl)-3-fluorobenzyl)-1-(oxetan-2-ylmethyl)-1H-benzo[d]imidazole-6-carboxylic acid, 119) (S)-2-(4-(6-((2,4-difluorobenzyl)oxy)pyridin-2-yl)-3-fluorobenzyl)-1-(oxetan-2-ylmethyl)-1H-benzo[d]imidazole-6-carboxylic acid, 120) (S)-2-(4-(6-((4-cyano-2-fluorobenzyl)oxy)pyridin-2-yl)-2,5-difluorobenzyl)-1-((tetrahydrofuran-2-yl)methyl)-1H-benzo[d]imidazole-6-carboxylic acid, 121) (S)-2-(3-fluoro-4-(6-((4-(trifluoromethyl)benzyl)oxy)pyridin-2-yl)benzyl)-1-(oxetan-2-ylmethyl)-1H-benzo[d]imidazole-6-carboxylic acid, 122) (S)-2-(3-fluoro-4-(6-((4-methoxybenzyl)oxy)pyridin-2-yl)benzyl)-1-(oxetan-2-ylmethyl)-1H-benzo[d]imidazole-6-carboxylic acid, 123) (S)-2-(4-(6-((4-chlorobenzyl)oxy)pyridin-2-yl)-3-fluorobenzyl)-1-(oxetan-2-ylmethyl)-1H-benzo[d]imidazole-6-carboxylic acid, 124) (S)-2-(3-fluoro-4-(6-((4-nitrobenzyl)oxy)pyridin-2-yl)benzyl)-1-(oxetan-2-ylmethyl)-1H-benzo[d]imidazole-6-carboxylic acid, 125) (S)-2-(4-(6-((3,4-difluorobenzyl)oxy)pyridin-2-yl)-3-fluorobenzyl)-1-(oxetan-2-ylmethyl)-1H-benzo[d]imidazole-6-carboxylic acid, 126) (S)-2-(4-(6-((2-chloro-6-fluorobenzyl)oxy)pyridin-2-yl)-3-fluorobenzyl)-1-(oxetan-2-ylmethyl)-1H-benzo[d]imidazole-6-carboxylic acid, 127) 2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid, 128) (S)-2-(3-fluoro-4-(6-(pyridin-4-ylmethoxy)pyridin-2-yl)benzyl)-1-(oxetan-2-ylmethyl)-1H-benzo[d]imidazole-6-carboxylic acid, 129) (S)-2-(3-fluoro-4-(6-(pyridin-3-ylmethoxy)pyridin-2-yl)benzyl)-1-(oxetan-2-ylmethyl)-1H-benzo[d]imidazole-6-carboxylic acid, 130) 2-(4-(6-((4-cyano-2-fluorobenzyl)oxy)pyridin-2-yl)-3-fluorobenzyl)-1-((tetrahydrofuran-2-yl)methyl)-1H-benzo[d]imidazole-6-carboxylic acid, 131) (S)-2-((4-(6-((4-chloro-2-fluorobenzyl)oxy)pyridin-2-yl)-1H-pyrazol-1-yl)methyl)-1-(oxetan-2-ylmethyl)-1H-benzo[d]imidazole-6-carboxylic acid, 132) (S)-2-(4-(6-(benzo[d]thiazol-2-ylmethoxy)pyridin-2-yl)-3-fluorobenzyl)-1-(oxetan-2-ylmethyl)-1H-benzo[d]imidazole-6-carboxylic acid, 133) (S)-2-(4-(6-((4-cyano-2-fluorobenzyl)oxy)pyridin-2-yl)-2-methylbenzyl)-1-(oxetan-2-ylmethyl)-1H-benzo[d]imidazole-6-carboxylic acid, 134) (S)-2-(4-(6-((4-chloro-2-fluorobenzyl)oxy)pyridin-2-yl)-2-methylbenzyl)-1-(oxetan-2-ylmethyl)-1H-benzo[d]imidazole-6-carboxylic acid, and 135) (S)-2-(4-(6-(cyclopropylmethoxy)pyridin-2-yl)-3-fluorobenzyl)-1-(oxetan-2-ylmethyl)-1H-benzo[d]imidazole-6-carboxylic acid, or a pharmaceutically acceptable salt thereof.

15. A pharmaceutical composition comprising the compound of claim 1 or a pharmaceutically acceptable salt thereof.

\* \* \* \* \*